131

(12) United States Patent
Hermanson et al.

(10) Patent No.: US 9,252,003 B2
(45) Date of Patent: Feb. 2, 2016

(54) ABSOLUTE QUANTITATION OF PROTEINS AND PROTEIN MODIFICATIONS BY MASS SPECTROMETRY WITH MULTIPLEXED INTERNAL STANDARDS

(71) Applicant: Pierce Biotechnology, Inc., Rockford, IL (US)

(72) Inventors: Greg Hermanson, Loves Park, IL (US); John Charles Rogers, Rockton, IL (US); Joel Louette, Ulm (DE); Ryan Daniel Bomgarden, Winnebago, IL (US); Bhavinkumar Patel, Rockford, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 54 days.

(21) Appl. No.: 14/297,696

(22) Filed: Jun. 6, 2014

(65) Prior Publication Data

US 2014/0364337 A1 Dec. 11, 2014

Related U.S. Application Data

(60) Provisional application No. 61/832,380, filed on Jun. 7, 2013.

(51) Int. Cl.
| | | |
|---|---|---|
| *G01N 31/00* | (2006.01) | |
| *G01N 33/53* | (2006.01) | |
| *H01J 49/00* | (2006.01) | |
| *G01N 33/60* | (2006.01) | |
| *G01N 33/68* | (2006.01) | |

(52) U.S. Cl.
CPC ............ *H01J 49/0031* (2013.01); *G01N 33/60* (2013.01); *G01N 33/6848* (2013.01)

(58) Field of Classification Search
CPC .......... C07B 59/008; C07K 1/13; G06F 19/18
See application file for complete search history.

(56) References Cited

U.S. PATENT DOCUMENTS

| | | | |
|---|---|---|---|
| 7,501,286 B2 | 3/2009 | Gygi et al. | |
| 7,939,331 B2 | 5/2011 | Leite et al. | |
| 8,399,402 B2 | 3/2013 | Beynon et al. | |
| 2002/0076739 A1 | 6/2002 | Aebersold et al. | |
| 2004/0072251 A1 | 4/2004 | Anderson et al. | |
| 2004/0229283 A1 | 11/2004 | Gygi et al. | |
| 2005/0124014 A1 | 6/2005 | Chen | |
| 2009/0176199 A1 | 7/2009 | Lee et al. | |
| 2010/0261279 A1 | 10/2010 | Ranish et al. | |
| 2011/0022326 A1 | 1/2011 | Oda et al. | |
| 2014/0120565 A1 | 5/2014 | Coon et al. | |

FOREIGN PATENT DOCUMENTS

| | | |
|---|---|---|
| WO | 03/016861 | 2/2003 |
| WO | 03/046148 | 7/2003 |
| WO | 2007/031080 | 3/2007 |
| WO | 2012/005838 | 1/2012 |
| WO | 2012/006406 | 1/2012 |

OTHER PUBLICATIONS

Hebert et al. Neutron-encoded mass signatures for multiplexed proteome quantification. Nature Methods. 10 (2013) 332-336.
Michalski et al. Mass Spectrometry-based Proteomics Using Q Exactive, a High-performance Benchtop Quadrupole Orbitrap Mass Spectrometer. Mol. & Cell. Proteomics 10 (2011) 1-12.
Polanski and Anderson. A List of Candidate Cancer Biomarkers for Targeted Proteomics. Biomarker Insights 1 (2006) 1- 48.
Werner et al. High-Resolution Enabled TMT 8-plexing. Anal. Chem. 84 (2012) 7188-7194.
McAlister et al. Increasing the Multiplexing Capacity of TMTs Using Reporter Ion Isotopologues with Isobaric Masses. Anal. Chem. 84 (2012) 7469-7478.
Krokhin et al. An Improved Model for Prediction of Retention Times of Tryptic Peptides in Ion Pair Reversed-phase HPLC. Mol. & Cell. Proteomics 3 (2004) 908-919.
Anderson and Anderson. The human plasma proteome: History, character, and diagnostic prospects. Mol. Cell. Proteomics 1 (2002) 845-867.
Spicer et al. Sequence-specific retention calculator. A family of peptide retention time prediction algorithms in reversed-phase HPLC: applicability to various chromatographic conditions and columns. Anal Chem. 79 (2007) 8762-8768.
Search Report and Written Opinion for PCT/US2011/038629, mailed Nov. 3, 2011, 15 pages.
Gerber et al. Absolute quantification of proteins and phosphoproteins from cell lysates by tandem MS. Proc Natl Acad Sci (US) Jun. 10, 2003, vol. 100, No. 12, 6940-6945.
Guerrera and Kleiner. Application of Mass Spectrometry in Proteomics, Bioscience Reports, vol. 25, 2005, pp. 71-93.
Hewel et al. Synthetic Peptide Arrays for Pathway-Level Protein Monitoring by Liquid Chromatography-Tandem Mass Spectrometry. Molecular & Cellular Proteomics 9.11 (2010), pp. 2460-2473. http://www.mcponline.org; Supplemental Figures (13 pp.); Supplemental Information (16 pp.); Supplemental Tables (81 pp.), http://www.mcponline.org/content/9/11/2460/suppl/DC1.
Holzmann et al. Lesson from the Stoichiometry Determination of the Cohesion Complex: A Short Protease Mediated Elution Increases the Recovery from Cross-Linked Antibody-Conjugated Beads. Journal of Proteome Research, 2011, 10, pp. 780-789.

(Continued)

*Primary Examiner* — Lisa Cook
(74) *Attorney, Agent, or Firm* — Thompson Hine LLP

(57) ABSTRACT

A method for absolute protein or peptide quantitation by mass spectroscopy. A sample containing a protein or peptide of interest is prepared for mass spectroscopy analysis. The sample is subjected to mass spectroscopy analysis at low resolution whereby a single additive mass spectroscopy peak is obtained, then is subjected to high resolution mass spectroscopy analysis whereby a plurality of mass spectroscopy peaks are obtained. The intensity of each of the plurality of mass spectroscopy peaks is quantitated either by comparison to an internal standard set, or by using a standard curve generated for each isotopologue set. Quantitation using a standard curve enhances quantitation across a dynamic range of analyte.

20 Claims, 25 Drawing Sheets

(56) References Cited

OTHER PUBLICATIONS

Holzmann et al. Stoichiometry Determination of the MP1-p14 Complex Using a Novel and Cost-Efficient Method to Produce an Equimolar Mixture of Standard Peptides. Analytical Chemistry, vol. 81, No. 24, Dec. 15, 2009, pp. 10254-10261.

Kim et al. Biomarker Detection and Quantification in Bodily Fluids Using Concatenated Reference Peptides Including a Universal Reporter. HUPO Sep. 4-7, 2011, 3 pages.

Kim et al. Novel proteomics approach for absolute quantification using polypeptides containing a reporter as internal standards. ASMS Jun. 5-9, 2011, 3 pages.

Ong et al. Stable Isotope Labeling by Amino Acids in Cell Culture, SILAC, as a Simple and Accurate Approach to Expression Proteomics. Molecular & Cellular Proteomics 1.5 (2002), pp. 376-386.

Rivers et al. Absolute Multiplexed Quantitative Analysis of Protein Expression during Muscle Development Using QconCAT. Molecular & Cellular Proteomics 6.8 (2007), pp. 1416-1427.

International Preliminary Report on Patentability, PCT/US2011/038629, issued Jan. 8, 2013 (8 pages).

International Search Report and Written Opinion for PCT/US2011/043159 mailed Mar. 27, 2012, 17 pages.

Hanke et al. Absolute SILAC for Accurate Quantitation of Proteins in Complex Mixtures Down to Attomole Level. Journal of Proteome Research vol. 7 (2008), pp. 1118-1130.

International Search Report PCT/US14/41208 mailed Sep. 25, 2014, 2 pages.

Written Opinion PCT/US14/41208 mailed Sep. 25, 2014, 4 pages.

Notice of Transmittal, PCT/US14/41208 mailed Sep. 25, 2014 1 page.

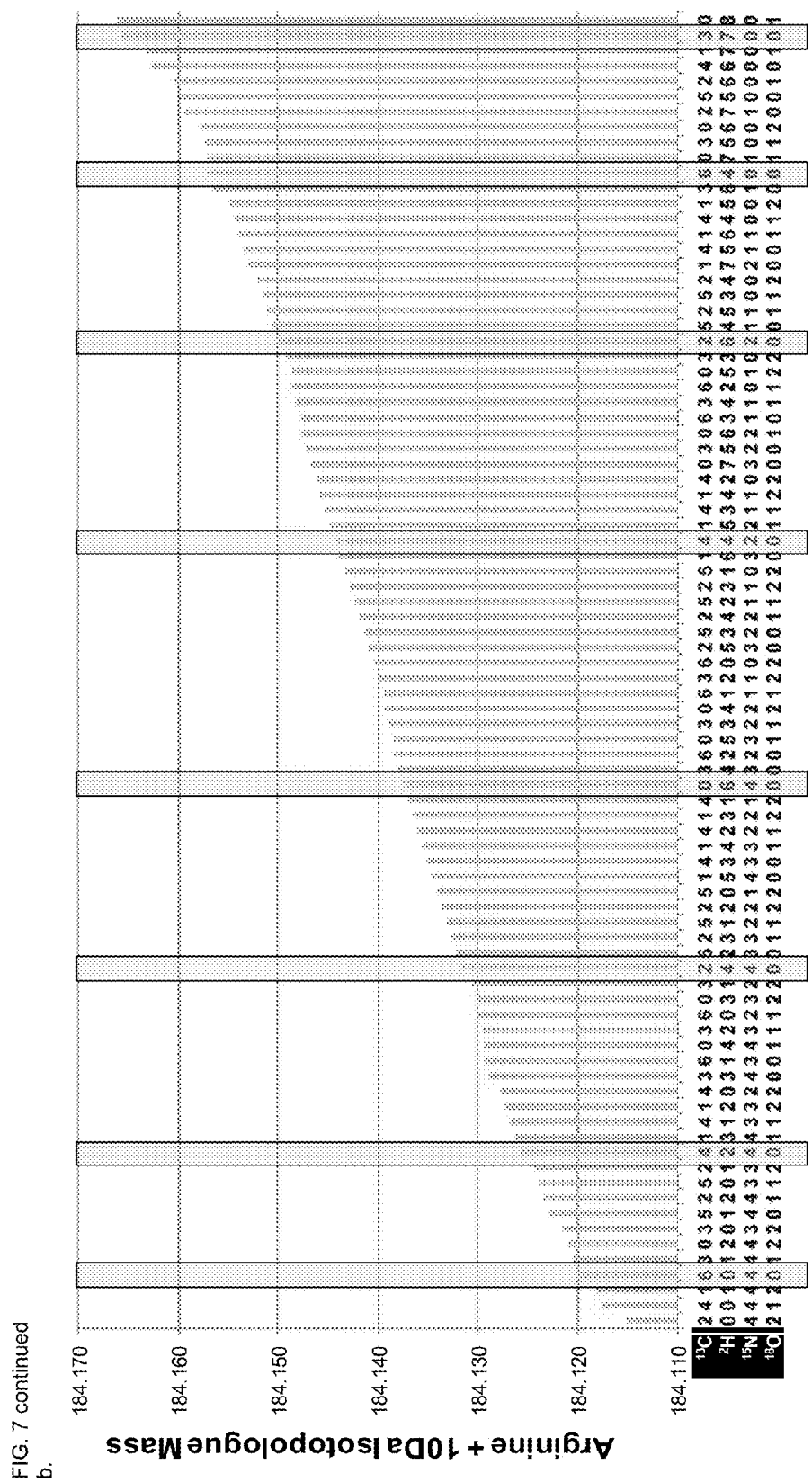
FIG. 7 continued b.

> >A* or A*plex> R or Rplex >

> >U or Uplex >

> Proteolytic site

> Heavy AA or heavy AA isotopologue set

Proteolytic site

Heavy AA or heavy AA isotopologue set

> Proteolytic site

> Heavy AA

> Heavy AA isotopologue set

A*plex, B*plex, and C*plex = heavy proteotypic peptide isotopologue sets
R = Reporter peptide
A*plexB*plexC*plexR = HeavyPeptide IGNIS™ AQUAplex
Uplex = Universal reporter peptide isotopologue set
R* = Heavy arginine isotopologue set
R° = Unique heavy isotopologue

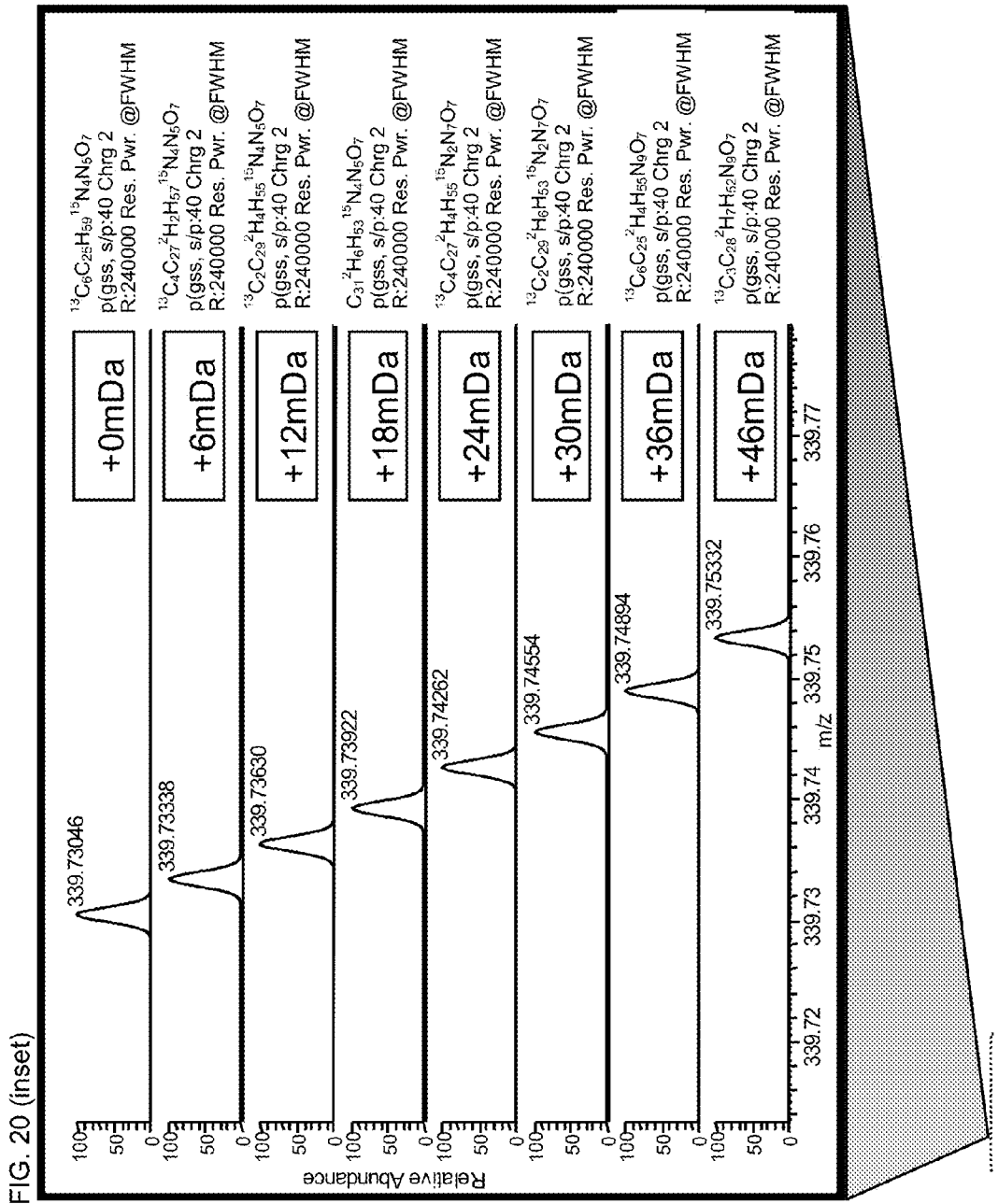

SEQUENCE LISTING

```
<160> NUMBER OF SEQ ID NOS: 64

<210> SEQ ID NO 1
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Pro Val Val Val Pro Arg
1               5

<210> SEQ ID NO 2
<211> LENGTH: 10
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 2

Ser Ser Ala Ala Pro Pro Pro Pro Arg
1               5                   10

<210> SEQ ID NO 3
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Thr Thr Val Ser Lys Thr Glu Thr Ser Gln Val Ala Pro Ala
1               5                   10

<210> SEQ ID NO 4
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Thr Glu Thr Ser Gln Val Ala Pro Ala
1               5

<210> SEQ ID NO 5
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Thr Thr Val Ser Lys
1               5

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Ile Ser Asn Glu Gly Gln Asn Ala Ser Ile Lys
1               5                   10

<210> SEQ ID NO 7
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7
```

```
His Val Leu Thr Ser Ile Gly Glu Lys
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Asp Ile Pro Val Pro Lys Pro Lys
1               5

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ile Gly Asp Tyr Ala Gly Ile Lys
1               5

<210> SEQ ID NO 10
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Thr Ala Ser Glu Phe Asp Ser Ala Ile Ala Gln Asp Lys
1               5                   10

<210> SEQ ID NO 11
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ser Ala Ala Gly Ala Phe Gly Pro Glu Leu Ser Arg
1               5                   10

<210> SEQ ID NO 12
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Glu Leu Gly Gln Ser Gly Val Asp Thr Tyr Leu Gln Thr Lys
1               5                   10
```

```
<210> SEQ ID NO 13
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ser Phe Ala Asn Gln Pro Leu Glu Val Val Tyr Ser Lys
1               5                   10

<210> SEQ ID NO 14
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Leu Ile Leu Val Gly Gly Tyr Gly Thr Arg
1               5                   10

<210> SEQ ID NO 15
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Ile Leu Phe Val Gly Ser Gly Val Ser Gly Gly Glu Glu Gly Ala
1               5                   10                  15

Arg

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Leu Thr Ile Leu Glu Glu Leu Arg
1               5

<210> SEQ ID NO 17
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Asn Gly Phe Ile Leu Asp Gly Phe Pro Arg
1               5                   10

<210> SEQ ID NO 18
```

-continued

```
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Glu Leu Ala Ser Gly Leu Ser Phe Pro Val Gly Phe Lys
1               5                   10

<210> SEQ ID NO 19
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Leu Ser Ser Glu Ala Pro Ala Leu Phe Gln Phe Asp Leu Lys
1               5                   10

<210> SEQ ID NO 20
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

His Glu Val Thr Gly Trp Val Leu Val Ser Pro Leu Ser Lys
1               5                   10

<210> SEQ ID NO 21
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ile Thr Val Val Asp Ala Leu His Glu Ile Pro Val Lys
1               5                   10

<210> SEQ ID NO 22
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Leu Val Ala Leu Val Arg
1               5

<210> SEQ ID NO 23
<211> LENGTH: 10
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 23

Asp Trp Val Ser Val Val Thr Pro Ala Arg
1               5                   10

<210> SEQ ID NO 24
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Asp Ser Thr Ile Gln Val Val Glu Asn Gly Glu Ser Ser Gln Gly Arg
1               5                   10                  15

<210> SEQ ID NO 25
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ser Gly Ser Val Ile Asp Gln Ser Arg
1               5

<210> SEQ ID NO 26
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Leu Val Ala Leu Val Lys
1               5

<210> SEQ ID NO 27
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Asp Trp Val Ser Val Val Thr Pro Ala Arg Asp Ser Thr Ile Gln Val
1               5                   10                  15

Val Glu Asn Gly Glu Ser Ser Gln Gly Arg Ser Gly Ser Val Ile Asp
            20                  25                  30

Gln Ser Arg Leu Val Ala Leu Val Arg
        35                  40

<210> SEQ ID NO 28
<211> LENGTH: 10
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Asp Gly Ala Gly Asp Val Ala Phe Val Lys
1               5                   10

<210> SEQ ID NO 29
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ser Ala Ser Asp Leu Thr Trp Asp Asn Leu Lys
1               5                   10

<210> SEQ ID NO 30
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Glu Gly Tyr Tyr Gly Tyr Thr Gly Ala Phe Arg
1               5                   10

<210> SEQ ID NO 31
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Asp Gly Ala Gly Asp Val Ala Phe Val Lys Ser Ala Ser Asp Leu Thr
1               5                   10                  15

Trp Asp Asn Leu Lys Glu Gly Tyr Tyr Gly Tyr Thr Gly Ala Phe Arg
            20                  25                  30

Leu Val Ala Leu Val Arg
        35

<210> SEQ ID NO 32
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Leu Ala Asp Gly Gly Ala Thr Asn Gln Gly Arg
1               5                   10

<210> SEQ ID NO 33
```

```
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ser Asp Leu Ala Val Pro Ser Glu Leu Ala Leu Leu Lys
1               5                   10

<210> SEQ ID NO 34
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Glu Leu Ser Glu Ala Leu Gly Gln Ile Phe Asp Ser Gln Arg
1               5                   10

<210> SEQ ID NO 35
<211> LENGTH: 44
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Leu Ala Asp Gly Gly Ala Thr Asn Gln Gly Arg Ser Asp Leu Ala Val
1               5                   10                  15

Pro Ser Glu Leu Ala Leu Leu Lys Gly Leu Ser Glu Ala Leu Gly Gln
            20                  25                  30

Ile Phe Asp Ser Gln Arg Leu Val Ala Leu Val Arg
            35                  40

<210> SEQ ID NO 36
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Phe Ala Gly Val Phe His Val Glu Lys
1               5

<210> SEQ ID NO 37
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Tyr Gly Phe Ile Glu Gly His Val Val Ile Pro Arg
1               5                   10
```

```
<210> SEQ ID NO 38
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ala Leu Ser Ile Gly Phe Glu Thr Cys Arg
1               5                   10

<210> SEQ ID NO 39
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Phe Ala Gly Val Phe His Val Glu Lys Tyr Gly Phe Ile Glu Gly His
1               5                   10                  15

Val Val Ile Pro Arg Ala Leu Ser Ile Gly Phe Glu Thr Cys Arg Leu
            20                  25                  30

Val Ala Leu Val Arg
        35

<210> SEQ ID NO 40
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Leu Val Asp Gln Asn Ile Phe Ser Phe Tyr Leu Ser Arg
1               5                   10

<210> SEQ ID NO 41
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Val Ser Thr Leu Pro Ala Ile Thr Leu Lys
1               5                   10

<210> SEQ ID NO 42
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Tyr Ser Gln Ala Val Pro Ala Val Thr Glu Gly Pro Ile Pro Glu Val
```

Leu Lys

<210> SEQ ID NO 43
<211> LENGTH: 47
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Leu Val Asp Gln Asn Ile Phe Ser Phe Tyr Leu Ser Arg Val Ser Thr
1               5                   10                  15

Leu Pro Ala Ile Thr Leu Lys Tyr Ser Gln Ala Val Pro Ala Val Thr
            20                  25                  30

Glu Gly Pro Ile Pro Glu Val Leu Lys Leu Val Ala Leu Val Arg
        35                  40                  45

<210> SEQ ID NO 44
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Thr Val Gly Ser Asp Thr Phe Tyr Ser Phe Lys
1               5                   10

<210> SEQ ID NO 45
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Tyr Phe Ile Asp Phe Val Ala Arg
1               5

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Tyr Asn Ser Gln Asn Gln Ser Asn Asn Gln Phe Val Leu Tyr Arg
1               5                   10                  15

<210> SEQ ID NO 47
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Thr Val Gly Ser Asp Thr Phe Tyr Ser Phe Lys Tyr Phe Ile Asp Phe
1               5                   10                  15

Val Ala Arg Tyr Asn Ser Gln Asn Ser Asn Asn Gln Phe Val Leu
            20                  25                  30

Tyr Arg Leu Val Ala Leu Val Arg
        35                  40

<210> SEQ ID NO 48
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Leu Leu Leu Thr Ser Ala Pro Ser Leu Ala Thr Ser Pro Ala Phe Arg
1               5                   10                  15

<210> SEQ ID NO 49
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Tyr Asp Leu Leu Asp Leu Thr Arg
1               5

<210> SEQ ID NO 50
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ser Asp Val Phe Glu Ala Trp Arg
1               5

<210> SEQ ID NO 51
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Leu Leu Leu Thr Ser Ala Pro Ser Leu Ala Thr Ser Pro Ala Phe Arg
1               5                   10                  15

Tyr Asp Leu Leu Asp Leu Thr Arg Ser Asp Val Phe Glu Ala Trp Arg
            20                  25                  30

Leu Val Ala Leu Val Arg
        35

<210> SEQ ID NO 52
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 52

Asn Val Asn Asp Val Ile Ala Pro Ala Phe Val Lys
1               5                   10

<210> SEQ ID NO 53
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 53

Leu Gly Ala Asn Ala Ile Leu Gly Val Ser Leu Ala Ala Ser Arg
1               5                   10                  15

<210> SEQ ID NO 54
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 54

Thr Ala Gly Ile Gln Ile Val Ala Asp Asp Leu Thr Val Thr Asn Pro
1               5                   10                  15
Lys

<210> SEQ ID NO 55
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

Asn Val Asn Asp Val Ile Ala Pro Ala Phe Val Lys Leu Gly Ala Asn
1               5                   10                  15

Ala Ile Leu Gly Val Ser Leu Ala Ala Ser Arg Thr Ala Gly Ile Gln
            20                  25                  30

Ile Val Ala Asp Asp Leu Thr Val Thr Asn Pro Lys Leu Val Ala Leu
        35                  40                  45

Val Arg
    50

<210> SEQ ID NO 56
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 56

Tyr Asp Glu Glu Phe Ala Ser Gln Lys
1               5

<210> SEQ ID NO 57
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

His Phe Thr Tyr Leu Arg
1               5

<210> SEQ ID NO 58
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Ala Trp Thr Asp Val Leu Pro Trp Lys
1               5

<210> SEQ ID NO 59
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Tyr Asp Glu Glu Phe Ala Ser Gln Lys His Phe Thr Tyr Leu Arg Ala
1               5                   10                  15

Trp Thr Asp Val Leu Pro Trp Lys Leu Val Ala Leu Val Arg
            20                  25                  30

<210> SEQ ID NO 60
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Val Ile Phe Tyr Glu Ser His Gly Lys
1               5                   10

<210> SEQ ID NO 61
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 61

Ser Ile Gly Gly Glu Val Phe Ile Asp Phe Thr Lys
1               5                   10

<210> SEQ ID NO 62
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Val Val Gly Leu Ser Thr Leu Pro Glu Ile Tyr Glu Lys
1               5                   10

<210> SEQ ID NO 63
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Gly Val Ile Phe Tyr Glu Ser His Gly Lys Ser Ile Gly Gly Glu Val
1               5                   10                  15

Phe Ile Asp Phe Thr Lys Val Val Gly Leu Ser Thr Leu Pro Glu Ile
            20                  25                  30

Tyr Glu Lys Leu Val Ala Leu Val Arg
            35                  40

<210> SEQ ID NO 64
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Ser Leu Leu Ser Gly Leu Leu Lys
                5
```

ABSOLUTE QUANTITATION OF PROTEINS AND PROTEIN MODIFICATIONS BY MASS SPECTROMETRY WITH MULTIPLEXED INTERNAL STANDARDS

This application claims priority to U.S. Application Ser. No. 61/832,380 filed Jun. 7, 2013 which is expressly incorporated by reference herein in its entirety.

Mass spectroscopy (MS), in conjunction with internal standard peptides labeled with stable heavy isotopes, provides fast, accurate, and precise absolute quantitation of peptides, polypeptides, and proteins in biological and other samples.

The inventive MS method provides target peptide quantitation using multiplexed internal standard isotopologues by high resolution mass spectrometry. The method uses AQUA peptides (WO 03/016861) and/or heavy proteins synthesized with NeuCode amino acids (Hebert et al., Neutron-encoded mass signatures for multiplexed proteome quantification, Nature America, Inc. 2013 Advance Online Publication). In one embodiment, the method is used with TMT assays. In one embodiment, the method is used with universal reporter assays (WO 2012/005838; WO 2012/006406).

SUMMARY OF THE INVENTION

One embodiment is a method for absolute protein or peptide quantitation in a sample by mass spectroscopy (MS) using at least one set of multiplexed heavy peptide internal standards, where each peptide within the set contains the same amino acid sequence, but the peptides within the set differ by a mass defect created by incorporating heavy isotopes on different atoms within at least one amino acid molecule. The heavy peptide internal standards within each set contain the same number of total neutrons within each peptide, but differ in that the heavy atom distribution within the amino acids is unique to each peptide. The heavy peptide internal standards within each set are resolved as a single peak under low resolution mass spectrometry, and are resolved as multiple peaks under high resolution mass spectrometry. The heavy peptide internal standards within each set contain mass differences between each peptide that are less than 1 Dalton. The sample can be a biological sample with the method used for a diagnostic assay. The method can be used in a universal reporter assay. The method can be used for multi-sample analysis. The method can be used for multi-target analysis. The method can be used for multi-sample analysis and multi-target analysis. The heavy peptides are prepared by synthesizing a mixture of at least two peptides with isotopologues of heavy amino acids, resulting in heavy peptides having different mass defects. Isotopologues are prepared by mixing solid phase immobilized AQUA peptide precursors at a defined ratio. The sample is prepared by effecting cleavage of the target protein or peptide. The quantity of the target peptide peak can be obtained by using a standard curve of known quantities of at least two isotopologue standard peptides. The method may be used to verify the target protein or peptide is free of isobaric interference.

One embodiment is a method for protein or peptide quantitation by mass spectroscopy by (a) preparing a sample containing a target protein or peptide of interest for mass spectroscopy analysis, (b) preparing a plurality of heavy isotope labeled peptides having at least one subsequence of the target protein or peptide, (c) mixing the heavy isotope labeled peptides at known concentrations with the sample, (d) subjecting the mixture containing the prepared sample and the heavy isotope labeled peptides to mass spectroscopy analysis at low resolution whereby a single additive heavy peptide mass spectroscopy peak is obtained with the corresponding single light peptide mass spectrometry peak, (e) subjecting the low resolution peaks to high resolution mass spectroscopy analysis whereby a plurality of mass spectroscopy peaks are obtained representing the heavy isotopomeric peptides, (f) generating a light peptide intensity:heavy peptide intensity ratio, and (g) quantifying the intensity of each of the plurality of mass spectroscopy peaks based on the intensity of the heavy isotope labeled peptides to quantify the amount of protein or peptide in the sample. The heavy peptides are prepared by synthesizing a mixture of at least two peptides with isotopologues of heavy amino acids, resulting in heavy peptides having mass defects. Isotopologues are prepared by mixing solid phase immobilized AQUA peptide precursors at a defined ratio. The sample is prepared by effecting cleavage of the target protein or peptide. The quantity of the target peptide peak can be obtained by using a standard curve of known quantities of at least two isotopologue standard peptides. Step (f) can use results from a standard curve for MS analysis. Step (f) can further comprise preparing a plurality of isotopologues of an amino acid; using the isotopologues to generate a set of heavy peptide standards; mixing the plurality of isotopologue-containing peptides at fixed ratios; separating the mixed isotopologue-containing peptides at low mass resolution and high mass resolution; using the low mass resolution to determine the light:heavy peptide ratio; and using the high mass resolution separation results to prepare a standard curve.

One embodiment is a method of peptide isotopologue synthesis where a plurality of precursor amino acid isotopologues, the amino acids containing alpha carboxylate groups, are mixed at a defined ratio with a solid phase peptide synthesis resin containing a coupling group to immobilize the isotopologues through the alpha carboxylate groups. After coupling the precursor amino acid isotopologues, the peptide synthesis resin mixture comprises a plurality of immobilized amino acid isotopologues at known ratios coupled to the resin. The resin comprising the amino acid isotopologues immobilized at known ratios may be further used for peptide synthesis to create a heavy peptide set containing a plurality of isotopologues.

One embodiment is a method of peptide isotopologue synthesis comprising mixing a plurality of precursor amino acid isotopologues with a solid phase peptide synthesis resin containing at least one amino acid already synthesized into a precursor peptide having a desired sequence where the precursor amino acid isotopologues become attached to the N-terminal of the peptides using standard amino acid synthesis procedures. Coupling of the precursor amino acid isotopologues to the immobilized peptide results in a set of heavy peptides containing a known ratio of isotopologue mixture. The resin comprising the amino acid isotopologues immobilized at known ratios can be further used for peptide synthesis to create a heavy peptide set containing a plurality of isotopologues.

One embodiment is a method of protein isotopologue synthesis comprising using a plurality of precursor amino acid isotopologues in an in vitro or cell-based protein expression system to synthesize a protein of interest having a desired sequence where the precursor amino acid isotopologues become incorporated into the protein of interest. Incorporation of the precursor amino acid isotopologues in the expressed protein results in a heavy protein set containing a plurality of isotopologues.

One embodiment is a method of targeted peptide quantitation using multiplexed internal standard peptide isotopologues by high resolution mass spectrometry.

One embodiment is a method of generating a standard curve for mass spectroscopy analysis by preparing a plurality of isotopologues of an amino acid to generate a heavy peptide standard, mixing the plurality of isotopologues at fixed ratios, separating the mixed isotopologues at a low resolution quantitation or a high resolution quantitation, and using the separation results to prepare a standard curve.

One embodiment is a method of targeted peptide quantitation by high resolution mass spectrometry using one or more peptides derived by proteolytic digestion from multiplexed internal standard protein isotopologues.

One embodiment is a method of generating a standard curve for mass spectroscopy analysis by preparing a plurality of isotopologues of an amino acid to generate a heavy protein standard, mixing the plurality of isotopologues at fixed ratios, digesting the isotopologue set with a protease, separating the mixed isotopologues at a low resolution quantitation or a high resolution quantitation, and using the separation results to prepare a standard curve with all peptides derived from the protein isotolopologue set by proteolytic digestion.

One embodiment is a method of generating a standard curve for mass spectroscopy analysis by preparing a plurality of isotopologues of an amino acid to generate a heavy protein standard, mixing the plurality of isotopologues at fixed ratios, digesting the isotopologue set with a protease, and adding one or more distinct isotopically distinct internal standard peptides of known amount, separating the mixed isotopologues at a low resolution quantitation or a high resolution quantitation, and using the separation results to prepare a standard curve with all peptides derived from the protein isotolopologue set by proteolytic digestion, and the distinct isotopic peptide or peptides for absolute quantification of the corresponding peptides of the identical sequence derived by digestion of the native protein and the heavy isotopologue protein set.

One embodiment is a method of synthesizing a single isotopologue set by premixing solid phase immobilized precursor amino acids at a defined desired ratio.

One embodiment is a mass spectrometry analyte quantitation method by (a) preparing, from a sample containing a peptide analyte having a known amino acid sequence, a plurality of heavy isotopologue labeled standards comprising at least part of the analyte sequence; (b) adding a known quantity of the result of step (a) to the sample; (c) cleaving the protein in the sample to result in peptides; (d) quantitating the plurality of heavy isotopologue labeled standards in the sample; and (e) based on the quantitation of (d), determining the quantity of analyte in the sample. Quantitation of the plurality of heavy isotopologue labeled standards in the sample is by high resolution mass spectroscopy. Each standard of step (a) differs from other standards by incorporating heavy atoms of different elements but having the same total number of neutrons. Incorporating different heavy atoms into the standards causes a mass defect among the standards. A peak intensity for the plurality of heavy isotopologue labeled standards contains multiple resolvable peaks under high-resolution MS, each of the multiple resolvable peaks representing the differently labeled standards of the plurality of heavy isotopically labeled standards. The method generates a standard curve using the multiple resolvable peaks as a series of known concentrations of the plurality of heavy isotopologue labeled standards.

One embodiment is a plurality of heavy isotope labeled peptide standards having the same amino acid sequence, each comprising different isotopologues of heavy amino acids, and each having the same nominal mass and chemical formula but different permutations of $^{13}C$—, $^{15}N$—, $^{18}O$—, $^{34}S$—, or $^{2}H$—, to result in peptide standards with milliDalton mass defects. The heavy isotopically labeled peptide standards are used in a mass spectrometry analysis.

One embodiment is a plurality of heavy isotope labeled protein standards having the same amino acid sequence, each comprising different isotopologues of heavy amino acids, and each having the same nominal mass and chemical formula but different permutations of $^{13}C$—, $^{15}N$—, $^{18}O$—, $^{34}S$—, or $^{2}H$—, to result in peptide standards with milliDalton mass defects. The heavy isotopically labeled protein standards are used in a mass spectrometry analysis to quantify every peptide of a given target protein.

One embodiment is a kit for quantifying proteins, polypeptides, or peptides in a sample. The kit comprises a plurality of heavy isotope labeled protein and/or peptide standards having the same amino acid sequence, each comprising different isotopologues of heavy amino acids, and each having the same nominal mass and chemical formula but different permutations of $^{13}C$—, $^{15}N$—, $^{18}O$—, $^{34}S$—, or $^{2}H$—, to result in peptide standards with milliDalton mass defects, and instructions for quantifying the proteins, polypeptides, or peptides in the sample by mass spectroscopy using the kit. The kit may have instructions for using the standards in a multiplex assay. The kit may have instructions for using the standards in a diagnostic assay.

One embodiment is a method for absolute protein or peptide quantitation in a sample by mass spectroscopy using multiplexed heavy peptide internal standards prepared using protected amino acid isotopologues as heavy isotopologue precursors for peptide synthesis. The protected amino acid isotopologues may comprise fluorenylmethyloxycarbonyl (FMOC)-protected heavy isotopologue precursors for peptide synthesis. The method may further include mixing a set of heavy isotopologue peptides at a desired ratio for use as a multiplexed internal standard. The FMOC-protected amino acid precursors are mixed at a defined ratio, and the peptide isotopologue mixture is subsequently synthesized in a single reaction. Mixtures of fluorenylmethyloxycarbonyl (FMOC)-protected isotopologues may be used at a defined ratio in peptide synthesis.

One embodiment is a method for absolute protein or peptide quantitation in a sample by mass spectroscopy using multiplexed heavy protein internal standards prepared using amino acid isotopologues as heavy isotopologue precursors for protein synthesis. The method may further include mixing a set of heavy isotopologue proteins at a desired ratio for use as a multiplexed internal standard. The amino acid precursors are mixed at a defined ratio, and the protein isotopologue mixture is subsequently synthesized in a single reaction. Mixtures of amino acid isotopologues may be used at a defined ratio in protein synthesis.

One embodiment is a method to absolutely quantitate a target protein or peptide in a sample using mass spectroscopy analysis using a standard curve specific for the target protein or peptide in the MS analysis. The method resolves multiplexed internal standard protein and/or peptide isotopologues first with low resolution and subsequently with high resolution. It may be used with a universal reporter assay. The protein or peptide may be used for diagnosis of a medical or physiological condition of a patient over a full dynamic range.

One embodiment is a method to absolutely quantitate a target protein or peptide in a sample using mass spectroscopy analysis and with a standard curve specific for the target protein or peptide in the MS analysis, the standard curve generated from a peptide mixture synthesized with different isotopologues of heavy amino acids resulting in a mass defect of at least 1 mDa in the protein or peptide. The method may further comprise obtaining a single low resolution MS peak, then obtaining a plurality of high resolution peaks, and quantitating an intensity of each isotopologue to quantitate the target protein or peptide in the sample using the standard curve.

One embodiment is a method to absolutely quantitate a target protein or peptide in a sample using mass spectroscopy analysis and with a standard curve specific for the target protein or peptide in the MS analysis, the standard curve generated from a protein mixture synthesized with different isotopologues of heavy amino acids resulting in a mass defect of at least 1 mDa resulting peptides of that protein set from proteolytic digestion. The method may further comprise obtaining a single low resolution MS peak, then obtaining a plurality of high resolution peaks, and quantitating an intensity of each isotopologue to quantitate the target protein or peptide in the sample using the standard curve.

One embodiment is a method of enhancing accuracy and/or sensitivity relative to an AQUA protein or peptide quantitation by mass spectroscopy analysis using more than one peptide isotopologue to generate an internal standard curve containing multiple concentrations of each standard for each assay. The method may further comprise preparing at least three isotopologue sets of heavy target peptides, separating heavy target peptides from light target peptides by MS, at low resolution comparing peaks of the heavy target peptides and light target peptides to determine concentration of the target peptide, and at high resolution resolving isotopologues and analyzing each peak representing different isotopologue concentrations based on the internal standard curve.

One embodiment is a method of enhancing accuracy and/or sensitivity relative to an AQUA protein or peptide quantitation by mass spectroscopy analysis using more than one protein isotopologue to generate an internal standard curve containing multiple concentrations of each standard for each corresponding peptide of the native protein analyte. The method may further comprise preparing at least two isotopologue sets of heavy target proteins, separating heavy target peptides from light target peptides by MS, at low resolution comparing peaks of the heavy target peptides and light target peptides to determine concentration of the target peptides, and at high resolution resolving isotopologues and analyzing each peak representing different isotopologue concentrations based on the internal standard curve.

One embodiment is a method of generating a standard curve for mass spectroscopy analysis based on mass defects. The method comprises preparing a plurality of isotopologues of amino acids to generate a heavy peptide standard, mixing the plurality of isotopologues at a fixed desired ratio, separating the mixed isotopologues with low resolution MS or with high resolution MS, then using results of the separation to prepare a standard curve. Separation may be by LC-MS and the standard curve may be prepared with intact ions. Separation may be by LC-MSn and the standard curve may be prepared with fragment ions. The method may be used to verify the target protein or peptide is free of isobaric interference.

One embodiment is a method of generating a standard curve for mass spectroscopy analysis based on mass defects. The method comprises preparing a plurality of isotopologues of amino acids to generate a heavy peptide standard, mixing the plurality of isotopologues at a fixed desired ratio, separating the mixed isotopologues with low resolution MS or with high resolution MS, then using results of the separation to verify the MS calibration.

One embodiment is a method of generating a standard curve for mass spectroscopy analysis based on mass defects. The method comprises preparing a plurality of isotopologues of amino acids to generate a heavy peptide standard, mixing the plurality of isotopologues at a fixed desired ratio, separating the mixed isotopologues with low resolution MS or with high resolution MS, then using results of the separation to verify the mass shift of the target analyte.

One embodiment is a mass spectrometry quantitation method comprising (a) preparing a plurality of protein isotopologues, (b) preparing a heavy peptide internal standard, (c) spiking (a) and (b) into a target sample, (d) digesting the target sample (c), (e) quantifying each corresponding light:heavy peptide derived from the digestion of the native target protein analyte (c) and heavy protein isotopologues (a), (f) separating the peptides by MS analysis, and (g) quantifying the light and heavy peptide isotopologues with the heavy peptide internal standard (b) to quantify the target analyte peptide using the internal standard and all corresponding light:heavy isotopologue peptide pairs from the target and internal standard protein set.

One embodiment is a mass spectrometry quantitation method comprising (a) preparing a plurality of mass tag isotopologues, (b) preparing a peptide internal standard labeled with the mass tag isotopologues, (c) spiking (a) and (b) into a target sample, (d) digesting the target sample (c), (e) labeling the target sample and resulting universal reporter peptide with the light version of the tag, (f) separating the peptides by MS analysis, and (g) quantifying the target analyte using the internal standard.

BRIEF DESCRIPTION OF THE DRAWINGS

FIGS. 7a-b show the 37 possible formulas and masses of arginine +6 Da isotopologues with seven 6 mDa-spaced representative isotopologues (boxed, FIG. 7a) and the 86 possible formulas and masses of arginine +10 Da isotopologues with seven 6 mDa-spaced representative isotopologues (boxed, FIG. 7b).

FIG. 12 schematically shows a configuration for a peptide to be quantified linked to a reporter peptide and correlated to a universal peptide U, each to be labeled with one or more heavy amino acids or heavy amino acid isotopologues.

Figure 1:
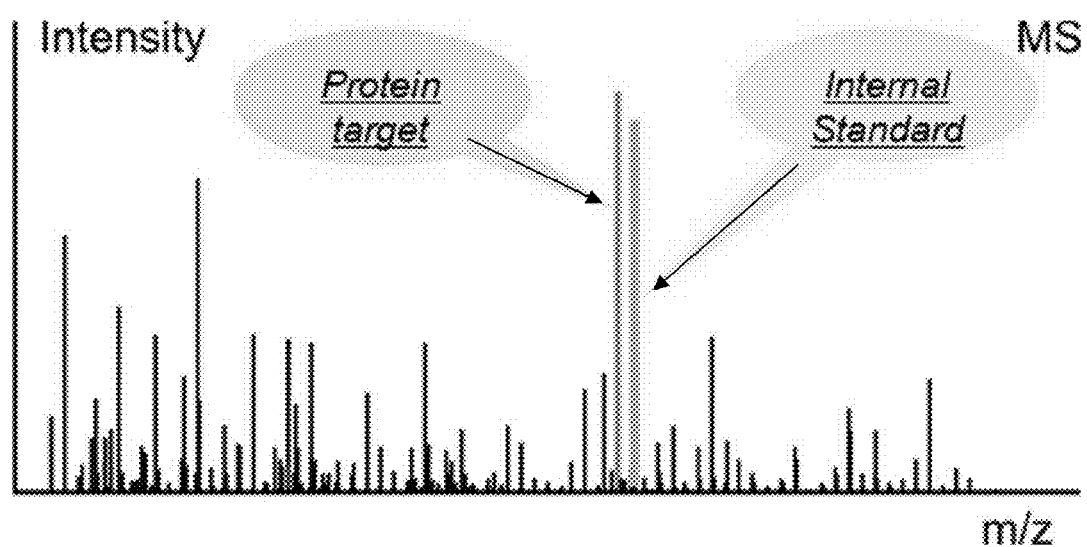
FIG. 1 shows mass spectrometry (MS) quantitation of a protein target using an internal standard.

Embodiments of the invention follow.

A method for absolute quantitation of a target protein or peptide in a sample by mass spectroscopy (MS) by preparing internal standard isotopologues using at least one set of multiplexed heavy peptide internal standards, where each peptide within the at least one set contains the same amino acid sequence, but the peptides within the set differ by a mass defect created by incorporating heavy isotopes on different atoms within at least one amino acid molecule resulting in internal standard isotopologues, and quantitating at least one target protein or peptide using the multiplexed internal standard isotopologues. In one embodiment the heavy peptide internal standards within each set contain the same number of total neutrons within each peptide, but differ in that the heavy atom distribution within the amino acids is unique to each peptide. In one embodiment the heavy peptide internal standards within each set are resolved as a single peak under low resolution mass spectrometry, and are resolved as multiple peaks under high resolution mass spectrometry. In one embodiment the heavy peptide internal standards within each set contain mass differences between each peptide that are less than 1 Dalton. In one embodiment the sample is a biological sample and the method is used for a diagnostic assay. In one embodiment the method is used in a universal reporter assay. In one embodiment the method is used for multi-sample analysis. In one embodiment the method is used for multi-target analysis. In one embodiment the method is used for multi-sample analysis and multi-target analysis. In one embodiment the heavy peptides are prepared by synthesizing a mixture of at least two peptides with isotopologues of heavy amino acids, resulting in heavy peptides having mass defects. In this embodiment the isotopologues are prepared by mixing solid phase immobilized AQUA peptide precursors at a defined ratio. In this embodiment the sample is prepared by effecting cleavage of the target protein or peptide. In one embodiment the method is used to verify the target protein or peptide is free of isobaric interference.

A method for protein or peptide quantitation by mass spectroscopy by (a) preparing a sample containing a target protein or peptide of interest for mass spectroscopy analysis, (b) preparing a plurality of heavy isotope labeled peptides having at least one subsequence of the target protein or peptide, (c) mixing the heavy isotope labeled peptides at known concentrations with the sample, (d) subjecting the mixture containing the prepared sample and the heavy isotope labeled peptides to mass spectroscopy analysis at low resolution whereby a single additive heavy peptide mass spectroscopy peak is obtained with the corresponding single light peptide mass spectrometry peak, (e) subjecting the low resolution peaks to high resolution mass spectroscopy analysis whereby a plurality of mass spectroscopy peaks are obtained representing the heavy isotopomeric peptides, (f) generating a light peptide intensity:heavy peptide intensity ratio, and (g) quantifying the intensity of each of the plurality of mass spectroscopy peaks based on the intensity of the heavy isotope labeled peptides to quantify the amount of protein or peptide in the sample. In one embodiment the heavy peptides are prepared by synthesizing a mixture of at least two peptides with isotopologues of heavy amino acids, resulting in heavy peptides having mass defects. In this embodiment the isotopologues are prepared by mixing solid phase immobilized AQUA peptide precursors at a defined ratio. In this embodiment the sample is prepared by effecting cleavage of the target protein or peptide. In one embodiment step (f) uses results from a standard curve for MS analysis. In this embodiment the method further comprises preparing a plurality of isotopologues of an amino acid; using the isotopologues to generate a set of heavy peptide standards; mixing the plurality of isotopologue-containing peptides at fixed ratios; separating the mixed isotopologue-containing peptides at low mass resolution and high mass resolution; using the low mass resolution to determine the light:heavy peptide ratio; and using the high mass resolution separation results to prepare a standard curve. In one embodiment the quantity of the target peptide peak is obtained by using a standard curve of known quantities of at least two isotopologue standard peptides.

A method of peptide isotopologue synthesis where a plurality of precursor amino acid isotopologues, the amino acids containing alpha carboxylate groups, are mixed at a defined ratio with a solid phase peptide synthesis resin containing a coupling group to immobilize the isotopologues through the alpha carboxylate groups. In one embodiment, after coupling the precursor amino acid isotopologues, the peptide synthesis resin mixture comprises a plurality of immobilized amino acid isotopologues at known ratios coupled to the resin. In this embodiment the resin comprising the amino acid isotopologues immobilized at known ratios is further used for peptide synthesis to create a heavy peptide set containing a plurality of isotopologues.

A method of peptide isotopologue synthesis by mixing a plurality of precursor amino acid isotopologues with a solid phase peptide synthesis resin containing at least one amino acid already synthesized into a precursor peptide having a desired sequence where the precursor amino acid isotopologues become attached to the N-terminal of the peptides using standard amino acid synthesis procedures. In one embodiment coupling of the precursor amino acid isotopologues to the immobilized peptide results in a set of heavy peptides containing a known ratio of isotopologue mixture. In one embodiment the resin comprising the amino acid isotopologues immobilized at known ratios is further used for peptide synthesis to create a heavy peptide set containing a plurality of isotopologues.

A method of targeted peptide quantitation using multiplexed internal standard peptide isotopologues by high resolution mass spectrometry.

A method of generating a standard curve for mass spectroscopy (MS) analysis by preparing a plurality of isotopologues of an amino acid to generate a heavy peptide standard, mixing the plurality of isotopologues at fixed ratios, separating the mixed isotopologues at a low resolution quantitation or a high resolution quantitation, and using the separation results to prepare a standard curve.

A method of synthesizing a single isotopologue set by premixing solid phase immobilized precursor amino acids at a defined desired ratio.

A MS analyte quantitation method comprising (a) preparing, from a sample containing a peptide analyte having a known amino acid sequence, a plurality of heavy isotopologue labeled standards comprising at least part of the analyte sequence; (b) adding a known quantity of the result of step (a) to the sample; (c) cleaving the protein in the sample to result in peptides; (d) quantitating the plurality of heavy isotopologue labeled standards in the sample; and (e) based on the quantitation of (d), determining the quantity of analyte in the sample. In one embodiment quantitation of the plurality of heavy isotopologue labeled standards in the sample is by high resolution mass spectroscopy. In one embodiment each standard of step (a) differs from other standards by incorporating heavy atoms of different elements but having the same total number of neutrons. In this embodiment incorporating different heavy atoms into the standards causes a mass defect among the standards. In one embodiment a peak intensity for the plurality of heavy isotopologue labeled standards contains multiple resolvable peaks under high-resolution MS, each of the multiple resolvable peaks representing the differently labeled standards of the plurality of heavy isotopically labeled standards. In this embodiment a standard curve is generated using the multiple resolvable peaks as a series of known concentrations of the plurality of heavy isotopologue labeled standards.

A plurality of heavy isotope labeled peptide standards having the same amino acid sequence, each comprising different isotopologues of heavy amino acids, and each having the same nominal mass and chemical formula but different permutations of $^{13}C-$, $^{15}N-$, $^{18}O-$, $^{34}S-$, or $^{2}H-$, to result in peptide standards with milliDalton mass defects. The plurality of heavy isotopically labeled peptide standards are used in a mass spectrometry analysis.

A kit for quantifying proteins, polypeptides, or peptides in a sample, the kit comprising a plurality of heavy isotope labeled peptide standards having the same amino acid sequence, each comprising different isotopologues of heavy amino acids, and each having the same nominal mass and chemical formula but different permutations of $^{13}C-$, $^{15}N-$, $^{18}O-$, $^{34}S-$, or $^{2}H-$, to result in peptide standards with milliDalton mass defects, and instructions for quantifying the proteins, polypeptides, or peptides in the sample by mass spectroscopy using the kit. In one embodiment the instructions are for using the standards in a multiplex assay. In one embodiment the instructions are for using the standards in a diagnostic assay.

A method for absolute protein or peptide quantitation in a sample by mass spectroscopy (MS) using multiplexed heavy peptide internal standards prepared using protected amino acid isotopologues as heavy isotopologue precursors for peptide synthesis. In one embodiment the protected amino acid isotopologues comprise fluorenylmethyloxycarbonyl (FMOC)-protected heavy isotopologue precursors for peptide synthesis. In one embodiment the method further comprises mixing a set of heavy isotopologue peptides at a desired ratio for use as a multiplexed internal standard. In one embodiment the method further comprises mixing a plurality of the FMOC-protected amino acid precursors at a defined ratio, and subsequently synthesizing the peptide isotopologue mixture in a single reaction. In one embodiment mixtures of fluorenylmethyloxycarbonyl (FMOC)-protected isotopologues at a defined ratio are used in peptide synthesis.

A method to absolutely quantitate a target protein or peptide in a sample using mass spectroscopy (MS) analysis using a standard curve specific for the target protein or peptide in the MS analysis, by resolving multiplexed internal standard peptide isotopologues first with low resolution and subsequently with high resolution. In one embodiment the method is used with a universal reporter assay. In one embodiment the protein or peptide is used for diagnosis of a medical or physiological condition of a patient over a full dynamic range.

A method to absolutely quantitate a target protein or peptide in a sample using mass spectroscopy (MS) analysis and with a standard curve specific for the target protein or peptide in the MS analysis, the standard curve being generated from a peptide mixture synthesized with different isotopologues of heavy amino acids resulting in a mass defect of at least 1 mDa in the protein or peptide. In one embodiment the method further comprises obtaining a single low resolution MS peak, then obtaining a plurality of high resolution peaks, and quantitating an intensity of each isotopologue to quantitate the target protein or peptide in the sample using the standard curve.

A method of enhancing at least one of accuracy and/or sensitivity relative to an AQUA protein or peptide quantitation by mass spectroscopy (MS) analysis by using more than one peptide isotopologue to generate an internal standard curve containing multiple concentrations of each standard for each assay. In one embodiment the method further comprises preparing at least three isotopologue sets of heavy target peptides, separating heavy target peptides from light target peptides by MS, at low resolution comparing peaks of the heavy target peptides and light target peptides to determine concentration of the target peptide, at high resolution resolving isotopologues and analyzing each peak representing different isotopologue concentrations based on the internal standard curve.

A method of generating a standard curve for mass spectroscopy (MS) analysis based on mass defects by preparing a plurality of isotopologues of amino acids to generate a heavy peptide standard, mixing the plurality of isotopologues at a fixed desired ratio, separating the mixed isotopologues with low resolution MS or with high resolution MS, then using results of the separation to prepare a standard curve. In one embodiment separation is by LC-MS and the standard curve is prepared with intact ions. In one embodiment separation is by LC-MSn and the standard curve is prepared with fragment ions. In one embodiment the method is used to verify the target protein or peptide is free of isobaric interference.

A method of generating a standard curve for mass spectroscopy (MS) analysis based on mass defects by preparing a plurality of isotopologues of amino acids to generate a heavy peptide standard, mixing the plurality of isotopologues at a fixed desired ratio, separating the mixed isotopologues with low resolution MS or with high resolution MS, then using results of the separation to verify the MS calibration.

A method of generating a standard curve for mass spectroscopy (MS) analysis based on mass defects by preparing a plurality of isotopologues of amino acids to generate a heavy peptide standard, mixing the plurality of isotopologues at a fixed desired ratio, separating the mixed isotopologues with low resolution MS or with high resolution MS, then using results of the separation to verify the mass shift of the target analyte.

A MS quantitation method comprising (a) preparing a plurality of mass tag isotopologues, (b) preparing a peptide internal standard labeled with the mass tag isotopologues, (c) spiking (a) and (b) into a target sample, (d) digesting the target sample (c), (e) labeling the target sample and resulting universal reporter peptide with the light version of the tag, (f) separating the peptides by MS analysis, and (g) quantifying the target analyte using the internal standard.

A mass spectrometry (MS) quantitation system comprising a sample prepared for MS quantitation, a plurality of mass tag isotopologues, an ion source, a mass analyzer with isotopologue separation, and a detector with isotopologue peptide internal standard resolution.

The method extends the ability of the known AQUA method, and results in enhanced quantitation accuracy by generation of a standard curve, which allows both low mass resolution and high mass resolution (generally >100,000) capability. The method extends the ability of the known AQUA method, and results in enhanced quantitation accuracy by generation of a standard curve for all peptides in a target protein and enabling the identification and quantitation of one or more peptides of the target protein that are regulated differentially from the overall protein level, such as through post-translational regulation or modification. The inventive method advantageously uses mass defects, disclosed in Hebert et al., Neutron-encoded mass signatures for multiplexed proteome quantification, Nature America, Inc. 2013 Advance Online Publication), which is expressly incorporated herein by reference in its entirety, to obtain a single mass spectroscopy peak at low resolution, then subsequently resolves additional peaks at high resolution to quantify the intensity of each isotopologue that results when a mixture of two or more peptides is synthesized with different isotopologues of heavy isotope labeled amino acids as the standard. The resulting heavy isotope labeled peptides, termed heavy peptides, have the same nominal mass and chemical formula, but have different permutations of $^{13}C-$, $^{15}N-$, $^{18}O-$, $^{34}S-$, or $^{2}H-$, resulting in peptides with milliDalton mass defects.

A single isotopologue peptide set is obtained by premixing amino acid isotopomer precursors or solid phase immobilized AQUA peptide amino acid isotopomer precursors at a defined desired ratio, as subsequently explained. A full response curve can be generated for either low or high resolution quantitation.

A single isotopologue protein set is obtained by premixing amino acid isotopomer precursors at a defined desired ratio, as subsequently explained. A full response curve for every peptide of the target protein can be generated for either low or high resolution quantitation.

The method extends the ability of the known AQUA method, and results in enhanced quantitation accuracy by generation of a standard curve in with high resolution measurement for one or more peptides of the target protein.

The inventive process thus results in enhanced accuracy, which is particularly required for diagnostic mass spectroscopy assays. The invention also discloses methods of protein and peptide isotopologue synthesis, the use of proteotypic peptide isotopologue sets concatenated with a reporter peptide and quantified with a universal reporter standard peptide, the use of a heavy isotopologue protein standard set, and methods of targeted peptide quantitation using multiplexed internal standard peptide isotopologues by high resolution mass spectrometry.

Absolute protein quantitation uses one or more spiked internal standard peptides containing heavy stable isotopes, with the amino acid sequence of the standard peptides corresponding to a subsequence or subsequences of the target protein to be assayed. The absolute quantitation of this target protein depends upon the accuracy and linearity of responses of the spiked internal standard.

The known AQUA method provides quantitative analysis of proteins during MS analysis using a single labeled peptide as an internal standard to quantify the amount of the target, i.e., the amount of the corresponding target unlabeled peptide or protein in a sample. This is shown in FIG. 1.

AQUA relies on a spike of one peptide standard, so quantitation of the target peptide or protein depends on the accuracy of that one spiked peptide. The quantitation assumes a response factor of 1, and assumes that the analyte is within the linear range. Neither assumption may be accurate for any particular assay and/or particular analyte. The lack of an internal standard curve with each measurement results in high coefficients of variation (CV) and a limited dynamic range at both inter-assay and inter-laboratory levels.

Figure 2:
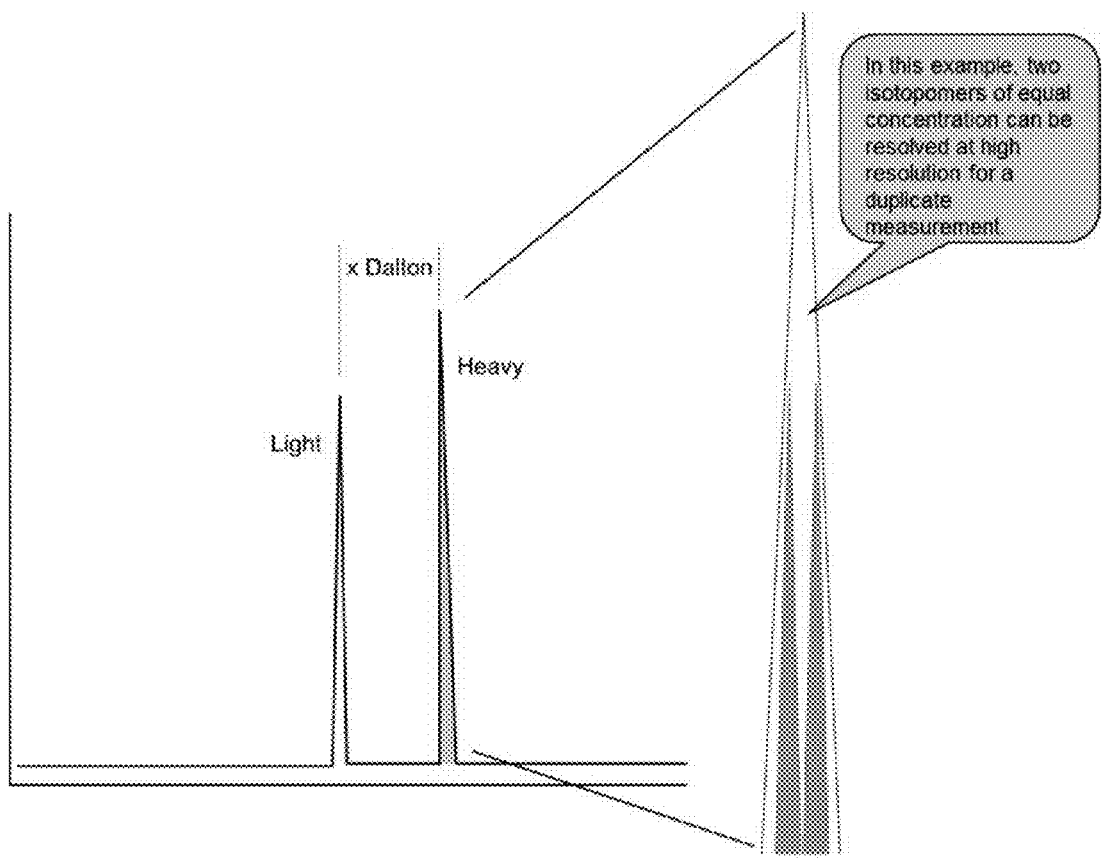
FIG. 2 shows low resolution MS and high resolution MS of two isotopomers (chemical isomers with different heavy isotopic atoms such that the isomers have the same unit mass but differ in isotopic elements).
Figure 3:
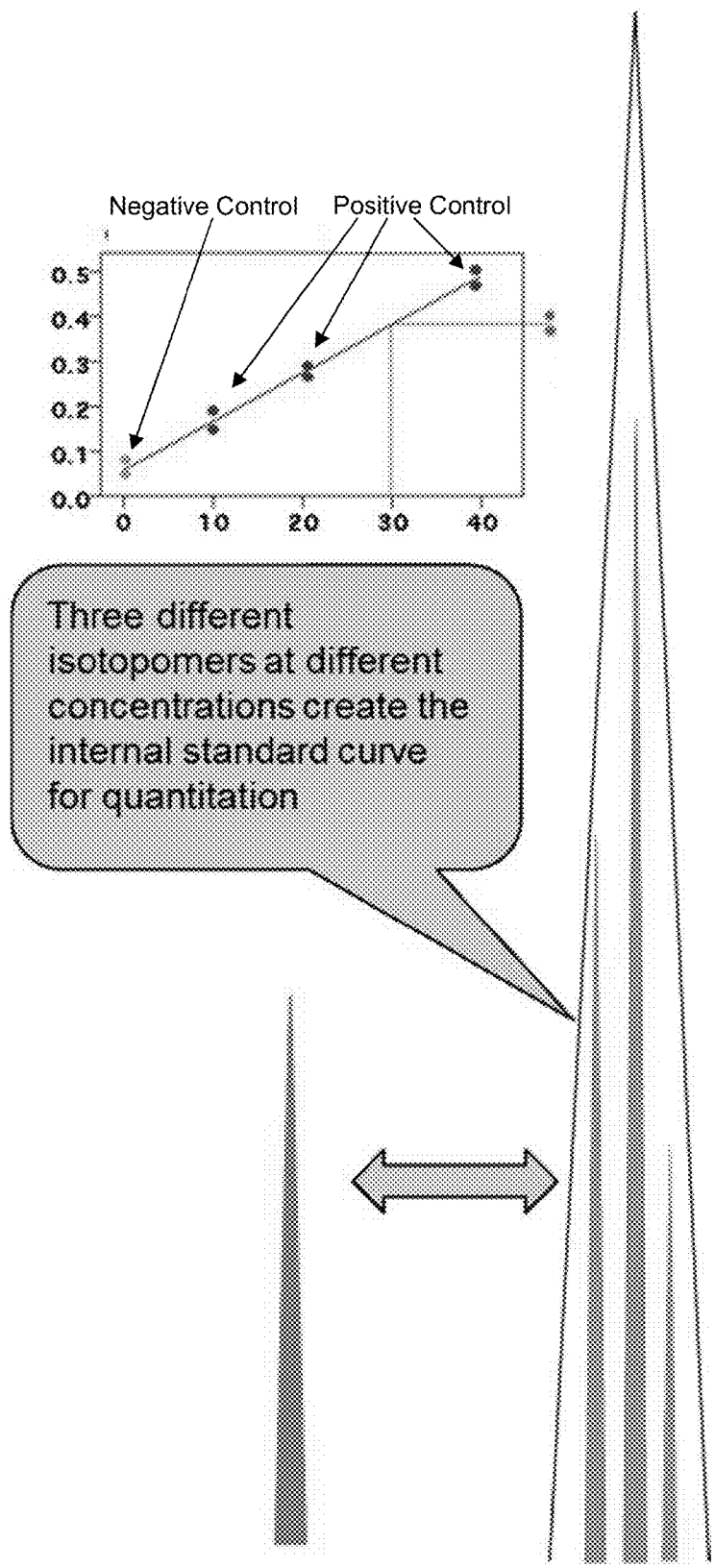
FIG. 3 shows the generation of a standard curve at high MS resolution with three different isotopomers at different concentrations.

The inventive method thus extends the capability of AQUA to provide greater quantitation accuracy by using multiple concentrations of each standard to form an internal standard curve, henceforth referred to as AQUAplex. AQUAplex uses isotopically labeled peptide families, where each member of the family differs from other members by incorporation of isotopologues, i.e., heavy atoms of different elements, but having the same total number of neutrons. AQUAplex heavy peaks represent a family of isotopically labeled peptides that are separated and quantified by low mass resolution and high mass resolution. A single composite peak that is more readily detectable is obtained in low-resolution MS; thus, AQUAplex allows quantitation at the MS1 level. Multiple AQUAplex isotopologue component peaks are obtained and quantified in high-resolution MS. The use of multiple heavy isotopologues increases assay accuracy by using multiple measurements, e.g., light:heavy peptide intensity ratios obtained first with low resolution, then quantified with a heavy internal standard isotopologue set with high resolution MS. As shown in FIG. 1, in a low resolution MS1 analysis, the heavy peak, which contains multiple isotopologues, is seen as a single peak and the peak height and area are the sum of the isotopologues making up the mixture. The sum of the different isotopologue concentrations appears in the mass spectrum as a more intense signal than the individual isotopologues, and may be more intense than the signal of the target light peptide being analyzed. In this way, under low resolution MS analysis the heavy peak functions as a marker or "sign post" for the presence of the target peptide peak which occurs at a lower m/z position in the spectrum. Because it is known precisely what the mass increase of the heavy peak is, the target peak position and elution time can be accurately identified during LC-MS or LC-MS/MSn, even if the target peak is of low intensity and may be somewhat lost in the noise or background of the MS spectrum. Thus, the method facilitates the analysis and more accurate quantitation of peptides of lower concentration that may not be immediately detected or may not be detected at all by the mass spectrometer. The low resolution comparison of the heavy and light peptide peaks can provide an initial determination of the concentration of the target peptide being analyzed. Next, under high resolution analysis of the heavy peak, the isotopologues are resolved and each peak representing the different concentrations of the isotopologues making up the internal standard curve can be analyzed (FIG. 2). The relative concentrations of these isotopologues can be used to create an internal standard curve to accurately determine the concentration of the target light peptide peak (FIG. 3). The high resolution required to resolve the isotopologues also resolves the target analyte from interfering species, which improves the target signal-to-noise, sensitivity, and quantitative accuracy. The isotopologue peak pattern and absolute masses can be used to verify that the correct heavy peptide internal standard is being used as the internal standard, and the exact masses of these isotopologues can be used as mass calibrants to enable absolute measurements of the offsets for the light target peptide. Thus, the inventive method permits accurate identification and absolute quantification of target peptides, that is, it provides greater accuracy and at higher sensitivity than possible using previous AQUA peptide techniques.

As shown in FIG. 2, the AQUAplex heavy peaks represent a family of peptides, with a single peak resulting with low resolution MS analysis, and multiple peaks resulting with high resolution analysis (two peaks shown in FIG. 2). The AQUA light and heavy peptide peaks are separated by the number of heavy isotopes incorporated into the amino acids (shown in FIG. 2 as x Dalton). The heavy peak is used as a control to determine the concentration of the light peptide. In this example, at low resolution a measurement of the absolute concentration of the target peptide can be determined with the higher mass internal standard peak, and the two isotopomers of equal concentration are able to be resolved at high resolution for a duplicate measurement. These low and high resolution measurements may be performed with MS1 to quantify the parent masses, or MSn to verify and quantify the fragment ions at either low or high resolution.

On mass spectrometers capable of multiple ion isolation and high resolution scanning, such as the Q Exactive hybrid mass spectrometer (Thermo Scientific), multiplexed analysis of peptides may be performed by isolation and storage of multiple light:heavy sets or mass ranges of ions prior to high resolution scanning. Thus, multiplexed quantitation at low and high resolution can be performed more efficiently with improved duty cycle performance (Michalski et al. (2011). Mass Spectrometry-based Proteomics Using Q Exactive, a High-performance Benchtop Quadrupole Orbitrap Mass Spectrometer, Mol Cell Proteomics 2011 September; 10(9): M111.011015).

The sample is prepared for MS analysis as known in the art, e.g., subjecting the sample peptide to proteolytic cleavage. The sample and standard are then analyzed by mass spectroscopy at low mass resolution whereby a single additive mass spectroscopy peak is obtained from the standard, then analyzed at high mass resolution (>100,000) wherein a plurality of mass spectroscopy peaks are obtained. The quantity of each peak is obtained using an internal standard, that is, by comparison to a peak intensity of a known quantity of an isotopologue standard peptide, or with reference to an external standard using known quantities of at least two isotopologue standard peptides to generate a standard curve (FIG. 3). Use of a standard curve enhances quantitation across a dynamic range of analyte.

One embodiment of the method is generating a standard curve for MS analysis. The method comprises the following steps: preparing a plurality of isotopologues of an amino acid to generate a heavy peptide standard; mixing the plurality of isotopologues at fixed ratios; then separating the mixed isotopologues at a low mass resolution or a high mass resolution using LC-MS or LC-MSn; then using the separation results to prepare a standard curve with the intact or fragment ions, respectively.

Figure 4:
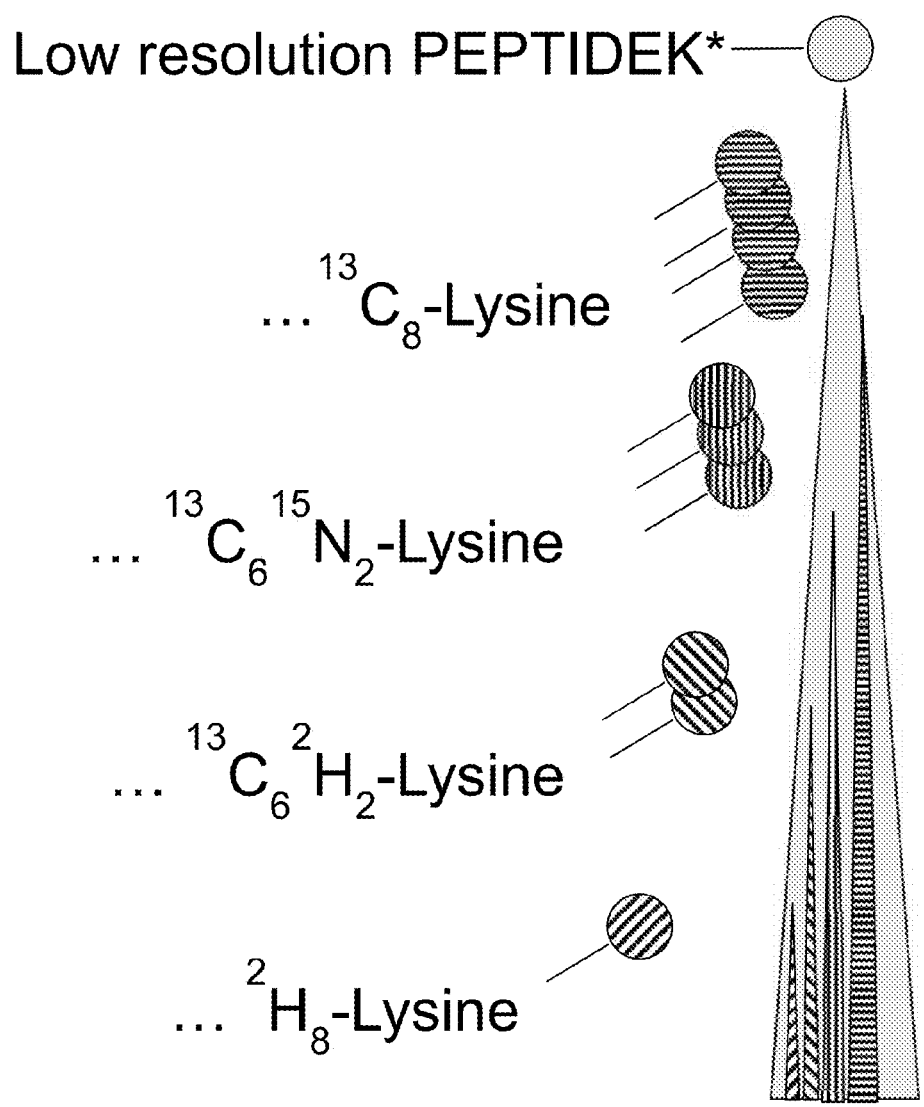
FIG. 4 schematically illustrates synthesis of internal standards using a defined mixture of precursor amino acid isotopologues in solution or immobilized on solid supports.

One embodiment is a method for absolute protein or peptide quantitation by MS with multiplexed internal standards. Heavy AQUAplex peptides, used as standards for assay of a sample containing a target peptide or protein, are prepared by synthesizing a mixture of at least two peptides with isotopologues of heavy amino acids, resulting in heavy peptides having mass defects, as subsequently explained. The heavy peptides have at least one subsequence of the target or analyte. The set of heavy isotopologue peptides is then mixed at a desired ratio for use as a multiplexed internal standard. Alternatively, the set of isotopologues is prepared by mixing fluorenylmethyloxycarbonyl (FMOC)-protected amino acid precursors in solution or solid phase-immobilized AQUA peptide precursors at a defined ratio, and then synthesizing the peptide isotopologue mixture in a single reaction (FIG. 4).

Figure 5:
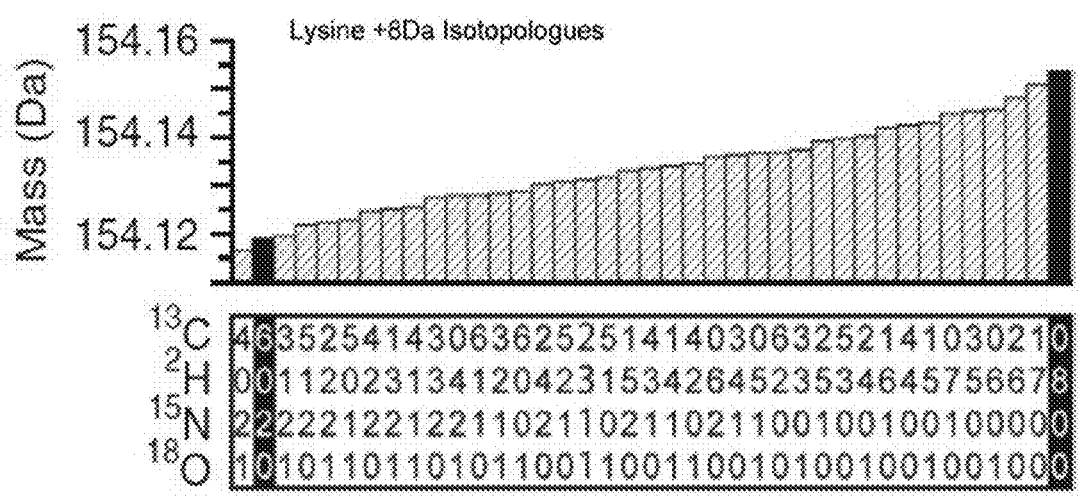
FIG. 5 shows possible heavy isotope combinations and masses of lysine +8 Da isotopologues, with two commercially available isotopologues (filled black, from Hebert et al. 2013).
Figure 6:
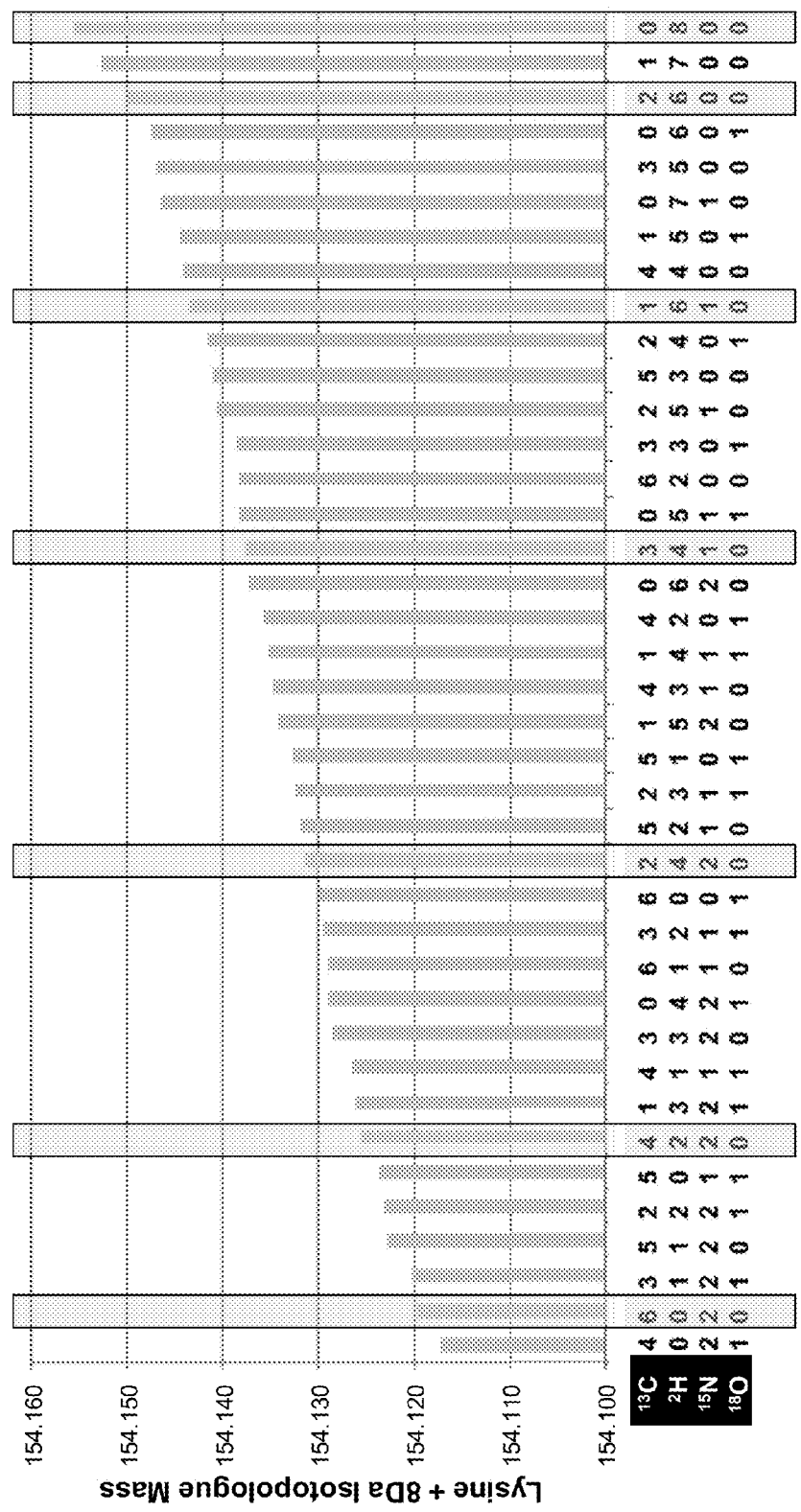
FIG. 6 shows the 39 possible formulas and masses of lysine +8 Da isotopologues with seven 6 milliDalton (mDa)-spaced representative isotopologues (boxed).
Figure 7A:
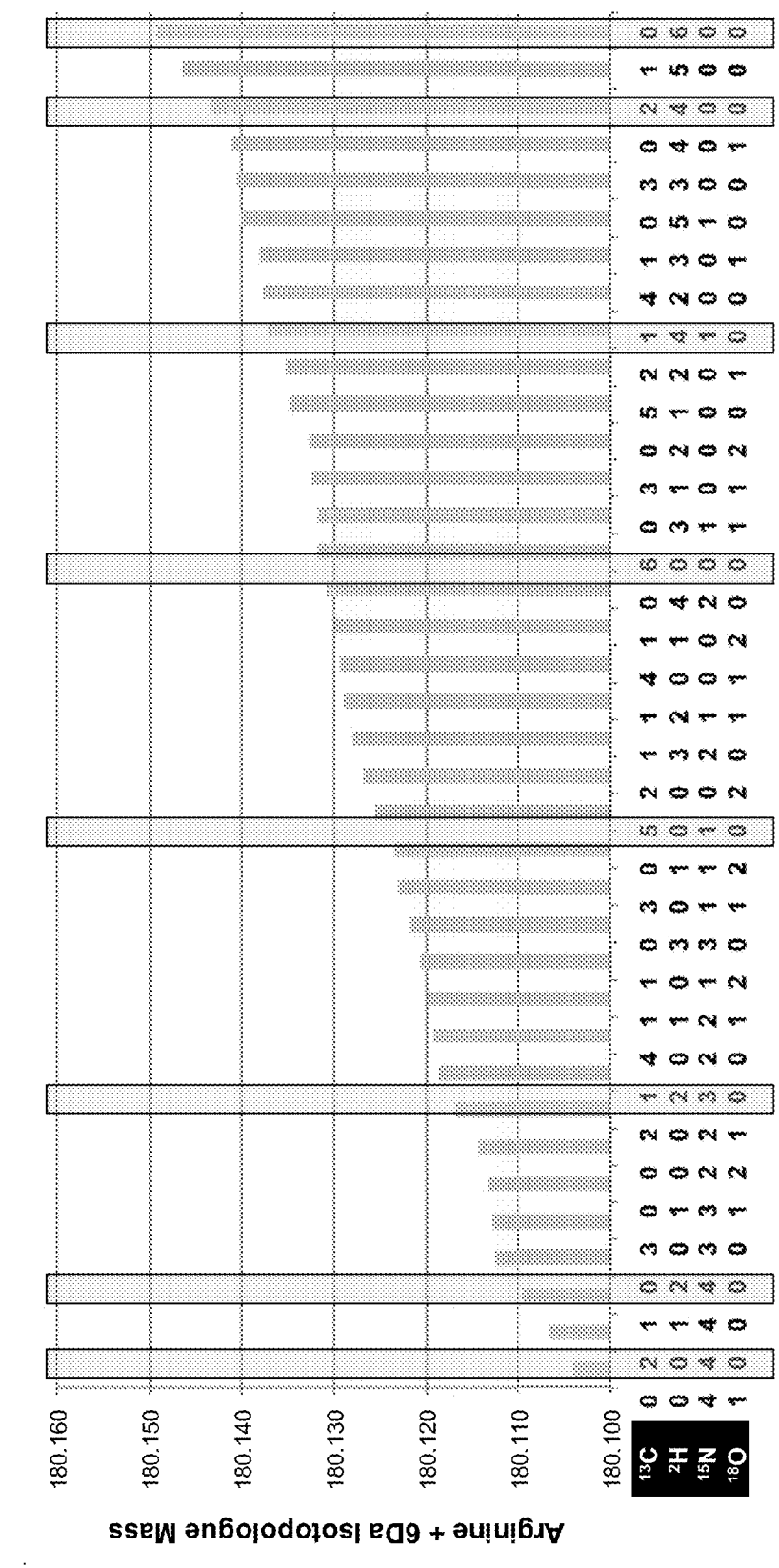
Figure 8:
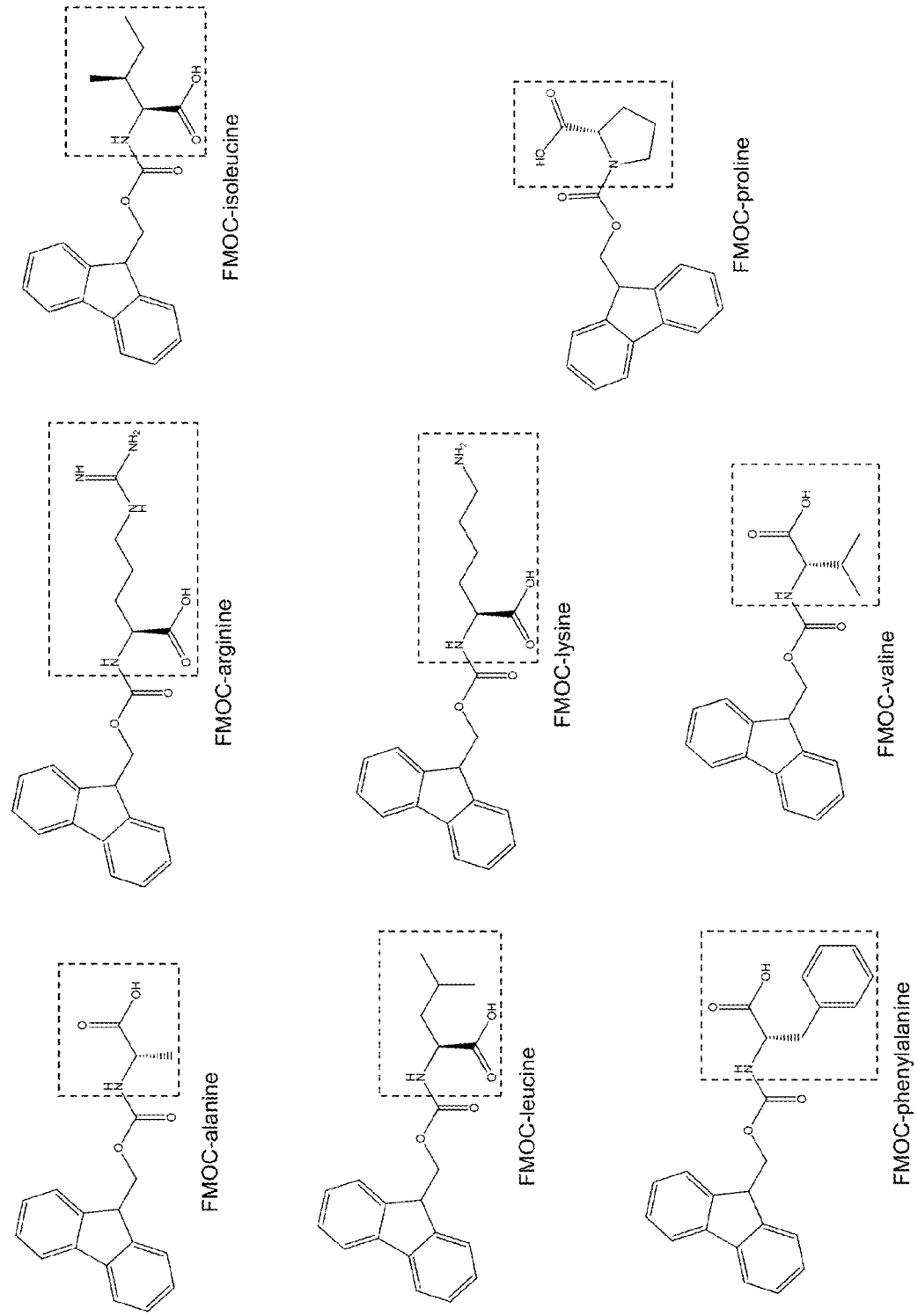
FIG. 8 shows the chemical structures of nine representative fluorenylmethyloxycarbonyl (FMOC)-protected amino acids that may be used as heavy isotopologue precursors for peptide synthesis by isotopic labeling in the boxed region.

For AQUAplex assays, each member of the family differs from the other members by incorporation of heavy atoms of different elements, but having the same total number of neutrons. For example, there are 39 unique isotopologues of lysine +8 Da spanning a mass range of 36 mDa. Theoretically each of these can be resolved by sufficiently high resolution mass spectrometry (FIG. 5). The solid bars represent two different isotopologues that are commercially available (Cambridge Isotope Laboratories). One of the lysine isomers contains six $^{13}C$ atoms and two $^{15}N$ atoms in its structure, while the other one contains eight $^{2}H$ atoms. Both amino acids are nominally of the same molecular mass (about 154.1 Da) but they differ in their accurate mass by 36 mDa due to the mass defect differences between the neutrons associated with carbon atoms and hydrogen atoms. Under high resolution mass spectroscopy analysis, peptides made from these two lysine isotopologues can be resolved into two distinct peaks differing in mass by the associated mass defects. Other peptides may be designed to contain heavy atoms at different sites within their structures. In one embodiment, one peptide may contain one or more $^{13}C$-lysine amino acids, while another peptide may contain an equal number of $^{15}N$-, $^{18}O$-, $^{34}$S-, or $^2$H-lysine amino acids. The incorporation of different heavy atoms between the members of the family causes a mass defect to occur between peptides, which slightly alters the exact mass by mDa. With sufficiently high MS resolution, more isotopologues that are closer in mass can be resolved. In one embodiment, seven isotopologues of FMOC-protected lysine+8 Da that are separated by at least 6 mDa can be used to synthesize and be mixed at a defined ratio of internal standard isotopologues (FIG. 6). This extended mixture can be used with high resolution MS to create a standard curve across a dynamic range greater than one order of magnitude for more accurate quantitation of a target peptide that varies widely in concentration. Similarly, eight isotopologues of arginine+6 Da that are separated by greater than 6 mDa and eight isotopologues of arginine+10 Da that are separated by greater than 6 mDa can be used to synthesize and create a defined mixture of heavy internal standard isotopologues using FMOC-protected arginine+6 Da and FMOC-protected arginine+10 Da (FIGS. 7a-b). Higher resolution MS or MSn can be used to further increase the number of resolvable isotopomers that can be combined to create a standard curve for the heavy internal standard peptide mixture and improve quantitative accuracy and dynamic range of quantitation. In one embodiment, isotopologues are from one or more of the set of FMOC-protected alanine, arginine, isoleucine, leucine, lysine, phenylalanine, proline, and valine (FIG. 8).

Figure 10:
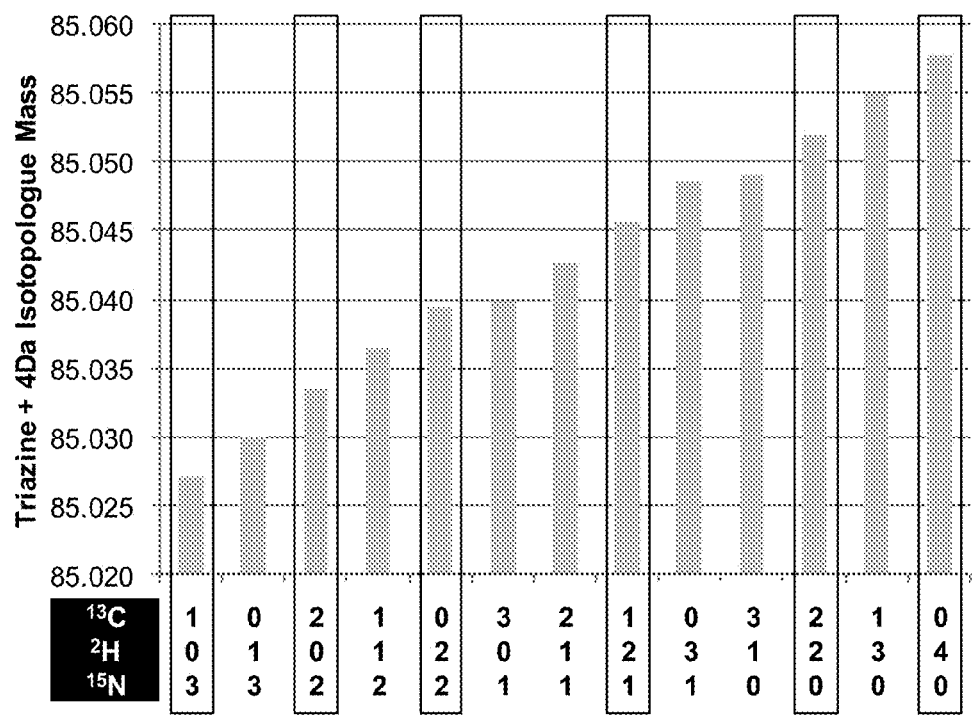
FIGS. 10a-b show the 13 possible isotopologues of the triazine core (FIG. 10a) and the 15 possible isotopologues of the purine core (FIG. 10b) with six 6 mDa-spaced representative isotopologues (boxed).
Figure 10:
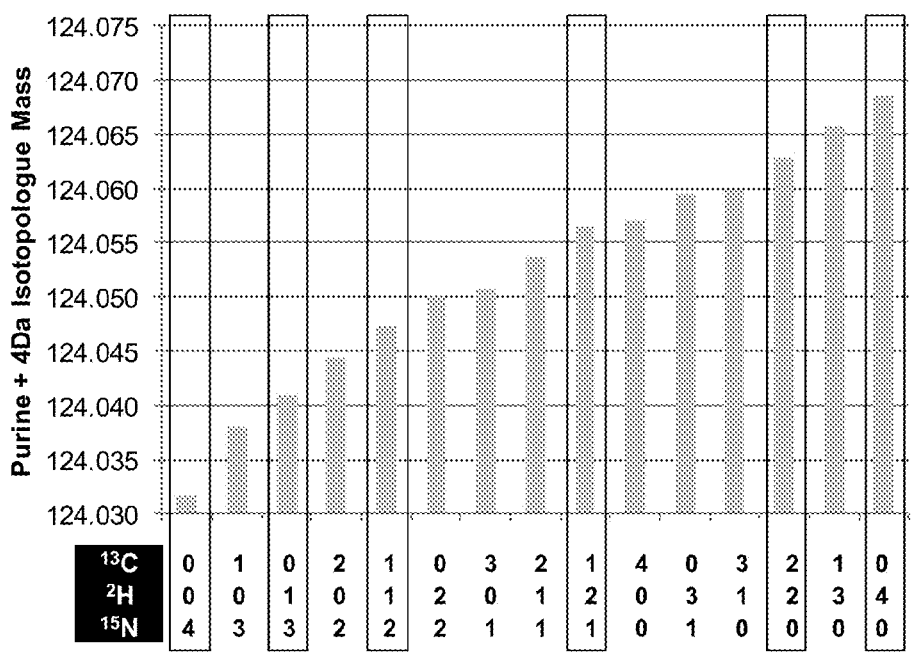

In one embodiment, distinct lysine+8 Da isotopologues can be used to synthesize the heavy peptide standards. These individual peptides are mixed at a defined ratio, resulting in a single isotopologue set. In one embodiment, a multiplexed AQUAplex peptide set can be synthesized in one reaction using precursor FMOC-protected amino acid precursors or solid phase resins pre-mixed at a designated ratio (FIGS. 4, 8). In one embodiment, two or more peptide isotopologues may be mixed at a defined ratio to create a multiplexed internal standard heavy peptide isotopologue mixture. As an example, low resolution separation is shown in FIG. 3 for peptides synthesized in one reaction with AQUAplex lysine (K) isotopologues at a defined ratio of four $^{13}C_6^{15}N_2$, three $^{13}C_4^{15}N_2^2H_2$, two $^{13}C_6^2H_2$, and one $^2H_8$. Peptides and modified peptides are synthesized as isotopologues using protected amino acid precursors, e.g., lysine, arginine, histidine, proline, leucine, tyrosine (FIGS. 10a-b). In one embodiment, synthesis is accomplished by premixing or combining the heavy peptide standards at a defined or fixed ratio, enabling replicate measurement or generation of a standard calibration curve. At low mass resolution, heavy isotopologues are not resolved, but instead are summed or additive. This results in a composite peak of higher intensity, with or without a detectable weighted average mass defect, and the intensity of each of the isotopologue peaks becomes summed within the low resolution single peak to provide a greater signal in the mass spectrum. The higher intensity peak is more easily detected by mass spectrometry than the target peptide or the individual heavy peptide isotopologues, allowing triggered ion isolation and MS enrichment. This invention thus extends the sensitivity of mass spectroscopy analysis to lower concentrations, because the combined isotopologue peak is used as the marker or "sign post" for the presence of the light target peptide peak, which may not have been noticed by the mass spectrometer without this marker due to the low intensity of the peak.

The heavy peptides can be synthesized individually, or they can be synthesized as a mixture by combining isotopologue amino acid precursors or solid phase supports that have been preactivated with isotopologue precursors at predefined ratios. For example, to prepare a four-isotopologue mixture, four of the lysine derivatives represented by the bars of FIG. 6 are first attached to a solid phase peptide synthesis support using standard methods known in the art. To prepare four otherwise identical peptides containing different but known amounts of these isotopologue lysine residues, the four precursor supports then are mixed in a desired ratio, for example 4:3:2:1 (FIG. 4). The peptide is then synthesized using this mixture of isotopologue precursors by adding one amino acid at a time, as is done in typical amino acid synthesis procedures. Once the peptide synthesis is complete and the peptide is cleaved from the support and purified, the resultant mixture will contain four isotopologues of the same peptide, where one of the isotopologues is at ½, ⅓ or ¼ the concentration of the other isotopologues. A peptide isotopologue set that contains the heavy isotopologue at another position can be synthesized by incorporating a defined mixture of protected amino acid isotopologues. Other mixtures of isotopologues may be prepared using similar methods, including those which would contain more than two isotopologues at known concentrations to create a multi-point standard curve. Use of this single reaction or "one pot" synthesis provides several advantages: it reduces the number of reactions required for synthesizing the multiplexed isotopologue set, it allows the same predefined mixture of activated supports to be used as a precursor for multiple peptide reactions, it ensures enhanced synthesis reproducibility of quantitative multiplexed peptide isotopologue sets, and it permits the absolute amount of the isotopologue mixture to be quantified in one amino acid analysis. The result is that synthesis is simplified and reproducibility is improved, with a lowered manufacturing cost for the protein or peptide standards.

The isotopologue set or sets of the internal standard may be prepared in a form for commercial use, e.g., packaged with instructions for use as a kit. Such a kit could include instructions for high resolution mass spectrometry that may or may not have the capability to isolate and enrich a mass region (e.g., by an ion trap or quadrupole/hexapole/octapole mass filter), and/or the capability to fragment isolated ions with collisional or chemical fragmentation methods. Methods using such a kit include high resolution mass spectrometry with or without mass range isolation and/or multistage fragmentation.

Incorporation of different heavy atoms among peptide family members causes a mass defect to occur among peptides, which slightly alters the real mass by mDa. The heavy peptide peak of an AQUAplex MS separation contains multiple resolvable peaks under high resolution MS. These multiple resolvable peaks represent multiple concentrations of the isotopomeric peptides within a single peptide family. Because multiple concentrations of the isotopomeric peptides can be contained within the heavy AQUAplex peak, a standard curve is contained within the heavy peak as a series of known concentrations of the mass-defect labeled peptide.

An AQUAplex standard quantitation curve is generated as follows. Multiple concentrations of the isotopomeric peptides, as a series of known concentration of the mass-defect labeled peptides, are contained within the heavy AQUAplex peak. The number of points in the standard curve is governed by the resolution power of the mass spectrometer used in the assay. In embodiments, two to six peaks can be resolved. In one embodiment, an AQUAplex internal standard curve for quantitation is obtained using two or more different isotopomers at different concentrations (FIG. 3). An internal standard curve can be generated readily for each target peptide being measured. The high intensity of the low mass resolution peak serves as a signpost of the analyte for triggered acquisition strategies. The use of standard curves improves and validates diagnostic assays using mass spectrometry analysis.

In a similar embodiment, amino acid isotopologue sets can be used for synthesis of heavy protein isotopologue sets. These heavy protein isotopologues can be made with fixed ratios of the amino acid precursors, so that after digestion, isotopologue sets of every peptide of the heavy protein is present at the same concentration. Peptides derived by proteolysis of the native and heavy protein set can be used to quantify all peptides of a target protein. This heavy protein set may or may not be quantified as an absolute internal standard. An AQUA peptide with a distinct mass can be included for absolute quantitation of the native and heavy protein standard set. In this embodiment, digestion efficiency for each peptide is normalized, and distinct peptides from the target analyte that are regulated independent of the protein level, such as by post translational modification, may be identified. The stoichiometry of native to modified peptides of the target analyte may have greater diagnostic utility than the overall target protein concentration.

The need to maintain inter-assay precision in an AQUAplex assay is important, as is the need to improve and validate diagnostic applications of mass spectroscopy. The inventive method is compatible with existing quantitative protein workflow systems that use protein digestion and LC-MS for peptide detection. It combines AQUAplex methods with NeuCode amino acids or mass tags and can be used, e.g., in a universal reporter assay, to result in multi-sample and multi-target analysis with absolute protein or peptide quantitation. The inventive method provides multiple replicates of the heavy peptide internal standard, without increasing the complexity of the sample. The inventive method allows absolute quantitation with high resolution mass spectrometry at the MS1 or MSn level, with the ability to verify and quantify sequence fragment ions with multistage MS. The inventive method allows triggered ion isolation and MS enrichment using the mass of the low resolution summed peak of the heavy peptide internal standard isotopologues. The inventive method permits acquisition of a set of heavy peptide replicates at high resolution, providing more accurate target peptide quantitation. The inventive method permits acquisition of a heavy peptide standard curve at high resolution for more accurate target peptide quantitation across a broad dynamic range. The inventive method provides the ability to incorporate the amino acid isotopologues into the internal standard heavy peptide and internal standard heavy protein. The inventive method facilitates multiplexed synthesis of the heavy peptide and protein isotopologues using a premixed set of precursor amino acids isotolopogues or solid phase precursors. The inventive method provides the ability to incorporate the amino acid isotopologues into a universal reporter peptide sequence.

Current MS-based method for absolute protein quantitation (e.g. AQUA) utilize a heavy internal standard heavy peptide that is spiked into an analyte sample, and the ratio of the MS signal intensity or AUC of the target analyte peptide to the internal standard heavy peptide is used to calculate the absolute amount of target analyte in the sample. Ideally, the concentration of this internal standard is within one order of magnitude of the target analyte for accurate quantitation. Clinically relevant protein biomarkers are present across a broad range of concentrations, such as cardiac myoglobin (Mb) that is present in plasma from normal subjects at 1 ng/ml to 85 ng/ml, but is increased to 200 ng/ml to 1,100 ng/ml by a myocardial infarction, and up to 3,000 ng/ml by fibrinolytic therapy to treat the infarct (Anderson and Anderson (2002) The human plasma proteome: History, character, and diagnostic prospects. Mol. Cell. Proteomics 1, 845-867). Troponin I above a cut off of 100 pg/ml is another approved marker of myocardial infarction, but this cut off is >500-fold lower than Mb. Additional examples of the broad dynamic range of clinical biomarkers include multiple interleukins below 1 pg/ml, CEA above 500 pg/ml, prostate specific antigen above 4 ng/ml, alpha-fetoprotein above 20 ng/ml, and B-type naturietic peptide (BNP) above 8 pg/ml (Polanski and Anderson (2006) A List of Candidate Cancer Biomarkers for Targeted Proteomics. Biomarker Insights 1, 1-48). For these and other examples, the broad dynamic range of target analytes requires use of multiple internal standard concentrations in MS assays for accurate analyte quantitation. The disclosed inventive method addresses this dynamic range requirement in one assay.

Labeled Peptide Internal Standards (AQUA Peptides) and Heavy Protein Internal Standards AQUA peptide labeled internal standards are disclosed in WO 03/016861 and U.S. Pat. No. 7,501,286, each of which is expressly incorporated by reference herein in its entirety. Heavy isotope labeled proteins as internal standards are disclosed in U.S. Pat. No. 7,939,331, and proteolytic digestion yields the set of heavy peptide standards. Briefly, and as disclosed in these references, the peptide is synthesized using one or more labeled amino acids (i.e., the label is actually part of the peptide) or less preferably, labels may be attached after synthesis. The label is a mass-altering label. The mass of the label should preferably be unique to shift fragment masses produced by MS analysis to regions of the spectrum with low background. The ion mass signature component is the portion of the labeling moiety which preferably exhibits a unique ion mass signature in mass spectrometric analyses. The sum of the masses of the constituent atoms of the label is preferably uniquely different than the fragments of all the possible amino acids. As a result, the labeled amino acids and peptides are readily distinguished from unlabeled amino acids and peptides by their ion/mass pattern in the resulting mass spectrum. In a preferred embodiment, the ion mass signature component imparts a mass to a protein fragment produced during mass spectrometric fragmentation that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions and the labeled tag preferably remains soluble in the MS buffer system of choice. Preferably, the label does not suppress the ionization efficiency of the protein. More preferably, the label does not alter the ionization efficiency of the protein and is not otherwise chemically reactive. Alternatively, or additionally, the label contains a mixture of two or more isotopically distinct species to generate a unique mass spectrometric pattern at each labeled fragment position.

Peptide internal standards comprise mass-altering labels which are stable isotopes, e.g., isotopes of hydrogen, nitrogen, oxygen, carbon, or sulfur. Suitable isotopes include, but are not limited to, $^2H$, $^{13}C$, $^{15}N$, $^{17}O$, $^{18}O$, or $^{34}S$. Pairs of peptide internal standards can be provided, comprising identical peptide portions but distinguishable labels, e.g., peptides may be labeled at multiple sites to provide different heavy forms and isotopologues of the peptide. Multiple labeled amino acids may be incorporated in a peptide during the synthesis process. The label may be part of a peptide comprising a modified amino acid residue, such as a phosphorylated residue, a glycosylated residue, an acetylated residue, a ribosylated residue, a farnesylated residue, or a methylated residue. In this embodiment, pairs or larger sets of peptide internal standards corresponding to modified and unmodified peptides also can be produced. In one aspect, such a pair/set is differentially labeled.

Peptide internal standards are characterized according to their mass-to-charge ratio (m/z) and preferably, also according to their retention time on a chromatographic column (e.g., such as an HPLC column). Internal standards are selected which co-elute within 30 seconds with peptides of identical sequence but which are not labeled. Isotopologues with $^2$H have a slightly different retention on HPLC, so these isotopologues will elute near but not simultaneously with the isotopologues. More $^2$H will result in more retention time shift.

The peptide internal standard is then analyzed by MS1 or by fragmenting the peptide with multistage MS (MSn). Fragmentation can be achieved by inducing ion/molecule collisions by a process known as collision-induced dissociation (CID) (also known as collision-activated dissociation (CAD)). Collision-induced dissociation is accomplished by selecting a peptide ion of interest with a mass analyzer and introducing that ion into a collision cell. The selected ion then collides with a collision gas (typically argon or helium) resulting in fragmentation. Generally, any method that is capable of fragmenting a peptide is encompassed within the scope of the present invention. In addition to CID, other fragmentation methods include, but are not limited to, high energy collisional dissociation (HCD), surface induced dissociation (SID), blackbody infrared radiative dissociation (BIRD), electron capture dissociation (ECD), post-source decay (PSD), LID, and the like.

The fragments are then analyzed to obtain a fragment ion spectrum. One suitable way to do this is by CID in multistage mass spectrometry (MS$^n$). Traditionally used to characterize the structure of a peptide and/or to obtain sequence information, it is a discovery of the present invention, that high resolution MS1 and/or high resolution MS$^n$ provides enhanced sensitivity in methods for quantitating absolute amounts of proteins. Thus, in one aspect, peptide internal standards are generated for low abundance proteins (e.g., below 2000 copies/cell).

High resolution, absolute mass MS1 can be used in combination with retention time information to reliably verify and quantify a target peptide. In one embodiment, the internal standard isotopologue cluster at low resolution can serve as a higher intensity MS1 signal to trigger isolation and enrichment of one or more target peptides and internal standard pairs. In one embodiment, the high resolution and accurate mass measurement of the isotopologue cluster is used as an MS instrument mass calibration standard to provide confirmation of the targeted peptide MS1 mass signal.

In one embodiment, a peptide internal standard is analyzed by at least two stages of mass spectrometry to determine the fragmentation pattern of the peptide and to identify a peptide fragmentation signature for peptide verification. A peptide signature is obtained in which peptide fragments have significant differences in m/z ratios to enable peaks corresponding to each fragment to be well separated. Signatures are desirably unique, i.e., diagnostic of a peptide being identified and comprising minimal if any overlap with fragmentation patterns of peptides with different amino acid sequences. If a suitable fragment signature is not obtained at the first stage, additional stages of mass spectrometry are performed until a unique signature is obtained. This fragmentation signature ensures that peaks of the same exact mass are not simply rearrangements of the same amino acids in a different order.

Fragment ions in the MS/MS and MS$^3$ spectra are generally highly specific and diagnostic for peptides of interest. In contrast to prior art methods, the identification of peptide diagnostic signatures provides for a way to perform highly selective analysis of a complex protein mixture, such as a cellular lysate in which there may be greater than about 100, about 1000, about 10,000, or even about 100,000 different kinds of proteins. Thus, while conventional mass spectroscopy would not be able to distinguish between peptides with different sequences but similar m/z ratios (which would tend to co-elute with any labeled standard being analyzed), the use of peptide fragmentation methods and multistage mass spectrometry in conjunction with LC methods, provide a way to detect and quantitate target proteins which are only a small fraction of a complex mixture (e.g., present in less than 2000 copies per cell or less than about 0.001% of total cellular protein) through these diagnostic signatures.

Multiple peptide subsequences of a single protein may be synthesized, labeled, and fragmented to identify optimal fragmentation signatures. In one embodiment, at least two different peptides are used as internal standards to identify/quantify a single protein, providing an internal redundancy to any quantitation system. In another embodiment, peptide internal standards are synthesized which correspond to a single amino acid subsequence of a target polypeptide but which vary in one or more amino acids. The peptide internal standards may correspond to known variants or mutations in the target polypeptide or can be randomly varied to identify all possible mutations in an amino acid sequence.

In one embodiment, peptides corresponding to different modified forms of a protein are synthesized, providing internal standards to detect and/or quantitate changes in protein modifications in different cell states. In one embodiment, peptide internal standards are generated which correspond to different proteins in a molecular pathway and/or modified forms of such proteins (e.g., proteins in a signal transduction pathway, cell cycle, metabolic pathway, blood clotting pathway, etc.) providing panels of internal standards to evaluate the regulated expression of proteins and/or the activity of proteins in a particular pathway. Combinations of the above-described internal standards can be used in a given assay.

Generally, the sample will have at least about 0.01 mg of protein, at least about 0.05 mg, and usually at least about 1 mg of protein or 10 mg of protein or more, typically at a concentration in the range of about 0.1-10 mg/ml. The sample may be adjusted to the appropriate buffer concentration and pH, if desired.

In one embodiment, a known amount of a labeled peptide internal standard corresponding to a target protein to be detected and/or quantitated, is added to a sample such as a cell lysate. In one embodiment, about 10 femtomoles is spiked into the sample. The sample is contacted with a protease activity, e.g., one or more proteases or appropriate chemical agent(s) are added to the sample, and the spiked sample is incubated for a suitable period of time to allow peptide digestion. If the target protein is present in the sample, the digestion step should liberate a target peptide identical in sequence to the peptide portion of the internal standard and the amount of target peptides so liberated from target proteins in the sample should be proportional to the amount of target protein in the sample.

In one embodiment, a separation procedure is performed to separate a labeled peptide internal standard and corresponding target peptide from other peptides in the sample. Representative examples include high-pressure liquid chromatography (HPLC), reverse phase-high pressure liquid chromatography (RP-HPLC), electrophoresis (e.g., capillary electrophoresis), anion or cation exchange chromatography, and open-column chromatography. Internal standards are selected so that they co-elute with their corresponding target peptides as pairs of peptides that differ only in the mass contributed by the mass-altering label.

Each peptide then is examined by monitoring of high resolution absolute mass MS1 or a selected reaction in the mass spectrometer. This involves using the prior knowledge gained by the characterization of the peptide internal standard and then requiring the mass spectrometer to continuously monitor a specific ion in the MS1, MS/MS, or MS$^n$ spectrum for both the peptide of interest and the internal standard. After elution, the areas-under-the-curve (AUC) for both the peptide internal standard and target peptide peaks are calculated. The ratio of the two areas provides the absolute quantification that can be normalized for the number of cells used in the analysis and the protein's molecular weight, to provide the precise number of copies of the protein per cell.

The inventive method determines the presence of and/or quantity of a modification in a target polypeptide. In one embodiment, the label in the internal standard is attached to a peptide comprising a modified amino acid residue or to an amino acid residue that is predicted to be modified in a target polypeptide. In one embodiment, multiple internal standards representing different modified forms of a single protein and/or peptides representing different modified regions of the protein are added to a sample and corresponding target peptides (bearing the same modifications) are detected and/or quantified. In one embodiment, standards representing both modified and unmodified forms of a protein are provided to compare the amount of modified protein observed to the total amount of protein in a sample.

Reagents for performing the method comprise a peptide isotopologue internal standard labeled with a stable isotope. In one embodiment, the standard has a unique peptide fragmentation signature diagnostic of the peptide. The peptide is a subsequence of a known protein and can be used to identify the presence of and/or quantify the protein in sample, such as a cell lysate.

The invention additionally provides kits comprising one or more peptide internal standards labeled with a stable isotope or reagents suitable for performing such labeling. In one embodiment, the method utilizes isotopes of hydrogen, nitrogen, oxygen, carbon, or sulfur. Suitable isotopes include, but are not limited to, $^2$H, $^{13}$C, $^{15}$N, $^{17}$O, $^{18}$O, or $^{34}$S. In one embodiment, pairs of peptide internal standards are provided, comprising identical peptide portions but distinguishable labels, e.g., peptides may be labeled at multiple sites to provide different heavy or isotopologue forms of the peptide. Pairs of peptide internal standards corresponding to modified and unmodified peptides also can be provided.

In one embodiment, a kit comprises peptide internal standards comprising different peptide subsequences from a single known protein. In one embodiment, the kit comprises peptide internal standards corresponding to different known or predicted modified forms of a polypeptide. In one embodiment, the kit comprises peptide internal standards corresponding to sets of related proteins, e.g., such as proteins involved in a molecular pathway (a signal transduction pathway, a cell cycle, etc.), or which are diagnostic of particular disease states, developmental stages, tissue types, genotypes, etc. Peptide internal standards corresponding to a set may be provided in separate containers or as a mixture or "cocktail" of peptide internal standards.

In one embodiment, the peptide internal standard comprises a label associated with a modified amino acid residue, such as a phosphorylated amino acid residue, a glycosylated amino acid residue, an acetylated amino acid residue, a farnesylated residue, a ribosylated residue, and the like. In another aspect, a pair of reagents is provided, a peptide internal standard corresponding to a modified peptide and a peptide internal standard corresponding to a peptide, identical in sequence but not modified.

In one embodiment, one or more control peptide internal standards are provided. For example, a positive control may be a peptide internal standard corresponding to a constitutively expressed protein, while a negative peptide internal standard may be provided corresponding to a protein known not to be expressed in a particular cell or species being evaluated. For example, in a kit comprising peptide internal standards for evaluating a cell state in a human being, a plant peptide internal standard may be provided.

In one embodiment, a kit comprises a labeled peptide internal standard as described above and software for analyzing mass spectra (e.g., such as SEQUEST).

Preferably, the kit also comprises a means for providing access to a computer memory comprising data files storing information relating to the diagnostic absolute mass MS1 and MSn fragmentation signatures of one or more peptide internal standards. Access may be in the form of a computer readable program product comprising the memory, or in the form of a URL and/or password for accessing an internet site for connecting a user to such a memory. In one embodiment, the kit comprises diagnostic accurate mass MS1 and MSn fragmentation signatures (e.g., such as mass spectral data) in electronic or written form, and/or comprises data, in electronic or written form, relating to amounts of target proteins characteristic of one or more different cell states and corresponding to peptides that produce the fragmentation signatures.

Neutron-Encoded Mass Signatures for Multiplexed Proteome Quantification (NeuCode) Method The neutron-encoded protein quantification method is disclosed in Hebert et al., Neutron-encoded mass signatures for multiplexed proteome quantification, Nature America, Inc. 2013 Advance Online Publication), which is expressly incorporated by reference herein in its entirety. As disclosed, it uses subtle mass differences caused by nuclear binding energy variation in stable isotopes. These mass differences are synthetically encoded into amino acids and incorporated in yeast and mouse proteins by metabolic labeling. Mass spectrometry analysis with high mass resolution (>100,000) reveals the isotopologue-embedded peptide signal, permitting quantification.

The multiplexing capacity of isobaric tandem mass tags has been expanded from six to eight using the concomitant swapping of a $^{12}$C for a $^{13}$C atom and a $^{15}$N for a $^{14}$N atom to produce a new tag with a 6-mDa mass difference that can be distinguished with a mass resolution of 50,000 at a mass-to-charge ratio (m/z) of 130 (Werner et al. (2012) High-resolution enabled TMT8-plexing. Anal Chem 84(16):7188-94; McAllister et al. (2012) Increasing the multiplexing capacity of TMTs using reporter ion isotopologues with isobaric masses. Anal Chem 84(17):7469-78). Mass defect, the cause of this subtle mass change, arises from the fact that nuclear binding energy, the energy required to break down a nucleus into its component nucleons, is different for each isotope of every element. The tandem mass tag approach still relies on MS/MS-based quantification, however, and does not resolve the accuracy and reproducibility issues of isobaric tagging. It was suggested that other elements, besides C and N, could encode neutron mass signatures. Indeed, mass defects can be induced with many elements and their isotopes: for example, $^{12}$C/$^{13}$C (+3.3 mDa), $^{1}$H/$^{2}$H (+6.3 mDa), $^{16}$O/$^{18}$O (+4.2 mDa), $^{14}$N/$^{15}$N (−3.0 mDa) and $^{32}$S/$^{34}$S (−4.2 mDa). It was hypothesized that calculated incorporation of these isotopes into proteomes would generate a new MS1-centric quantification technology that combines the accuracy of SILAC with the multiplexing capacity of isobaric tagging. This method has been called neutron encoding (NeuCode).

In contrast to the use of NeuCode for mass tagging a proteome, the methods disclosed use the concept of mass defect to create labeled peptide standards to be used for absolute quantitation of an analyte.

Use of these mass defects in the creation of labeled peptide standards exploits the subtle differences in nuclear binding energy between isotopes. The approach effectively compresses isotopic information into a very narrow m/z space (~0.0050-0.040) so that it is easily concealed or revealed by varying mass resolution. Current Fourier transform MS systems offer ultra-high resolution (>1,000,000) and will permit the use of mass defect-labeled peptides separated by as little as ~6 mDa. In one embodiment, synthesis of custom lysine isotopologues that offer 7-plex quantification: +8 Da at 0, 6, 12, 18, 24, 30, and 36 mDa spacings are created (FIGS. 6, 7*a-b*). Further, such >7-plex isotopologue sets could be generated with 12 additional neutrons, allowing the combination of isotopologues in multiple isotopic clusters. For example, each peptide would be present in three isotopic clusters, just as in a traditional triplex; however, each cluster would reveal 5-7 distinct peaks upon high-resolution scan analysis. By combining peptides containing these 19 isotopologues of lysine (5+7+7), mass defect labeling should facilitate 19-plex experiments. Similarly, by combining 8-plex isotopologue sets containing arginine isotopologues with 6 and 10 additional neutrons, 16-plex multiplexed quantitation of arginine-containing peptides can be performed as well. By combining mass defect with mass differential tags for relative and absolute quantification, highly multiplexed quantitative accuracy and precision was achieved.

Isotopologue Mass Tag Assays

Figure 9:
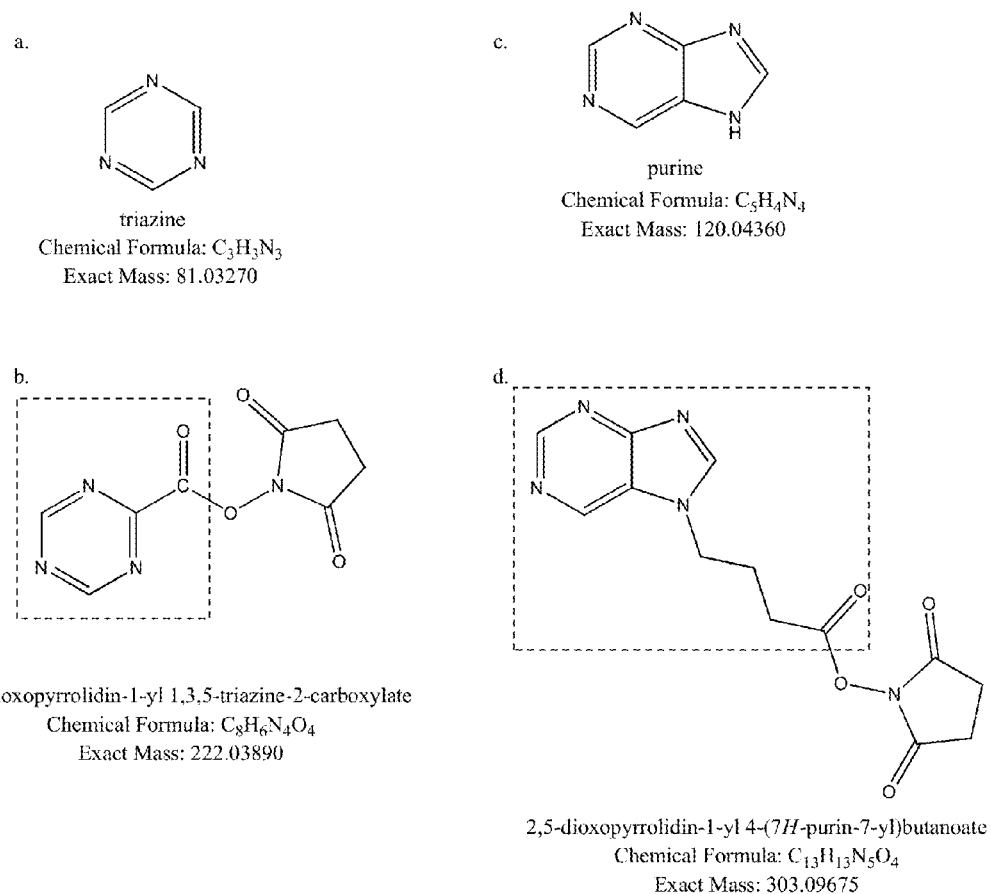
FIG. 9 shows the chemical structures of triazine and purine core molecules and the corresponding amine-reactive N-hydroxysuccinimide derivatives.

Covalent mass tags are an alternative method to create isotopologue sets of internal standard peptides isotopologues. Mass tags have greater flexibility in chemical structure and thus these chemical tags are more easily synthesized over synthesis of specific chiral amino acid precursors. Isotopologue mass tags may be used to tag non-protein samples, including nucleotides, glycans, lipids, and metabolites. In addition, isotopologue mass tags may incorporate unique features that improve solubility, chromatographic retention properties, ionization efficiency, and/or peptide fragmentation behavior. Two example core structures and their related amine-reactive tags are described (FIG. 9). These example tags are based upon triazine cyclic and purine heterocyclic ring structures that are modified with amine-reactive N-hydroxysuccinimide (NHS). These tags may be synthesized as known in the art without heavy isotopes or with different combinations of heavy isotopes. The light and heavy isotopic reagents may have a minimum mass difference of 4 Da. The possible isotopologues and masses of the heavy triazine and purine core molecules are shown (FIGS. 10*a-b*). These isotopologues may be used to create a multiplexed reagent set that can be resolved with >100,000 resolution. In one embodiment, the heavy isotopologues are pre-mixed at a defined ratio. An analyte protein sample is digested with a protease, such as trypsin or LysC, and the light tags are covalently attached to the peptides through reactive amines at the amino-terminus of the peptide and lysine residues. An internal standard peptide at a known absolute concentration to quantify the target analyte peptide is labeled with the heavy isotopologue tag set. At low resolution, the area under the curve (AUC) of the light targeted analyte and the composite AUC of the heavy isotopologue set can be used to quantify the target analyte, and at high resolution the internal standard isotopologues can be used to define a standard curve for more accurate quantitation of the target analyte.

Universal Reporter Assays

The use of a universal reporter is described in WO 2012/005838 and WO 2012/006406. This method results in absolute quantification of analytes by MS, and enables a simple concentration calibration of analytes in reference solutions. The method uses a heavy isotope labeled analyte (internal standard) that is in equimolar concentration with, and that is cleavably coupled to, a reporter R (that may or may not be heavy isotope labeled); and a heavy isotope labeled universal reporter U. Analytes include, but are not limited to, peptides, polypeptides, and proteins. Universal reporter U includes, but is not limited to, peptides (i.e., polymers of amino acids) and other polymers.

In one embodiment the inventive method resulted in absolute quantification of peptide, polypeptide, and proteins analytes by MS. The method used a heavy isotope labeled peptide (proteotypic peptide, described below; internal standard) that was present in equimolar concentration with, and was cleavably coupled at a proteolytic site to, an optionally heavy isotope labeled reporter peptide R; a heavy labeled universal reporter peptide U analyzed by amino acid analysis. The heavy isotope labeled peptide need not undergo amino acid analysis. In one embodiment, several different proteotypic peptides from a single protein, linked to separate reporter peptides R, were analyzed. In one embodiment, several different proteotypic peptides concatenated into one polypeptide, linked to a single reporter peptide R were analyzed.

Figure 11:
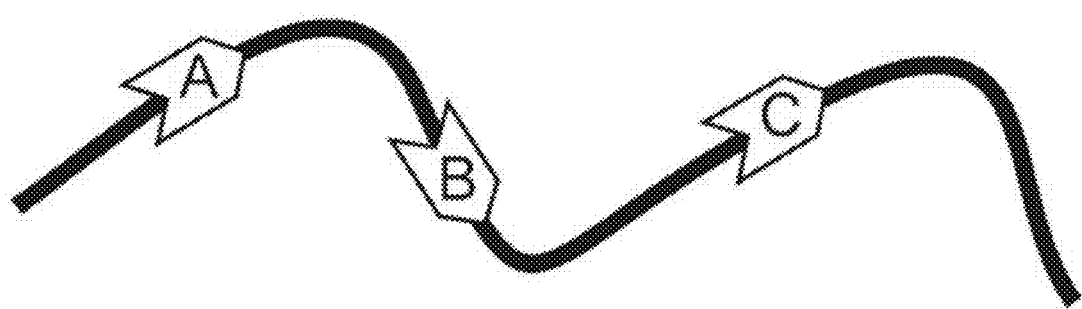
FIG. 11 schematically shows peptides for mass spectroscopy quantitation.

FIG. 11 shows proteotypic peptides A, B, and C from protein or polypeptide P. A proteotypic peptide is a signature peptide that fragments into a predictable ion series following MS dissociation to allow specific identification and quantitation of the parent protein, whether in a purified form or from a complex mixture. It has characteristics that render it readily quantified. A signature peptide is an unambiguous identifier of a specific protein. Any protein contains between 10 and 100 signature peptides. Any signature peptide meets most of the following criteria: easily detected by mass spectroscopy, predictably and stably eluted from a liquid chromatography (LC) column, enriched by reversed phase high performance liquid chromatography (RP-HPLC), good ionization, and good fragmentation. A peptide that is readily quantified meets most of the following criteria: readily synthesized, ability to be highly purified (>97%), soluble in ≥20% acetonitrile, low non-specific binding, oxidation resistant, post-synthesis modification resistant, and a hydrophobicity or hydrophobicity index≥10 and ≤40. The hydrophobicity index is described in Krokhin, Molecular and Cellular Proteomics 3 (2004) 908, which is expressly incorporated herein by reference. A peptide having a hydrophobicity index less than 10 will not be reproducibly resolved by RP-HPLC. A peptide having a hydrophobicity index greater than 40 will not be reproducibly eluted from a RP-HPLC column.

Figure 16:
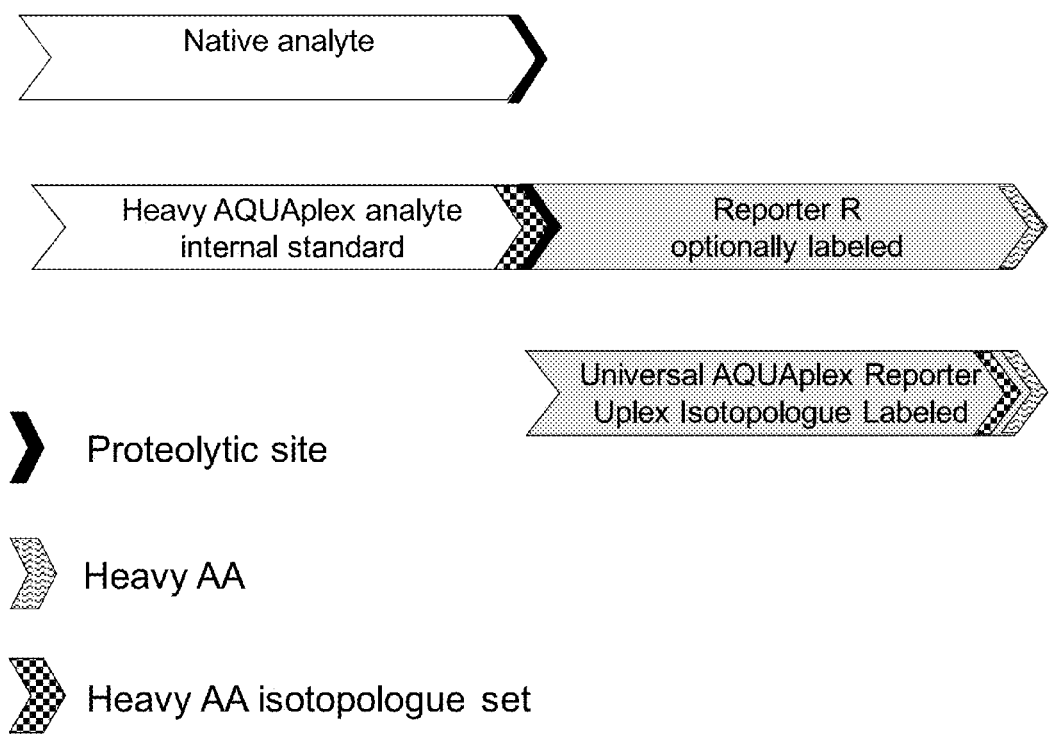
FIG. 16 schematically shows configuration and relationship among components.
Figure 17:
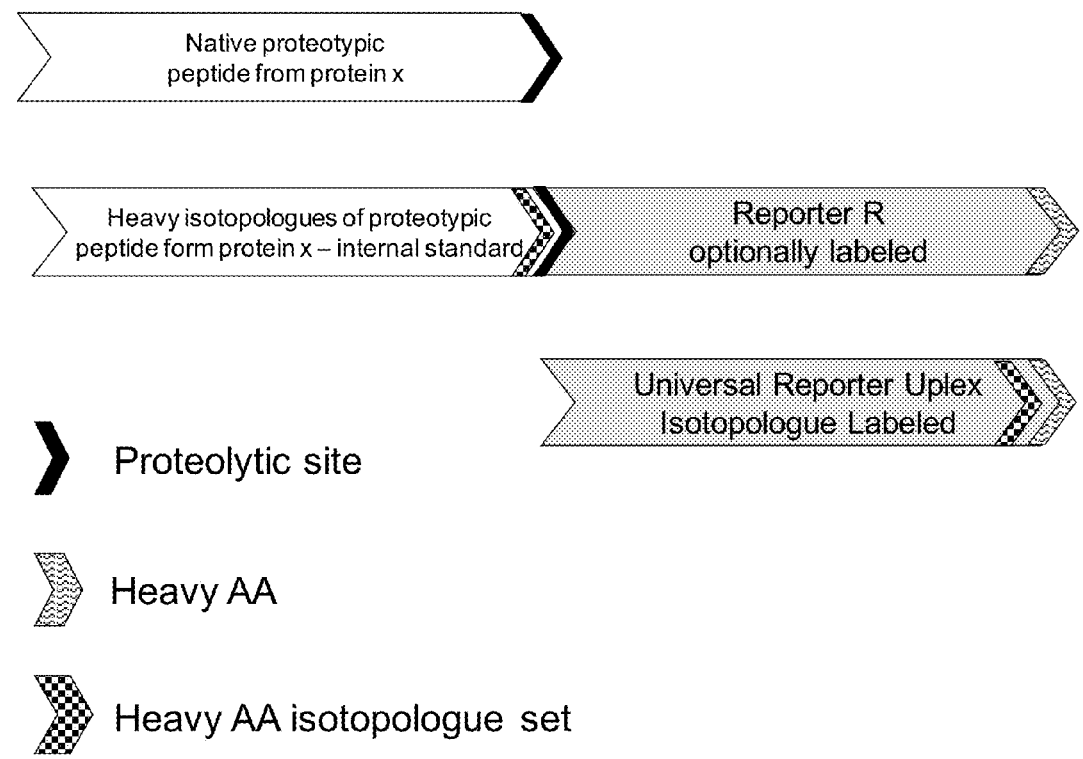
FIG. 17 schematically shows configuration and relationship among peptide components.

The inventive method uses an internal standard that is the heavy isotopologue (labeled) form of the analyte to be quantified, also referred to as a AQUAplex heavy analyte and shown in FIG. 16. In the embodiment using a proteotypic peptide isotopologue set, the internal standard is the labeled isotopologue set of the proteotypic peptide, also referred to as heavy proteotypic peptide isotopologues, as shown in FIG. 17.

Isotope dilution mass spectrometry (IDMS) refers to the use of heavy isotope-labeled peptides as internal standards to establish the concentration versus MS response relationship and to perform absolute quantitation of peptide. The heavy isotope labeled peptide has identical properties as the unlabeled peptide, except that its mass is shifted by the incorporated isotope(s). As a result of this mass shift, a known amount of the isotope-labeled peptide can be used as an internal standard for peptide quantitation. The IDMS method results in targeted mass spectrometry (selected ion monitoring (SIM)/selected reaction monitoring (SRM)/multiple reaction monitoring (MRM)) quantitation of peptides in complex samples or mixtures. SIM and SRM encompass the MS acquisition setup to quantify a list of target proteins by the quantitation of the parent or specific fragment ions from proteotypic peptides of these target proteins, respectively. Targeted assay development must be fast, have high throughput, be sensitive, specific, targeted, robust, reproducible, and cost effective; it typically uses liquid chromatography-tandem mass spectrometry (LC-MS/MS, LC/MS$^2$). However, precise quantitation of large number of peptides in targeted proteomics experiments using SRM remains challenging because of specificity and duty cycle requirements. SRM specificity refers to the choice of parent/fragment ion combinations (e.g., transitions) that provide a specific quantitative response for the target and internal standard peptides with high sensitivity. Duty cycle refers to the limited number of SRM transitions that can be monitored simultaneously by MS in a multiplexed SRM assay. To address the duty cycle limitations, SRM methods are typically scheduled or timed such that transitions for a given target are only monitored in a retention time window expected for the given target. This requires complex SRM method setup prior to data acquisition and reproducible chromatography to ensure that the target transitions are monitored completely with sufficient baseline before and after the peak for accurate AUC determination. SIM monitoring includes the isolation and enrichment of a targeted peptide and internal standard in order to improve the sensitivity of the assay. AQUAplex assays acquired with high resolution MS1 scans do not require scheduling or the selection of transitions, and all of the quantitative data analysis can be performed post-acquisition.

In IDMS, the native proteotypic peptide differs from the heavy proteotypic peptide only due to incorporation of a heavy amino acid. A heavy amino acid contains $^{13}$C (the heavy isotope of carbon) and/or $^{15}$N (the heavy isotope of nitrogen), $^{18}$O (the heavy isotope of oxygen), and/or $^2$H (the heavy isotope of nitrogen), and different combinations of these isotopes can be combined to produce isotopologue sets containing the same unit mass but slightly different accurate masses observable with high resolution mass spectrometry. The insertion of a heavy amino acid isotopologues results in HeavyPeptide AQUAplex, which differs from the proteotypic peptide only by the difference in mass. The purity of the heavy peptide isotopologue mixture is increased to >97% using preparative high performance liquid chromatography (HPLC). The precise quantity of HeavyPeptide AQUAplex is determined by amino acid analysis. The mixture of the peptide to be quantified and HeavyPeptide AQUAplex as the internal standard yields two peaks in low resolution mass spectroscopy: the two peaks have the same elution time, but different masses. With high resolution MS, the HeavyPeptide AQUAplex set will be resolved as distinct component masses separated by the mass defect between isotopologues. Peptides containing $^2$H may exhibit a slight reduction in retention time on reversed phase HPLC, but this does not affect quantitative accuracy because it does not affect the AUC quantitation. HeavyPeptide AQUAplex is spiked into the sample to be analyzed at a known quantity, making it possible to use its quantity to calculate the quantity of the peptide to be analyzed from the peak areas. At low MS or MSn resolution, the method compares the AUC of the corresponding combined MS peak from the heavy isotope labeled peptide isotopologue set, with the peak of the non-labeled peptide with the exact same sequence originating from the analyte (e.g., polymer, protein, peptide, or polypeptide) being quantified. At high MS or MSn resolution, the method compares the area of the corresponding MS peaks from each of the heavy isotope labeled peptide isotopologues, with the peak of the non-labeled peptide with the exact same sequence originating from the analyte (e.g., polymer, protein, peptide, or polypeptide) being quantified. The quantitation precision is directly correlated to the accuracy of the amount of the heavy peptide added to the sample.

The following example, while used specifically with a protein analyte, illustrates the general method applicable for analytes, whether protein or non-protein. A sample (e.g., biological sample, food sample) containing numerous proteins is treated with a cleavage agent such as a protease (e.g., trypsin). Trypsin cleaves at each R amino acid and K amino acid, yielding numerous fragments, each fragment having about 13 amino acids (range 6 amino acids to 20 amino acids). Into this fragment-containing sample to be analyzed is introduced (spiked) one, two, or three HeavyPeptide AQUAplex internal standards, and quantitation is performed as described. In embodiments using proteolytic digestion, the quantitation precision is also directly correlated to the digestion predictability and efficiency.

In one embodiment, proteins contain one, two, or three proteotypic peptide sequences, labeled as heavy or light (HeavyPeptide AQUAplex). The samples to be analyzed are spiked with the proteotypic peptides and quantitated by LC-MS/MS.

In AQUAplex IDMS, the internal standard isotopologue set has the same sequence as the proteotypic peptide from the protein to be quantified, but the internal standard is a mixture of heavy isotopologues that have a different mass from the proteotypic peptide. The sequence of the internal standard is thus pre-determined by the protein sequence; it cannot be changed. The AQUAplex internal standard must be quantified by amino acid analysis to determine the total peptide concentration and by high resolution MS to determine the relative proportion and thus absolute concentration of the component peptide isotopologues. Because the protein or polypeptide to be quantified differs with each experiment, the internal standard for this protein or polypeptide necessarily also differs with each experiment, and requires that amino acid analysis be performed with each experiment. Each quantitation requires a dilution curve that typically encompasses six points, which may be accomplished in one high resolution MS analysis through the use of AQUAplex internal standard isotopologues mixed at a define ratio to provide a standard curve. The costs for amino acid analysis are relatively high and the procedure is time consuming. Each peptide sequence has specific solubility, and its non-specific binding constant varies based upon various factors that may differ with each analysis, e.g., vessel material, buffer, temperature, etc. Such variability decreases precision and reproducibility.

In contrast, with peptides as a non-limiting example, the AQUAplex inventive method using a modified, optimized, labeled universal reporter isotopologue mixture Uplex, and one analyte, more than one analyte, or several concatenated analytes, increased the analytical precision of quantitation where quality of internal standards is decisive to ensure precise quantification. Only this universal reporter Uplex undergoes amino acid analysis, rather than an internal standard for each peptide to be quantified requiring amino acid analysis. This universal reporter is a mixture of isotopologues, permitting the full dilution curve to be acquired in one MS acquisition. Universal reporter isotopologue Uplex quantification thus need be performed only once, rather than with each experiment, and can be used to quantify a reporter peptide with a standard curve. The universal reporter Uplex can be stocked and made readily available. In one embodiment, universal reporter Uplex is labeled with a fluorophore and/or chromophore, and universal reporter Uplex is quantified by measuring the absorbance of the fluorophore and/or chromophore, and the relative proportion of the isotopologues, and thus absolute concentration of the isotopologues, is determined by high resolution MS. For peptide analytes, no amino acid analysis is required. In one embodiment, universal reporter peptide Uplex contains one tryptophan, and universal reporter peptide Uplex is quantified by measuring absorbance using the specific extinction factor of the tryptophan to determine the total peptide concentration with high resolution MS to determine the component isotopologue concentrations.

As shown in FIG. 12 using a peptide analyte, in one embodiment peptide A*, the internal standard, is linked with a reporter peptide R through a cleavable site (e.g., proteolytic site) between A* and R. In this embodiment, each of peptide A* and reporter peptide R contain at least one amino acid labeled with a heavy isotopologues, known as heavy amino acids. When peptide A* is labeled with an isotopologue set, the target analyte may be quantified by AUC comparison to the A* internal standard in low MS resolution or the target analyte may be quantified by AUC comparison to the A* isotopologue set with high MS resolution. Alternatively, when reporter peptide R is labeled with a heavy isotope, reporter peptide R may be labeled with an isotopologue set so that it can be quantified by comparison to a universal reporter peptide U or universal reporter peptide isotopologue set Uplex. Because the universal reporter peptide isotopologues Uplex must have a different mass, universal reporter peptide Uplex can be represented with two heavy amino acids or their isotopologues, and reporter peptide R one heavy amino acid or its isotopologues. There are other ways to obtain a difference in atomic mass; e.g., using different heavy amino acids for reporter peptide R and universal reporter peptide Uplex to obtain a difference in atomic mass, using different isotopologues in reporter peptide R and universal reporter peptide Uplex, or using multiple unique isotopologues in reporter peptide Rplex and in universal reporter peptide Uplex. In this manner, the concept of AQUAplex isotopologues may be applied to improve quantitation of a target peptide with A* isotopologues, to improve quantitation of reporter peptide R with Rplex isotopologues, and/or to improve quantitation of reporter peptide R with Uplex isotopologues.

Peptide A* has the same sequence as proteotypic peptide A, but peptide A* has a different mass due to the presence of the heavy amino acid or heavy amino acid isotopologues as peptide A*plex. Universal reporter peptide Uplex is a peptide standard isotopologue set for reporter peptide R. Universal reporter peptide Uplex isotopologues are not the internal standard used to quantify the protein or polypeptide. Universal reporter peptide Uplex has the exact same sequence as reporter peptide R but has a different atomic mass due to the incorporation of one or more heavy amino acid isotopologues.

In the ligation between peptide A* and reporter peptide R, resulting in a polypeptide, the reporter peptide R can be C-terminal to A*, i.e., R-A*, or the reporter peptide R can be N-terminal to A*, i.e., A*-R. One or both of A* and R may be an isotopologue set, A*plex and Rplex, that can be resolved and quantified by high resolution MS. The nomenclature A*-R is used to represent either the A*-R polypeptide or the R-A* polypeptide. In either case when A* is a proteotypic peptide, there must be a cleavable (e.g., proteolytic) site between peptide A* and reporter peptide R in the resulting polypeptide.

The polypeptide isotopologue set A*plex-R is mixed with the sample that contains the protein or polypeptide P to be quantified. A known quantity of universal reporter peptide Uplex isotopologues is added to the sample, i.e., universal reporter peptide Uplex is spiked into the sample. The sample is digested with a protease (e.g. trypsin) that cleaves the polypeptide bonds. As a result of protease action, polypeptide A*-R must be fully digested. In one embodiment, universal reporter peptide or Uplex is added before cleavage (e.g., proteolytic digestion). In one embodiment, universal reporter peptide or Uplex is added after cleavage (e.g., proteolytic digestion).

After digestion the concentration of peptide A*plex and reporter peptide R in the sample is equimolar. That is, the quantity of peptide A* is equal to the quantity of reporter peptide R. Universal reporter peptide Uplex isotopologues are used to quantify reporter peptide R using high resolution MS quantitation. The standard curve of peptide A*plex is used to measure the quantity of peptide A in the sample resulting from the proteolytic digestion of protein or polypeptide P.

Figure 13:
FIG. 13 schematically shows an embodiment for quantitation of more than one peptide, each peptide linked to a separate reporter peptide R, in which each peptide and reporter peptide is labeled with heavy amino acids or heavy amino acid isotopologues.
Figure 13:
Figure 13:
Figure 13:
Figure 14:
FIG. 14 schematically shows an embodiment with three concatenated heavy peptide isotopologue sets linked to a single reporter peptide R.

In the embodiment using a peptide shown in FIGS. 13 and 14, the same method is applied to proteotypic peptides B and C from protein P in order to increase the specificity of the quantitation. Peptide B*plex has the same sequence as proteotypic peptide B but has a different atomic mass due at low MS resolution and is a dilution series of peptide B* at high MS resolution to the presence of the heavy isotopologue labeled amino acids. Peptide C*plex has the same sequence as proteotypic peptide C but has a different atomic mass at low MS resolution and is a dilution series of peptide B* at high MS resolution due to the presence of the heavy isotopologue labeled amino acids.

Using a peptide embodiment as an example, A*plex-R includes a cleavage site (e.g., proteolytic site) between isotopologue set A*plex and R. Polypeptide isotopologues A*plex-R thus can be used as a pseudo-surrogate of protein or polypeptide P to monitor proteolytic digestion in a single experiment, digestion efficiency among samples and experiments, and in some cases to normalize results from different samples and/or different experiments.

Figure 15:
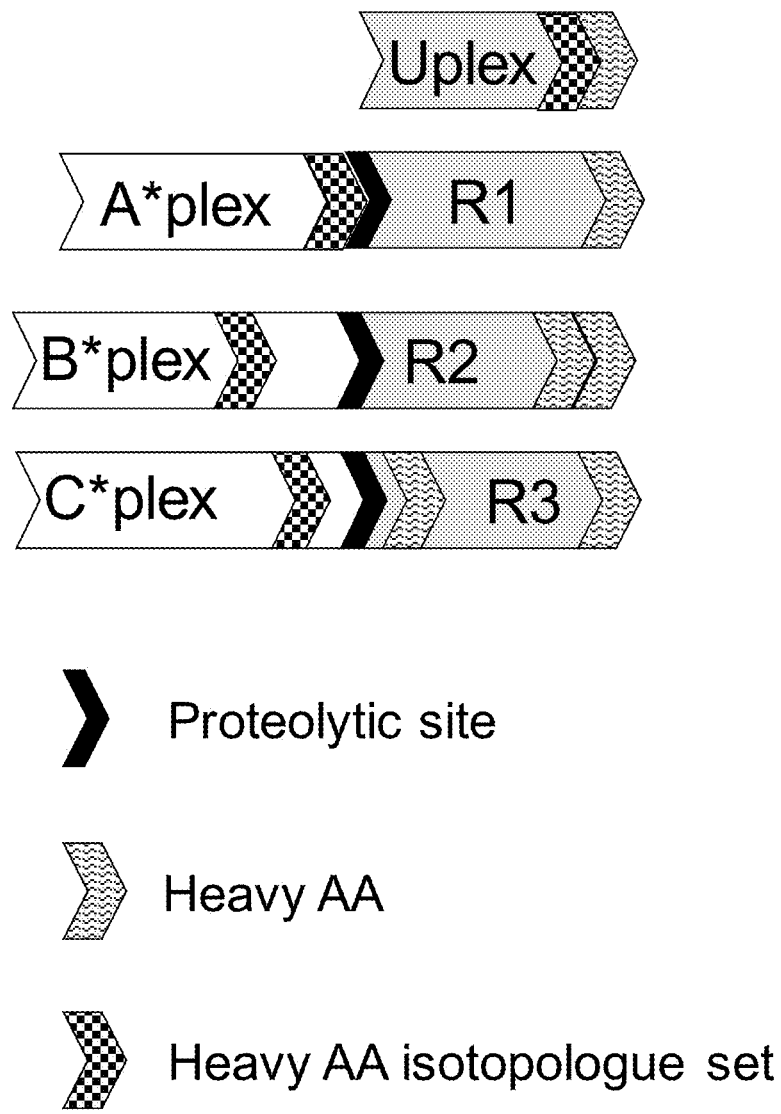
FIG. 15 schematically shows an embodiment for simultaneous assay of more than one analyte in a sample using a single assay (multiplexing) where three proteotypic peptide isotopologue sets, each cleavably linked to its own reporter peptide R and correlated to a single universal reporter peptide Uplex isotopologue set.

In examples using peptides, reporter peptide R can be optimized for proteolytic digestion. As one example, reporter peptide R can be selected and/or modified so that it contains a specific amino acid (e.g., tryptophan) that is easily quantified by absorption measurements. As shown in FIG. 15, reporter peptide R may contain more than one heavy isotope labeled amino acid or a distinct isotopologue for a single heavy amino acid. This embodiment increases the multiplexing possibilities of the method by increasing the number of possible atomic masses for the same reporter peptide R sequence, so that multiple peptides can be quantified using universal reporter peptide U in a single experiment.

In this multiplexing embodiment, reporter peptide R is synthesized with different atomic masses, using standard methods known in the art. As shown in FIG. 15, peptides A, B, and C from protein or polypeptide P are quantified in a single experiment using heavy peptides A*plex, B*plex, and C*plex, respectively, and using reporter peptides R1, R2, R3. In the embodiment shown in FIG. 15, reporter peptides R1, R2, R3, and universal reporter peptide U, have the same sequence but different atomic masses. To maximize the number of mass combinations available for reporter peptide R, the sequence may be composed of, but is not limited to, one or more of the following amino acids: alanine, arginine, isoleucine, leucine, lysine, phenylalanine, proline, and valine. These amino acids have a mass shift ≥4 Da and can be synthesized with different combinations of heavy isotopes to make isotopologues, such as in FIGS. 6-9. The minimum mass difference between the proteotypic peptide (e.g., A), and the internal standard (e.g., A*), should exceed the sensitivity threshold determination for MS differentiation. In one embodiment, the minimum mass difference between the proteotypic peptide and the internal standard is 4 kDa when 4 kDa is the minimum atomic mass difference that can be discriminated. In one embodiment, the minimum mass difference between the internal standard, reporter peptides, and universal reporter isotopologues is 6 mDa when 6 mDa is the minimum atomic mass difference that can be discriminated by high resolution MS. The number of peptides that can be quantified simultaneously using a universal heavy peptide U is limited only by the number of mass difference combinations available within the sequence.

In another example using peptides, reporter peptide R may be designed with a low hydrophobicity index, which will increase the aqueous solubility of the polypeptide A*plex-R where peptide A*plex is a set of isotopologues with a hydrophobicity index≥40 or where peptide A*plex is poorly soluble. One example of a reporter peptide R having a sequence that renders it highly soluble is PVVVPR (SEQ ID NO. 1); it has a hydrophobicity index of 13.45. One example of a reporter peptide R having a sequence that renders it highly soluble is SSAAPPPPPR (SEQ ID NO. 2) with a hydrophobicity factor of 7.57. In one example, each of reporter peptide R and universal reporter peptide Uplex isotopologues contains a chromophore and/or fluorophore used for quantification by absorbance measurement. In the embodiment where both universal reporter peptide U and reporter peptide R include a chromophore and/o fluorophore, universal reporter peptide Uplex isotopologues can be quantified by measuring the absorption of the chromophore and/or fluorophore, and not by amino acid analysis, and the isotopologues may be quantified by high resolution MS. The process of protein or polypeptide quantification by absorbance is more robust than the process of amino acid analysis. Protein or polypeptide quantification by absorbance is considered more precise than protein or polypeptide quantification by amino acid analysis. Examples of a chromophore or fluorophore and methods of assessing their absorbance are known in the art.

In the embodiment shown in FIG. 14, the polypeptide contains three prototypic peptides, each labeled with a heavy amino acid, concatenated with a single reporter peptide R also labeled with a heavy isotope amino acid, resulting in C*plex-B*plex-A*plex-R. Using this polypeptide C*plex-B*plex-A*plex-R guarantees equimolar quantities of each of peptides A*plex, B*plex and C*plex, and each isotopologue set provides a standard curve for peptides A, B, and C, and thus decreases quantitation variability compared to quantitation using individual peptides. This embodiment increases the number of peptides that can be quantified with the same sequence as that of universal reporter peptide U.

In one embodiment, A*plex-R, or B*plex-A*plex-R, or C*plex-B*plex-A*plex-R can be cleaved before being introduced into the sample to be quantified.

In embodiments using proteotypic peptides, peptides A*plex, B*plex, C*plex, and reporter peptide R can be randomly arranged, as long as they are linked through a cleavage site (e.g., proteolytic site).

The polypeptide shown in FIG. 14 contains three heavy isotope labeled peptides (A*plex, B*plex, and C*plex), corresponding to target peptides A, B, and C, linked to reporter peptide R, also containing a heavy isotope label. Other embodiments are possible where R does not contain a heavy isotope label or contains one or more isotopologues that allow multiple distinct reporter isotopologues to quantify multiple unique internal standard peptides in a multiplexed assay. Other embodiments are possible that contain various numbers (n) of labeled peptides and their isotopologues corresponding to one or more target peptides, joined with one or more reporter peptides and isotopologues. The range for n is governed by, e.g., manufacturing feasibility, solubility, etc. as known to one skilled in the art. In one embodiment, a value of n up to 99 is possible. In one embodiment, a value of n up to 49 is possible. In one embodiment, n=4. In one embodiment, n=5. In one embodiment, n=6. In one embodiment, n=7. In one embodiment, n=8. In one embodiment, n=9. In one embodiment, n=10. In one embodiment, n=11. In one embodiment, n=12. With isotopologues these limits increase dramatically; one can use a combination of different heavy amino acids, isotopic shifts, and isotolopologues.

Universal reporter peptide U and reporter peptide R can be designed with different sequences and isotopologues for multiplex quantitation. The number of mass difference combinations determined by a peptide sequence is limited. When the number of peptides to be quantified exceeds the maximum number of mass difference combinations available for reporter peptide R, one can use additional isotopologues of universal reporter peptide U, and one can use additional sequences: e.g., $U^1, U^2, \ldots U^n$ where n is limited only by the number of peptides that can be simultaneously quantified by an instrument. As one example, the polypeptide A*-Rplex may have the amino acid sequence TTVSKTETSQVAPA SEQ ID NO. 3, with peptide A* having the sequence TETSQVAPA SEQ ID NO. 4, and reporter peptide Rplex having resolvable lysine isotopologues from FIG. 6 of the sequence TTVSK SEQ ID NO. 5, as disclosed in WO/2003/046148.

Because the sequence of universal reporter peptide Uplex isotopologue set is not restricted or limited, and because universal reporter peptide Uplex isotopologue set is a product that can be readily ordered, stocked, maintained, and inventoried, its use provides flexibility to MS peptide quantitation. In one embodiment, the sequence of universal reporter peptide Uplex isotopologue set can be customized to minimize non-specific binding of the peptide, polypeptide, or protein to, e.g., a vessel, tips, tubing, etc. by selecting a sequence with a low hydrophobicity index, e.g., PVVVPR SEQ ID NO. 1 which has a hydrophobicity index of 13.45 or SSAAPPPPPR (SEQ ID NO. 2), which has a hydrophobicity index of 7.57, and using multiple arginine isotopologues or isotopologues of other heavy amino acid precursors (FIGS. 9, 10a-b). In one embodiment, the sequence of universal reporter peptide Uplex isotopologue set can be customized to maximize solubility of the polypeptide A*plex-R. For example, because universal reporter peptide U is used, the polypeptide A*plex-R need not be quantified precisely prior to MS analysis, and the use of isotopologues premixed at a defined ration in the synthesis provides multiple data points across a dilution curve for improved quantitation. This results in shorter manufacturing time and lower cost in producing polypeptide A*plex-R. Peptide A*plex is quantified at very low concentration, at which its solubility is guaranteed, resulting in enhanced precision and repeatability.

Because quantitation of peptide A*plex is performed on the same instrument used for the quantitation of reporter peptide R and within the same MS procedure, it always reflects the quantity added into the sample and is independent of eventual alteration, degradation, and partial loss of polypeptide A*plex-R during sample preparation, fractionation, and liquid chromatography separation prior to MS quantitation. When extending the method described in WO 03/016861, the A*plex isotopologue set is provided in a known concentration that is too high for use without dilution; thus, it is typically diluted 1000 to 10,000. If the sequence of A*plex is relatively hydrophobic and prone to non-specific binding, as is the case for β-amyloid peptides, a significant amount of the standard will be lost during dilution. This decreases the method's precision. Because the sequence of universal reporter peptide Uplex isotopologue set can be designed and optimized to decrease non-specific binding, the dilution of universal reporter peptide U is not prone to significant non-specific binding. Universal reporter peptide Uplex isotopologue set is included in the sample to be quantified, and quantitation of reporter peptide R is performed in the diluted sample, thus non-specific binding of the standard (e.g., β-amyloid peptide) will not decrease the method's precision.

The polypeptide A*plex-R is a pseudo-surrogate of protein P and can be used to monitor cleavage (e.g., proteolytic digestion). It can be used to quantify and compare sample-to-sample, and/or experiment-to-experiment, digestion efficiency, as the dilution curve provided by a defined isotopologue set provides accurate quantitation across a broad dynamic range. It can be used to normalize results from sample-to-sample, and/or from experiment-to-experiment.

In one embodiment, the inventive method is adapted to MS quantitation of analytes, including but not limited to peptides, polypeptides, and proteins, using a proteotypic peptide that is coupled, through a cleavable site, to a reporter peptide R or other moiety. This is shown schematically in FIG. 16 for any analyte, and in FIG. 17 for a peptide analyte. The heavy proteotypic peptide isotopologue set contains the same amino acid sequence, but different atomic masses, as the native proteotypic peptide. Each heavy proteotypic peptide isotopologue in the set is in equimolar concentration with the reporter peptide R. In one embodiment, reporter peptide R is labeled with a heavy isotope or set of isotopologues. In one embodiment, reporter peptide R is not labeled with a heavy isotope. Universal reporter peptide U has the same sequence as reporter peptide R. Universal reporter peptide U has a different mass than reporter peptide R because it contains a heavy set of isotopologues. Only universal reporter peptide Uplex is quantified. After cleavage (e.g., proteolytic digestion), the heavy proteotypic peptide or isotopologue set and the reporter peptide R are released at equimolar concentration into the sample. The quantity of the reporter peptide R is determined using the quantity of heavy universal reporter peptide Uplex isotopologue set.

Universal reporter peptide Uplex isotopologue set is sequence independent and is used as a quantitation standard and a cleavage standard. Universal reporter peptide Uplex isotopologue set has a peptide sequence that is identical to reporter peptide R but is independent from the protein to be assayed. Because the sequence of universal reporter peptide Uplex isotopologue set and reporter peptide R is identical, the atomic mass difference between universal reporter peptide Uplex isotopologue set and reporter peptide R is obtained using a heavy labeled reporter peptide R and a heavy labeled universal reporter peptide Uplex isotopologue set. The atomic mass difference is obtained by using different heavy labels in reporter peptide R and universal reporter peptide Uplex isotopologue set, or by using an additional heavy amino acid in reporter peptide R or universal reporter peptide Uplex isotopologue set (FIG. 15). Reporter peptide R may have a lower atomic mass or a higher atomic mass than universal reporter peptide Uplex isotopologue set.

Figure 18:
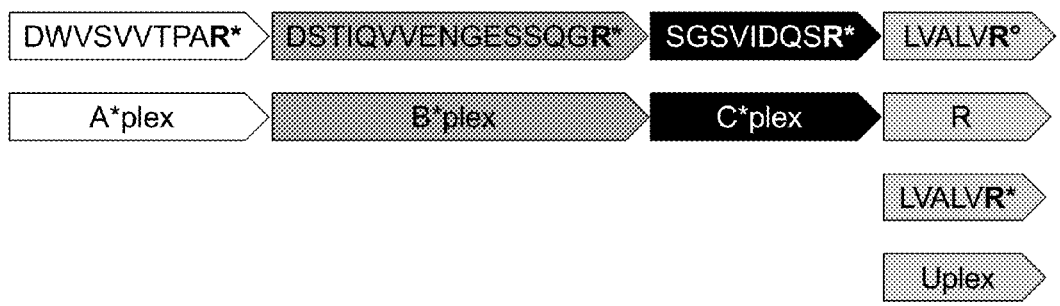
FIG. 18 schematically shows a naming convention with SEQ ID NOS. 22-25.

As represented in FIG. 18, a convenient convention for naming components is as follows: proteotypic peptides are named as letters, e.g., A, B, C; heavy isotope labeled proteotypic peptides are named as letters with an asterisk indicating a heavy isotope label and the "plex" suffix to reflect the use of multiple isotopologues, e.g., A*plex, B*plex, C*plex; R is a reporter; Uplex is a universal reporter isotopologue set; the amino acid bearing the heavy isotope label is indicated by a degree symbol and either conventional amino acid one- or three-letter naming in bold font, e.g., either R or Arg indicates the amino acid arginine with a heavy isotope label; the amino acid bearing the set of heavy isotopologue labels is indicated by an asterisk symbol "*" and either conventional amino acid one- or three-letter naming in bold font, e.g., either R\* or Arg\* indicates the amino acid arginine with one or more heavy isotopologue labels; one composition of concatenated peptides and universal reporter, commercially available under the trademark HeavyPeptide IGNIS™, is A*plexB*plexC*plexR.

In one embodiment, the sequence of universal reporter peptide Uplex isotopologue set is optimized and/or customized to be compatible with the properties of the proteotypic peptide by optimizing chromatographic ionization and fragmentation properties. As one example, universal reporter peptide Uplex isotopologue set is modified to enhance ionization and/or desolvation by introducing additional charge or hydrophobic properties. As one example, universal reporter peptide Uplex isotopologue set is modified to enhance fragmentation by introducing an aspartate-proline (DP) group that contains a highly scissile bond that fragments in tandem MS at lower collisions energies than other dipeptide linkages. As one example, universal reporter peptide Uplex isotopologue set is modified to have a similar retention time on liquid chromatography as the proteotypic peptide by choosing a reporter peptide with a similar hydrophobicity factor to the proteotypic peptide. Thus, universal reporter peptide Uplex isotopologue set can be optimized by design. For example, the number of mass combinations and isotopologues for the identical peptide sequence can be optimized to increase the multiplexing capacity, yielding up to 500 proteins capable of being quantified in a single assay. Yet because the peptide sequences are identical, the full set of isotopologues can be resolved with high MS resolution at MS1 or MSn levels, and the peptide sequence can be verified by MS/MS or MSn fragmentation at low MS resolution, only one dilution curve is required to quantify universal reporter peptide U. By increasing the number of identical sequences with different masses and isotopologues, the number of proteins that can be quantified in a single experiment increases, without concomitant increase in instrumentation use and resources.

In one embodiment, the universal reporter peptide Uplex isotopologue set was optimized for low specific binding, high solubility, high MS signal intensity, and/or desired liquid chromatography retention time. In one embodiment, the universal reported peptide Uplex isotopologue set peptide sequence was modified to change its chromatographic retention properties; this is one example of internal modification. In one embodiment, the universal reporter peptide Uplex isotopologue set structure was modified by attaching tags to change its chromatographic retention properties; this is one example of external modification. In one embodiment, the universal reporter peptide Uplex isotopologue set structure was modified by attaching tags that themselves had been modified to change its chromatographic retention properties; this is another example of external modification.

In one embodiment, a universal isotopologue polymer set is used, where polymer is broadly defined as a joined group of monomers. The monomers either need not be peptides, or need not be entirely peptides, and may contain one or more isotopes. In one embodiment, polysaccharides (i.e., glycan monomers) are used as universal polymers ($U^{polymer}$). A polysaccharide is a combination of two or more monosaccharides linked by glycosidic bonds, and the polysaccharide is synthesized from a set of monomers such as to produce an isotopomer set. Examples of such polysaccharides include isotopologues of starch, cellulose, and glycogen. Their structures and synthesis are know in the art. In one embodiment, deoxyribonucleic acid (DNA) or ribonucleic acid (RNA) isotopologue sets are used as universal polymers ($U^{polymer}$). Their structures and synthesis are known in the art. Methods to detect and quantify nucleotides are well established, e.g., PCR, quantitative PCR. Nucleotides attached to an analyte can by used as a unique identifier (i.e., "barcode") of the analyte and for quantitation purposes using high resolution MS with isotopic dilution of the isotopologue set.

In one example, isotopologues of one of the following peptide sequences shown in the table below, currently used as retention time calibrator peptides, were used as a universal reporter peptide Uplex isotopologue set. These peptides exhibited sufficient ionization and had defined elution properties. The following table below shows their sequence, hydrophobicity, and chromatograph behavior on a Hypersil Gold $C_{18}$ column.

| Peptide | SEQ ID No. | Hydrophobicity Factor | Retention Time (min) |
|---|---|---|---|
| SSAAPPPPPR | 2 | 7.57 | 4.77 |
| GISNEGQNASIK | 6 | 15.50 | 6.62 |
| HVLTSIGEK | 7 | 15.52 | 7.22 |
| DIPVPKPK | 8 | 17.65 | 7.67 |
| IGDYAGIK | 9 | 19.15 | 8.18 |
| TASEFDSAIAQDK | 10 | 25.88 | 9.01 |
| SAAGAFGPELSR | 11 | 25.24 | 9.41 |
| ELGQSGVDTYLQTK | 12 | 28.37 | 9.63 |
| SFANQPLEVVYSK | 13 | 34.96 | 10.67 |
| GLILVGGYGTR | 14 | 32.18 | 10.79 |
| GILFVGSGVSGGEEGAR | 15 | 34.52 | 10.86 |
| LTILEELR | 16 | 37.30 | 11.87 |
| NGFILDGFPR | 17 | 40.42 | 12.16 |
| ELASGLSFPVGFK | 18 | 41.19 | 12.21 |
| LSSEAPALFQFDLK | 19 | 46.66 | 12.85 |

Hydrophobicity was determined using calculations done with algorithms described in Spicer. et al (2007). Sequence-specific retention calculator. A family of peptide retention time prediction algorithms in reversed-phase HPLC: applicability to various chromatographic conditions and columns. Anal Chem. 79(22):8762-8.

In one embodiment, the heavy isotopomeric label is incorporated in the C-terminal amino acid. For example, using the peptide SSAAPPPPPR SEQ ID NO. 2, this embodiment can be represented as SSAAPPPPPR*, where the terminal R contains the heavy isotope label incorporated as a set of isotopologues resolvable with high resolution MS.

In one embodiment, the heavy isotope is incorporated in the peptide at a position other than the C-terminus. One or more of the following amino acids may be labeled with a heavy isotopologue set: alanine, arginine, isoleucine, leucine, lysine, phenylalanine, valine (FIG. 8). These amino acids have a mass shift >4 Da. Additionally, multiple amino acids within the peptide can be labeled with isotopologue sets, and the same amino acid may be labeled with different isotopes, such as arginine +6 Da and arginine+10 Da isotopologue sets which would introduce a 6 Da and 10 Da mass shift, respectively at low MS resolution, and with additive multiplexing capability at high resolution MS (FIGS. 7a-b). For example, using the peptide SSAAPPPPPR SEQ ID NO. 2 where * indicates the amino acid containing the position of the heavy isotope label, the following positions are possible: SSA*APPPPPR, SSA*A*PPPPPR, SSA*A*P*PPPPR, SSA*A*P*P*PPPR, SSA*A*P*P*P*PPR, SSA*A*P*P*P*P*PR, SSA*A*P*P*P*P*P*R, SSA*A*P*P*P*P*P*R*. This embodiment, where the heavy isotopologue amino acid is located at one or more positions, permits higher multiplexing with the same reporter sequence.

For multiplexed assays, custom peptides are combined together into complex targeted assays. Each custom peptide has a different corresponding universal reporter Uplex isotopologue set that elutes similarly to the custom peptide. This permits many peptides to be easily multiplexed and quantified across an LC gradient without cross contamination. For example, a multiplex analysis array contains any number of different universal peptides Uplex isotopologue sets having the same amino acid sequence, but a different atomic mass due to the presence of a heavy isotopologue or isotopologue set, and a number of reporter peptides R, each reporter peptide R cleavably linked to a different isotopically labeled proteotypic peptide to be quantified in a sample. The universal peptide Uplex isotopologue sets have substantially similar chromatography retention time as the custom peptide. In one embodiment, the heavy isotopologue labels in the universal reporter peptide Uplex isotopologue set is incorporated at multiple different amino acids. This embodiment permits higher multiplex arrays using the same universal reporter peptide Uplex amino acid sequence.

In one embodiment, the universal reporter peptide Uplex isotopologue set is customized for a specific mass spectrometer and/or specific use for identification, characterization, and quantitation of disease biomarkers (proteomics, metabolomics, pharmacoproteomics) discovery, confirmation, validation, and early clinical diagnosis and disease progression monitoring. For example, a 4-10 amino acid reporter peptide will allow incorporation of fewer isotopologue precursors and lower multiplexing capability with high resolution MS. Alternatively, a larger 11-25 amino acid peptide could allow incorporation of more isotopologue precursors and lower multiplexing capability with a high resolution mass spectrometer. Proteomics has advanced from identification (qualitative proteomics) to quantitation by incorporating an internal standard in the assay. An internal standard is required because the resulting peak height or peak surface in mass spectroscopy results from a complex function of parameters (e.g., peptide quantity, peptide ionization, peptide fragmentation, ion suppression, etc.). There is no algorithm to measure the quantity of a peptide from the surface of the mass spectroscopy peak. When a known quantity of the internal standard is added to the peptide to be analyzed, the quantity of the peptide is determined by comparing its peak surface with the internal standard peak surface.

One embodiment is a described peptide modified with a tag. Such a tag, used to modify the peptide, differs from the heavy isotope label that is required or is optional to modify universal reporter U and reporter R, respectively. The tag, however, may be a heavy isotopologue set, as subsequently described in the first example.

One example of such a tag is a heavy isotopologue set. One example of such a tag is an isotopologue tag. Such tags include forms of the same chemical structure with each tag having a unique isotopologue that can be resolved with high resolution MS.

One example of such a tag is a different isotopologue of the same peptide. This example uses as a tag an element that naturally has multiple isotopes, and where the isotopes have a unique mass defect.

Use of a mass defect tag shifts the reporter peptide to a region of the mass chromatogram in which most isotopes are not observed, sometimes referred to as a mass quiet space. This example is useful to enhance sensitivity and specificity of detection in a mass region with many other background ions.

Stable isotope labeling with amino acids in cell culture (SILAC) and its variations, known to one skilled in the art, uses mass spectrometry to quantitate and compare proteins among samples, and sample normalization and measurement of biological variation with structural proteins, chaperones, or housekeeping enzymes allows large numbers of samples to be processed and compared. Isobaric labeling using either tandem mass tags (TMT) or isobaric tags for relative and absolute quantitation (iTRAQ) uses mass spectrometry to quantitate and compare proteins for quantitation of peptides from proteins in cell and tissue lysates, serum and plasma, and formalin-fixed paraffin embedded tissue slices. TMT and iTRAQ have the general structure M-F-N-R where M=mass reporter region, F=cleavable linker region, N=mass normalization region, and R=protein reactive group. Isotopes substituted at various positions in M and N cause each tag to have a different molecular mass in the M region with a corresponding mass change in the N region, so that the set of tags have the same overall molecular weight. Only when the TMT undergo a second or third fragmentation (such as in tandem mass spectrometry MS/MS, or triple mass spectroscopy MS/MS/MS) are they distinguishable, with backbone fragmentation yielding sequence and tag fragmentation yielding mass reporter ions needed to quantitate the peptides. iTRAQ and TMT covalently label amine groups in protein digests and a cysteine reactive TMT labels thiols of cysteines, resulting in individual digests with unique mass tags. The labeled digests are then pooled and fragmented into peptide backbone and reporter ions. The peptide backbone ions are used to identify the protein from which they came. The reporter ions are used to quantify this protein in each of the combined samples.

Label-free SILAC, TMT, iTRAQ, and other mass spectroscopy methods known to one skilled in the art of protein quantitation are used in biomarker discovery to generate candidate markers on instrumentation that includes LTQ Velos (Thermo Scientific), LTQ Orbitrap Elite (Thermo Scientific), and Q Exactive (Thermo Scientific) hybrid mass spectrometers. The candidate markers are then further evaluated and applied in targeted analysis assays using selected reaction monitoring (SRM) or selected ion monitoring (SIM) to target quantitation of peptide markers in many samples. For confirmation and validation, the universal reporter peptide U is customized for use, as explained below, with the markers that were previously identified, for absolute quantitation with synthetic stable-isotope-labeled peptide standards (HeavyPeptide AQUAplex and its variations, Thermo Scientific) using existing discovery data to automate the preliminary selection for targeted analysis (Pinpoint software (Thermo Scientific); TSQ Vantage triple stage quadrupole mass spectrometer (Thermo Scientific)). The data are entered into an integrated data management system for clinical applications.

One embodiment is a universal reporter peptide Uplex isotopologue set synthesized to provide it with similar (e.g., ±10% to 20%) properties (e.g., retention time, ionization, optimal fragmentation energy, limit of detection, digestion efficiency, etc.) to a custom peptide. In a method using this embodiment, the universal reporter peptide Uplex isotopologue set is used to assess digestion efficiency. In use, this embodiment permits one to assess the proteotypic peptide and both the undigested and digested custom peptide and the universal reporter peptide Uplex isotopologue set. The efficiency of digestion of the custom and universal peptide to the individual peptides is then used to correct the level of proteotypic peptide quantified, allowing more accurate absolute quantitation of the protein of interest and more accurate quantification between samples by correcting for digest efficiency between samples.

One embodiment is a set of universal peptides Uplex isotopologue set. This set of universal peptides Uplex isotopologue set co-elutes in a predictable manner. The peptides in the set may or may not share a common sequence. The peptides in the set have stable isotopologue sets incorporated at unique positions to enable specific quantitation of each.

One embodiment is a universal isotopologue peptide set compound, composition, formulation, and/or kit. In one embodiment, the heavy isotopologue proteotypic peptide set-reporter peptide R can be formulated dry. In one embodiment, the heavy isotopologue proteotypic peptide set-reporter peptide R can be formulated in solution. The heavy isotopologue proteotypic peptide set-reporter peptide R is stabilized and solubilization is facilitated by formulating it with a non-reducing sugar (e.g., sorbitol, mannitol, etc.), using methods known to one skilled in the art. In this form, it is stable at attomole or femtomole quantities. In one embodiment, the heavy isotopologue proteotypic peptide set-reporter peptide R is formulated as a tablet that could be transported and stored at ambient temperatures and would be easily transferred to vials with the need for liquid measurement. This format eliminates concerns about peptide binding nonspecifically to a tube wall or solvent evaporation resulting in changes in peptide concentration. This embodiment reduces the number of manipulations required and, hence, decreases error. This embodiment facilitates automation.

EXAMPLE 1

Stable isotope labeled peptides containing a universal reporter peptide Uplex isotopologue set at a predetermined ratio of isotopologues and several peptides concatenated together with a reporter peptide are applied to detect and quantify protein biomarkers in clinical samples, with a focus on markers of lung cancer.

To assess the recovery of the sample preparation method, heavy isotopologue labeled synthetic polypeptide standards (comprising up to three proteotypic peptides and a universal reporter R) of human plasma proteins (LDH, NSE, and Myo) are spiked in samples before and after proteolysis. HPLC-MS analyses are performed on a hybrid mass spectrometer instrument (Q Exactive, ThermoFisher Scientific) in SIM mode. A set of concatenated reference peptides is synthesized based on a list of candidates previously identified. Synthetic polypeptides are obtained from ThermoFisher Scientific (Ulm Germany).

The reporter peptide R is designed with a tryptic cleavage site at the C-terminus. The isotopologue calibration curve standards for the universal reporter Uplex peptides are established during peptide synthesis through the use of a mixture of the isotopologue amino acid precursors at a pre-defined ratio. The relative response factor of each targeted analyte peptide compared to the reporter is readily determined after trypsin treatment by exploiting the 1:1 stoichiometry of the reporter: targeted analyte concatenated peptide.

A panel of proteins indicative of lung cancer is selected to demonstrate proof-of-principle. For precise quantification of specific proteins, three synthetic concatenated proteotypic polypeptide isotopologue mixtures, R:A*plex, R:B*plex, and R:C*plex, are generated and analyzed. Plasma samples from lung cancer patients and controls are analyzed.

The concatenated synthetic polypeptides containing a universal reporter enables precise determination of the amounts of targeted proteins present in the sample using concomitantly multiple reference peptides. The absolute amount of the reporter peptide (R) released during proteolysis is determined with high resolution MS by comparing the AUC to that of the universal reporter internal standard Uplex. The absolute amount of the target analyte peptides A, B, C in the sample is determined with high resolution MS by comparing the AUC of each target peptide to that of the isotopologue internal standard peptide A*plex, B*plex, and C*plex, respectively. This quantification approach is readily implemented in a large scale targeted proteomics workflow.

EXAMPLE 2

Stable isotopologue labeled peptides containing a universal reporter peptide R and several concatenated targeted analyte peptides are used to detect and quantify protein biomarkers in clinical samples, with a focus on markers of bladder cancer.

Exogenous proteins from yeast (*Saccharomyces cerevisiae*) (ADH, *enolase*, and carboxypeptidase) and human (LDH, NSE, Myo) are added as internal standards in urine samples. The isotopologue labeled synthetic polypeptide standards, which are proteotypic peptides of the protein of interest concatenated with a universal reporter peptide R, are spiked before proteolysis. Urine samples are prepared by protein precipitation, reduction/alkylation, trypsin proteolysis, and desalting using C18 cartridges. A second set of isotopically labeled synthetic peptides is added after proteolysis.

LC-MS/MS analyses are performed on RP-HPLC (Dionex) coupled with a hybrid high resolution MS instrument (Q Exactive, ThermoFisher Scientific) operated in multiplexed selected ion monitoring (mxSIM) mode. Synthetic polypeptide heavy isotopologues are obtained from ThermoFisher Scientific (Ulm Germany).

To establish the methodology, stable isotope-labeled dipeptides containing targeted peptide heavy isotopologues and a universal reporter R are synthesized. The reporter peptide R is designed with a tryptic cleavage site at the C-terminus. The calibration curves for the universal reporter peptides Uplex are established using the predetermined mixture of amino acid precursor isotopologues in the peptide synthesis. In parallel, the relative response factor of each peptide compared to the reporter is determined after trypsin treatment exploiting the 1:1 stoichiometry. LC-MS analyses are performed in multiplexed SIM mode (mxSIM).

To evaluate the methodology, precise quantities of reference polypeptides are spiked into the urine samples, digested with trypsin, and analyzed by LC-mxSIM to quantify the targeted human proteins. Preliminary results include analysis of insulin-like growth factor binding protein 7 in urine samples using two individual synthetic stable isotope-labeled peptide isotopologue sets with a universal reporter R: reporter-HEVTGWVLVSPLSK* (SEQ ID NO. 20) and reporter-ITVVDALHEIPVK* (SEQ ID NO. 21, *-isotopologue residue). Dilution curves are generated in pooled urine samples to precisely determine the quantity of corresponding protein.

EXAMPLE 3

To further evidence the method's utility, large synthetic polypeptides are produced, resulting from concatenation of multiple peptides representing each of the proteins of interest. Three proteotypic peptides per protein with adequate mass spectrometric properties (precursor m/z, ionization efficiency, retention time, MS/MS spectra) are selected to construct the concatenated standards. These reference polypeptides, all containing a universal reporter, allow measurement of the precise amount of multiple reference peptides in one LC-MS run.

EXAMPLE 4

The inventive method decreases peptide synthesis cost and mass spectrometry usage to generate a calibration curve, resulting in savings in instrument usage, operator time, and processing efficiency. To further reduce the cost of peptide synthesis, one internal standard peptide is synthesized with no heavy isotope, and this peptide is labeled with a set of six amine-reactive triazine-based mass tag reagent isotopologues premixed at two-fold step dilution ratios (e.g. 4:2:1:0.5:0.25: 0.0125). In preparing a calibration curve, these different tagged peptide concentrations are prepared in one labeling step with the pre-mixed isotopologue reagents and resolved in the LC-MS system with high resolution MS. A typical calibration curve requires six peptide injections at different peptide concentrations, but the disclosed AQUAplex tag approach described here reduces this to one injection. Each injection is performed in triplicate (three replicates). The total LC-MS analysis to generate a calibration curve in triplicate is thus at least three analyses.

Figure 19:
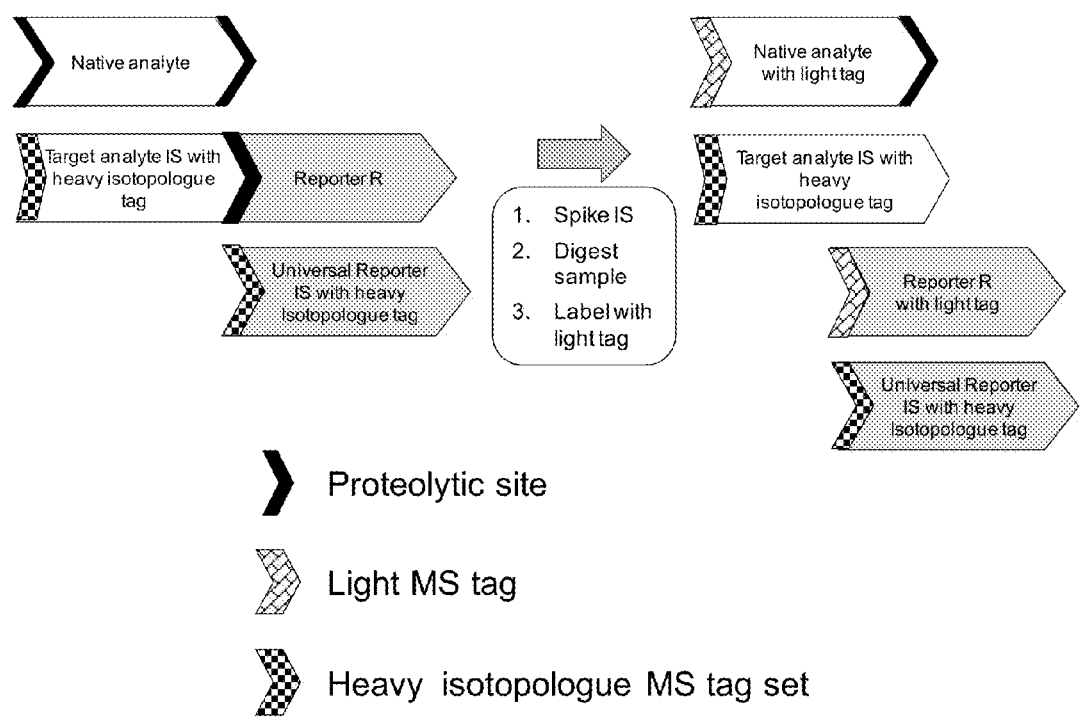
FIG. 19 schematically shows a configuration for a native analyte targeted for quantitation, an internal standard (IS) peptide corresponding to the targeted analyte linked to a reporter peptide and correlated to a universal peptide U. The concatenated IS:reporter peptide and the universal peptide are each to be labeled with a heavy isotopologue sets of a chemical MS tag, and the digested sample with spiked internal standard is to be labeled with a light, or unique isotopologue version, of the same chemical MS tag.

The universal reporter peptide X:LVALVR (SEQ ID NO. 22), where X is a proteotypic peptide of the target protein of interest and LVALVR (SEQ ID NO. 22) is a universal reporter peptide, is synthesized and labeled at the amino terminus with a heavy isotopologue triazine MS tag set mixed at a predefined ratio. Similarly, a known concentration of universal reporter internal standard peptide U is labeled at the amino terminus with the heavy isotopologue triazine MS tag set mixed at a pre-defined ratio. The labeled universal reporter peptide and universal reporter internal standard peptide from above are spiked into the target analyte sample, this mixture is digested with trypsin, and the resulting peptides are labeled with an inexpensive amine-reactive triazine tag that contained no heavy isotopes ("light" tag, FIG. 19). The final digested and labeled mixtures containing the light tag-labeled target analyte, universal reporter peptide (now cleaved into the isotopologue labeled target internal standard and light tag-labeled reporter peptide), and the universal reporter internal standard are injected into the LC-MS system. Three replicate injections are sufficient to generate a complete calibration curve and quantify the target analyte. This method thus further decreases the time needed to generate the calibration curve and includes a universal reporter peptide that served both as a digestion and labeling control.

EXAMPLE 5

Isotopically-Labeled Proteins as Internal Standards

Figure 21:
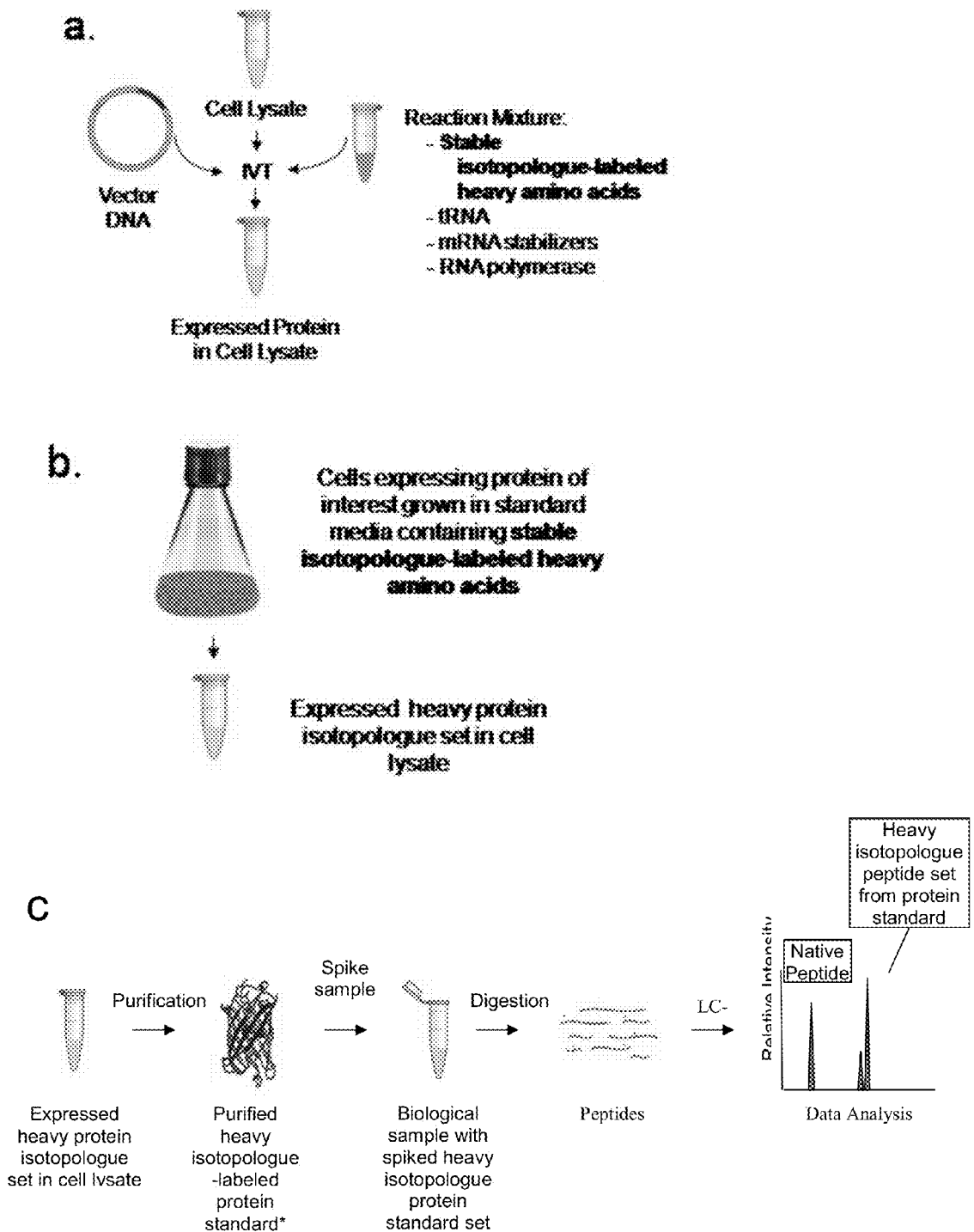
FIG. 21a-c schematically show the method for synthesis of a heavy protein using a mixture of heavy amino acid isotopologues with an in vitro protein translation kit (FIG. 21a) or with cultured cells expressing a protein of interest and grown in standard media supplemented with heavy amino acid isotopologues (FIG. 21b) followed by purification of the heavy protein isotopologues for use as an internal standard for relative quantitation (FIG. 21c).
Figure 22:
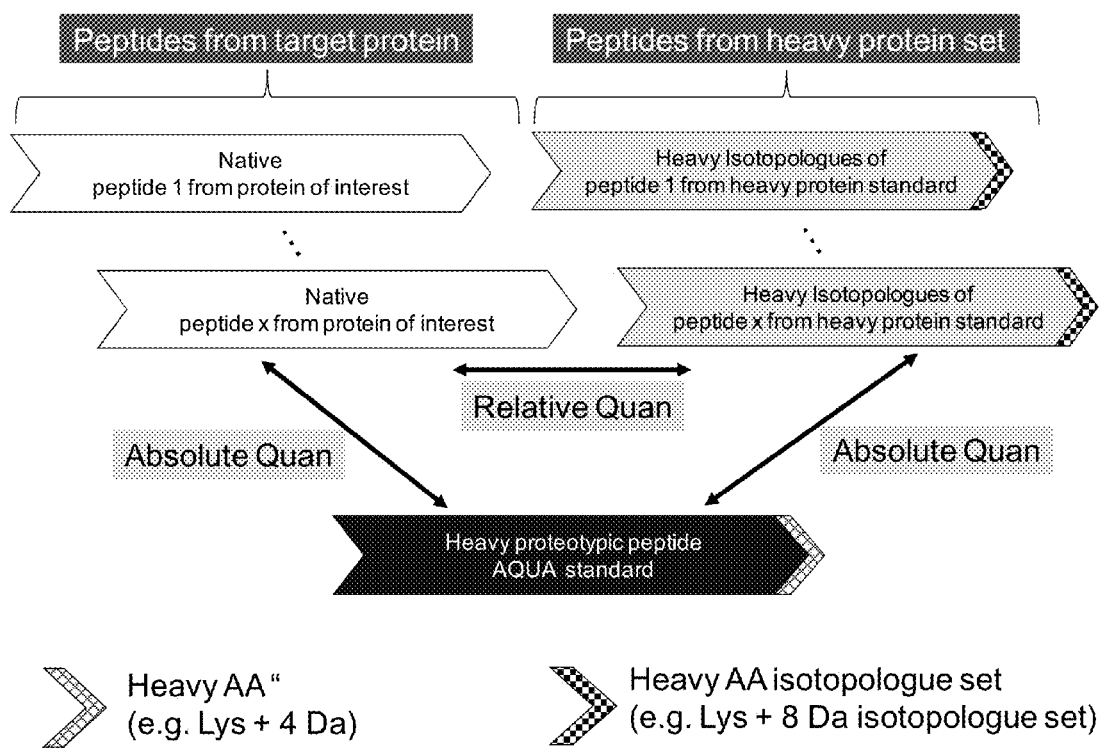
FIG. 22 shows a configuration for the use of a digested heavy isotopologue labeled protein internal standard for relative quantitation of all corresponding peptides of the native protein target in a mixture. A distinct heavy AQUA version of at least one peptide can be used for absolute quantification of the heavy isotopologue standard and the target protein.
Figure 23:
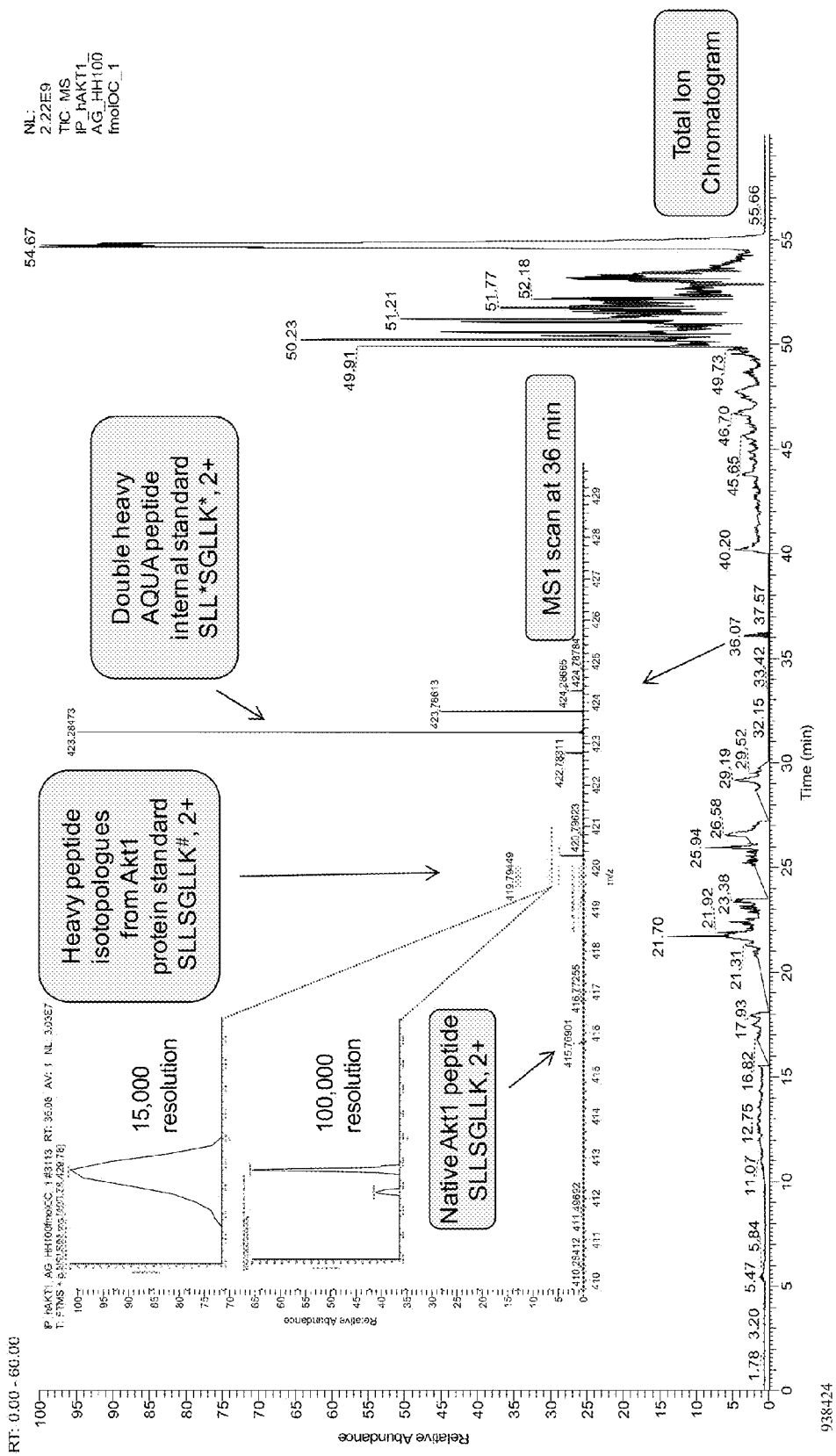
FIG. 23 shows LC-MS results for the quantification of native peptide SLLSGLLK (SEQ ID NO. 64) from Akt1 in a cell lysate using a heavy protein isotopologue set (1:4 ratio of $^{13}C_6^{15}N_2$ Lysine:$^2H_8$-Lysine used in the in vitro Akt1 synthesis, #), with 100 fmol of double heavy AQUA peptide $^{13}C_6^{15}N$-Leucine, $^{13}C_6^{15}N_2$-Lysine, SLL*SGLLK* (SEQ ID NO. 64) spiked into the mixture for absolute quantitation.

The inventive method includes synthesis of sets of heavy protein internal standards using premixed sets of precursor heavy amino acid isotopologues. A recombinant human Akt1 protein kinase was expressed with the Pierce Heavy Protein IVT Kit (Thermo Scientific, Product #88330). For this heavy $^{13}C_6{}^{15}N_2$ lysine in the kit was supplemented with heavy $^2H_8$-leucine at a 1:4 ratio to synthesize the heavy protein isotopologue set (FIGS. 21a-c). Native Akt1 is in the HeLa cell lysate used for the IVT expression system, while heavy Akt1 isotopologues were made according to instructions. Both native and heavy Akt1 were immune-enriched with an anti-Akt antibody and Protein NG-coated magnetic beads. The immune-enriched Akt sample was reduced, alkylated, digested with trypsin, and then spiked with 100-1000 fmol of the doubly labeled AKT1 AQUA heavy peptide SL(L)SGLL(K), where the bracketed amino acids were $^{13}C_6$ $^{15}N$-leucine and $^{13}C_6$ $^{15}N_2$-lysine, respectively (FIG. 22). These sample were desalted and analyzed by LC-MS/MS on a 15 cm long, 75 µm inside diameter Dionex Pepmap C18 column connected to a Thermo Scientific Orbitrap XL instrument. For the MS analysis, both 15K and 100K MS resolution settings were used to quantify a list of targeted Akt peptides. The resulting MS spectral peaks were analyzed with Thermo Scientific Xcalibur software to determine the concentration of native and heavy Akt1 protein by relative quantitation, using the SL(L)SGLL(K) heavy peptide internal standard for absolute quantitation (FIG. 23). Both normal resolution (15K) and high resolution (100,000K) MS were used to resolve the heavy peptide isotopomers to quantify Akt1-specific peptides as well as Akt peptides that are conserved in Akt2 and Akt3 isoforms. The ratios of light and heavy peptides were further verified with low resolution on a Thermo Scientific TSQ Vantage triple quadrupole mass spectrometer. This method enabled the relative quantitation of all peptides of a protein and its isoforms with the corresponding heavy protein isotopologues, and it enabled absolute quantitation using at least one AQUA peptide internal standard with a unique resolvable mass.

EXAMPLE 6

Isotopically-Labeled Peptides as Internal Standards

Table 1 lists targeted human urine and yeast proteins, and three selected proteotypic peptides to design HeavyPeptide IGNIS™ AQUAplex peptides. As shown in Table 1, ten HeavyPeptide IGNIS™ AQUAplex peptides are designed that corresponded to 30 proteotypic peptides of nine proteins (seven human proteins, three yeast proteins). Stable isotope-labeled amino acid isotopologue sets of each HeavyPeptide IGNIS™ AQUAplex peptides (purity>95%, lyophilized in sorbitol) are selected to have a mass shift and mass defects sufficient for MS analysis, with the endogenous peptides and the corresponding individual synthetic stable isotope labeled peptides with C-terminal arginine or lysine isotopologues premixed at a defined ratio (purity, lyophilized, >99 atom % isotopic enrichment); Table 2 lists the full sequence of the HeavyPeptide IGNIS™ AQUAplex peptides identifying the stable isotope amino acid heavy isotopologues.

The proteotypic peptides are selected from proteomics shotgun experiments. The reported number of observations is used as a surrogate indicator for the abundance of proteins in a specific proteome. The uniqueness of the peptide reporter is verified by blasting the amino acid sequences, LVALVR (SEQ ID NO. 22) and LVALVK (SEQ ID NO. 26), against the UniProt database; these sequences are not associated with a protein.

Calibration Curve of the Peptide Reporter

Figure 20:
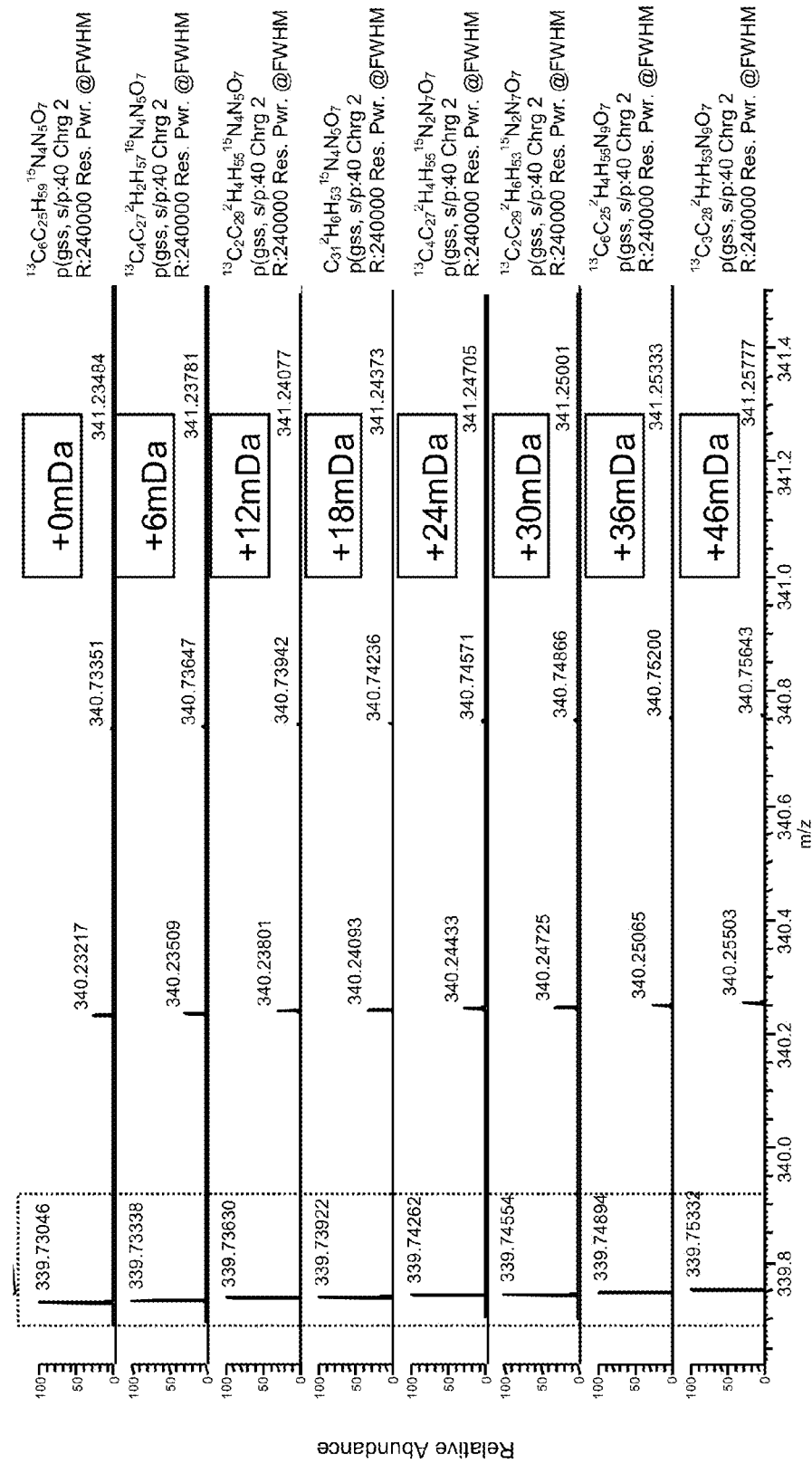
FIG. 20 shows the simulated spectra for LVALVR (SEQ ID NO. 22)+10 Da isotopologues (boxed in FIG. 7b) with a zoomed in expanded view of the isotopologue peaks (inset).

The calibration curve is performed by mixing the universal reporter peptide Uplex solution (purity>97%) with various isotope label (R for heavy arginine+10 Da using the boxed isotopologues in FIG. 7b) represented by Arg+10 Da mass defects of +0 mDa (left-most box), +6 m Da, +12 m Da, +18 mDa, +24 mDa, +30 mDa, +36 mDa, and +42 mDa. Five µL of LVALVR$^{+0mDa}$ (0.5 fmol/µL) (SEQ ID NO. 22), 15 µL LVALVR$^{+6mDa}$ (0.5 fmol/µL) (SEQ ID NO. 22), 4.5 µL LVALVR$^{+12mDa}$ (5 fmol/µL), 13.5 µL LVALVR$^{+18mDa}$ (5 fmol/µL) (SEQ ID NO. 22), 40.5 µL LVALVR$^{+24mDa}$ (5 fmol/µL) (SEQ ID NO. 22), 12.2 µL LVALVR$^{+30mDa}$ (50 fmol/µL) (SEQ ID NO. 22), 36.5 µL LVALVR$^{+36mDa}$ (50 fmol/µL) (SEQ ID NO. 22), 109.4 µL LVALVR$^{+46mDa}$ (50 fmol/µL) (SEQ ID NO. 22), and 13.6 µL of 0.1% (v/v) formic acid (in water) are mixed to obtain a final volume of 250 µL. Concentrations of these peptides in solution are 10.0 atmol/µL, 30.0 atmol/µL, 90.0 atmol/µL, 270.0 atmol/µL, 810.0 atmol/µL, 2.4 fmol/µL, 7.3 fmol/µL and 21.9 fmol/µL, respectively. The theoretical MS1 peaks for this series of eight isotopologues of LVALVR+10 Da (SEQ ID NO. 22) shows that even the z=+2 charge state of this peptide set is resolved at an MS resolution of 240,000 on a Q Exactive MS platform (FIG. 20). Further, the high intensity of the composite low resolution MS peak and the unique isotopologue mass defect peak series with high MS resolution is used to verify the internal standard and to provide exact mass information in the relevant MS region. The high resolution and accurate masses of the isotopologue series are then used to calculate the mass offsets for the specific target analyte with sub-ppm mass accuracy, allowing real-time mass calibration data and verification of the specificity of the quantitation of the target analyte. Analysis of the calibration curve is performed in triplicate by one LC-SIM run on the Q Exactive-platform. All of these isotopologue peaks are monitored for the reporter peptide.

Proteolysis of HeavyPeptide IGNIS™ AQUAplex

Each HeavyPeptide IGNIS™ AQUAplex isotopologue peptide mixture is solubilized with acetonitrile (ACN)/water (15/85) (vol/vol) to obtain a final protein concentration of 5 pmol/µL, and then sonicated for 20 minutes. HeavyPeptide IGNIS™ AQUAplex are individually digested by trypsin 1:20 (w/w) (Thermo Scientific, Rockford Ill.) for 3.5 hr at 38° C. under agitation (1400 rpm). The kinetic digestion was monitored by reaction mixture extraction every 15 minutes. To stop the digestion, all samples are diluted in 0.1% v/v formic acid to obtain a final peptide concentration of 50 fmol/µL for analysis on LC-MS (in SIM mode).

For quantitative measurements on a Thermo Scientific Q Exactive platform, all HeavyPeptide IGNIS™ AQUAplex digestion kinetic points are stoichiometrically supplemented with the corresponding synthetic stable isotope-labeled and/or stable isotopologue-labeled peptides and the universal reporter peptide U=LVALVR (SEQ ID NO. 22). The two most intense MS1 charge state ions observed from the SIM assay are monitored for all peptides.

Urine Collection and Sample Treatment

Spot midstream urine samples are collected from ten non-smoking healthy volunteers, five females and five males, age range 30-40 years. There is no history of renal dysfunction in any of the subjects or drug administration during the sample collection. Urine is centrifuged at 1 000 g relative centrifuge force (rcf) per 20 minutes at room temperature (about 19° C.-22° C.). The supernatants 1 000 g are pooled together, portioned into aliquots in 50 Falcon™ tubes and stored at −80° C.

The amount of urinary protein is estimated by a pyrogallol assay. Samples corresponding to 250 µg of urinary protein are precipitated with 100% stock solutions of acetonitrile (for HPLC) at a ratio 1:5 (v/v). Samples are incubated at room temperature overnight. After precipitation, urine samples are centrifuged at 14,000 g for 30 minutes at 4° C. The pellet is washed once with the acetonitrile, air-dried, and resuspended with 250 µL 8 M urea and 0.1 M ammonium bicarbonate. The samples are reduced with 20 mM dithiothreitol in 50 mM ammonium bicarbonate at 37° C., centrifuged at 800 rpm for 30 minutes, then alkylated with 80 mM iodoacetamide in 50 mM ammonium bicarbonate at 37° C. and centrifuged at 800 rpm for 30 min. Volume samples are adjusted at 2 M urea with 100 mM BA. Samples are then digested with trypsin (Thermo Scientific, Rockford Ill.) using a ratio of 1:20 (w/w) at 37° C. overnight. Digestion is halted by adding formic acid to obtain a pH 2-3. Sep-Pak C18 reverse phase cartridges, 100 mg (Waters, Milford Mass.) are used to clean and desalt the samples after protein digestion. The peptides are eluted using 1 mL of 50% acetonitrile and 0.1% formic acid, dried, and stored at −20° C. until LC-MS analysis.

Calibration Curve of HeavyPeptide IGNIS™ AQUAplex in Urine Samples

Dilution curves of the heavy proteotypic peptides from digested HeavyPeptide IGNIS™ are performed in a mixture of digested pooled urine sample (1 ug/mL urine proteins), containing three digested exogenous yeast proteins (carboxypeptidase Y, enolase 1, and alcohol dehydrogenase 1) at 100 ng/mL individually. Each dilution series corresponds to three data points spanning a concentration ranging from 0.002 fmol/µL to 40 fmol/µL. Protein levels of spiked digested yeast proteins and human urine proteins are determined by iSR using the heavy proteotypic peptides from digested HeavyPeptide IGNIS™ AQUAplex.

LC-MS Conditions

Urinary and yeast tryptic peptides are analyzed on a Q Exactive Mass Spectrometer (ThermoFisher, San Jose Calif.). Instruments are equipped with a nanoelectrospray ion source. Chromatographic separations of peptides are performed on an Ultimate 3000 (Dionex, Netherlands) high performance liquid chromatographer operated in the nano-flow mode. Samples are loaded on a Trap column (Acclaim PepMap C18, 3 µm, 100 Å, 0.075×20 mm, Dionex) and separated on an analytical column (Acclaim PepMap® RSLC C18, 2 µm, 100 Å, 0.075×150 mm, Dionex) coupled with a PicoTip™ electrospray emitter (30 µm) (New Objective, Woburn Mass.) maintained at 1.2 kV. The column temperature is fixed at 35° C. Peptides are separated with a linear gradient of acetonitrile/water, containing 0.1% formic acid, at a flow rate of 300 nL/min. A gradient from 2% to 35% acetonitrile in 33 minutes is used. One µL of each sample is injected.

TABLE 1

| Heavy Peptide IGNIS™ AQUAplex Name | Protein Name | Organism | Swissprot ID | Selected protetotypic peptides (PI, PH, PHI) | | |
|---|---|---|---|---|---|---|
| | | | | P I | P II | P III |
| | uromodulin | human | P07911 | DWVSVVTPAR (SEQ ID NO. 23) | DSTIQVVENGESSQGR (SEQ ID NO. 24) | SGSVIDQSR (SEQ ID NO. 25) |
| TRFE | serotransferrin | human | P02787 | DGAGDVAFVK (SEQ ID NO. 28) | SASDLTWDNLK (SEQ ID NO. 29) | EGYYGYTGAFR (SEQ ID NO. 30) |
| LG3BP* | galectin-3-binding protein | human | Q08380 | LADGGATNQGR (SEQ ID NO. 32) | SDLAVPSELALLK (SEQ ID NO. 33) | ELSEALGQIFDSQR (SEQ ID NO. 34) |
| CD44 | CD44 antigen | human | P16070 | FAGVFHVEK (SEQ ID NO. 36) | YGFIEGHVVIPR (SEQ ID NO. 37) | ALSIGFETCR (SEQ ID NO. 38) |
| CATD | cathepsin d | human | P07339 | LVDQNIFSFYLSR (SEQ ID NO. 40) | VSTLPAITLK (SEQ ID NO. 41) | YSQAVPAVTEGPIPEVLK (SEQ ID NO. 42) |
| KNG 1 | kininogen-1 | human | P01042 | TVGSDTFYSFK (SEQ ID NO. 44) | YFIDFVAR (SEQ ID NO. 45) | YNSQNQSNNQFVLYR (SEQ ID NO. 46) |
| ANAG | alpha-N-acetyl-glucosaminidase | human | P54802 | LLLTSAPSLATSPAFR (SEQ ID NO. 48) | YDLLDLTR (SEQ ID NO. 49) | SDVFEAWR (SEQ ID NO. 50) |
| ENO1 | enolase 1 | yeast | P00924 | NVNDVIAPAFVK (SEQ ID NO. 52) | LGANAILGVSLAASR (SEQ ID NO. 53) | TAGIQIVADDLTVTNPK (SEQ ID NO. 54) |
| CBPY | carboxypeptidase Y | yeast | P00729 | YDEEFASQK (SEQ ID NO. 56) | HFTYLR (SEQ ID NO. 57) | AWTDVLPWK (SEQ ID NO. 58) |
| ADH1 | alcohol dehydrogenase 1 | yeast | P00330 | GVIFYESHGK (SEQ ID NO. 60) | SIGGEVFIDFTK (SEQ ID NO. 61) | VVGLSTLPEIYEK (SEQ ID NO. 62) |

*no analysis performed

TABLE 2

| Heavy Peptide IGNIS™ AQUAplex name | Full sequence of isotopologue labeled polypeptide + reporter peptide | P I | P II | P III |
|---|---|---|---|---|
| UROM | DWVSVVTPARDSTIQVVENGESSQGRSGSV IDQSRLVALVR (SEQ ID NO. 27) | DWVSVVTPAR (SEQ ID NO. 23) | DSTIQVVENGESSQGR (SEQ ID NO. 24) | SGSVIDQSR (SEQ ID NO. 25) |
| TRFE | DGAGDVAFVKSASDLTWDNLKEGYYGYTGAFRLVALVR (SEQ ID NO. 31) | DGAGDVAFVK (SEQ ID NO. 28) | SASDLTWDNLK (SEQ ID NO. 29) | EGYYGYTGAFR (SEQ ID NO. 30) |
| LG3BP | LADGGATNQGRSDLAVPSELALLKELSEALGQIFDS QRLVALVR (SEQ ID NO. 35) | LADGGATNQGR (SEQ ID NO. 32) | SDLAVPSELALLK (SEQ ID NO. 33) | ELSEALGQIFDSQR (SEQ ID NO. 34) |
| CD44 | FAGVFHVEKYGFIEGHVVIPRALSIGFETCRLVALVR (SEQ ID NO. 39) | FAGVFHVEK (SEQ ID NO. 36) | YGFIEGHVVIPR (SEQ ID NO. 37) | ALSIGFETCR (SEQ ID NO. 38) |
| CATD | LVDQNIFSFYLSRVSTLPAITLKYSQAVPAVTEGP IPEVLKLVALVR (SEQ ID NO. 43) | LVDQNIFSFYLSR (SEQ ID NO. 40) | VSTLPAITLK (SEQ ID NO. 41) | YSQAVPAVTEGPIPEV LK (SEQ ID NO. 42) |
| KNG1 | TVGSDTFYSFKYFIDFVARYNSQNQSNNQFVLYR LVALVR (SEQ ID NO. 47) | TVGSDTFYSFK (SEQ ID NO. 44) | YFIDFVAR (SEQ ID NO. 45) | YNSQNQSNNQFVLYR (SEQ ID NO. 46) |
| ANAG | LLLTSAPSLATSPAFRYDLLDLTRSDVFEAWRLVALVR (SEQ ID NO. 51) | LLLTSAPSLATSPAFR (SEQ ID NO. 48) | YDLLDLTR (SEQ ID NO. 49) | SDVFEAWR (SEQ ID NO. 50) |
| ENO1 | NVNDVIAPAFVKLGANAILGVSLAASRTAGIQIVADDL TVTNPKLVALVR (SEQ ID NO. 55) | NVNDVIAPAFVK (SEQ ID NO. 52) | LGANAILGVSLAASR (SEQ ID NO. 53) | TAGIQIVADDLTVTNPK (SEQ ID NO. 54) |
| CBPY | YDEEFASQKHFTYLRAWTDVLPWKLVALVR (SEQ ID NO. 59) | YDEEFASQK (SEQ ID NO. 56) | HFTYLR (SEQ ID NO. 57) | AWTDVLPWK (SEQ ID NO. 58) |
| ADH1 | GVIFYESHGKSIGGEVFIDFTKVVGLSTLPEIY EKLVALVR (SEQ ID NO. 63) | GVIFYESHGK (SEQ ID NO. 60) | SIGGEVFIDFTK (SEQ ID NO. 61) | VVGLSTLPEIYEK (SEQ ID NO. 62) |

Applicants incorporate by reference the material contained in the accompanying computer readable Sequence Listing identified as 073986_281.txt, having a file creation date of Jun. 5, 2014, 1:41 p.m., and a file size of 19.4 kilobytes.

The embodiments shown and described in the specification are only specific embodiments of the inventor who is skilled in the art and is not limiting in any way. Therefore, various changes, modifications, or alterations to those embodiments may be made without departing from the spirit of the invention in the scope of the following claims.

All references are expressly incorporated by reference herein in their entirety.

What is claimed is:

1. A method for quantitation of a target protein or peptide in a sample by mass spectroscopy (MS), the method comprising
preparing internal standard isotopologues using at least one set of multiplexed heavy peptide internal standards, wherein each peptide within the at least one set contains the same amino acid sequence, but the peptides within the set differ by a mass defect created by incorporating heavy isotopes on different atoms within at least one amino acid molecule resulting in internal standard isotopologues, and
quantitating at least one target protein or peptide using the multiplexed internal standard isotopologues.

2. The method of claim 1 wherein the heavy peptide internal standards within each set contain the same number of total neutrons within each peptide, but differ in that the heavy atom distribution within the amino acids is unique to each peptide.

3. The method of claim 1 wherein the heavy peptide internal standards within each set are resolved as a single peak under low resolution mass spectrometry, and are resolved as multiple peaks under high resolution mass spectrometry.

4. The method of claim 1 wherein the heavy peptide internal standards within each set contain mass differences between each peptide that are less than 1 Dalton.

5. The method of claim 1 wherein the sample is a biological sample and the method is used for a diagnostic assay.

6. The method of claim 1 further identifying distinct peptides from the target analyte that are regulated independent of the protein level, and determining stoichiometry of native to modified peptides of the target analyte.

7. The method of claim 1 used in a universal reporter assay.

8. The method of claim 1 used for at least one of multi-sample analysis or multi-target analysis.

9. The method of claim 1 wherein the heavy peptides are prepared by synthesizing a mixture of at least two peptides with isotopologues of heavy amino acids, resulting in heavy peptides having mass defects.

10. The method of claim 9 wherein isotopologues are prepared by mixing solid phase immobilized AQUA peptide precursors at a defined ratio.

11. The method of claim 1 wherein the sample is prepared by effecting cleavage of the target protein or peptide.

12. The method of claim 1 performed for targeted peptide quantitation using multiplexed internal standard peptide isotopologues by high resolution mass spectrometry, and/or to verify the target protein or peptide is free of isobaric interference.

13. The method of claim 1 generating peptide internal standards for low abundance proteins.

14. The method of claim 1 used for generating in a standard curve for MS analysis, the method comprising
preparing a plurality of isotopologues of an amino acid to generate a heavy peptide standard,
mixing the plurality of isotopologues at fixed ratios,
separating the mixed isotopologues at a low resolution quantitation or a high resolution quantitation, and
plotting a standard curve using the mixed isotopologues separation.

15. The method of claim 1 where the internal standard isotopologues are prepared by spiking a plurality of mass tag isotopologues and a peptide internal standard labeled with the mass tag isotopologues into a target sample, then digesting the target sample, labeling the target sample and resulting universal reporter peptide with a light version of the mass tag, and separating the peptides by MS analysis.

16. A kit for quantifying proteins, polypeptides, or peptides in a sample, the kit comprising a plurality of heavy isotope labeled peptide standards having the same amino acid sequence, each comprising different isotopologues of heavy amino acids and each having the same nominal mass and chemical formula but different permutations of 13C—, 15N—, 18O—, 34S—, or 2H—, to result in peptide standards with milliDalton mass defects, and instructions for quantifying the proteins, polypeptides, or peptides in the sample by mass spectroscopy using the kit.

17. The kit of claim 16 wherein the instructions are for using the standards in at least one of a multiplex assay or a diagnostic assay.

18. A mass spectrometry (MS) quantitation system comprising
a sample prepared for MS quantitation,
a plurality of mass tag isotopologues,
an ion source,
a mass analyzer with isotopologue separation, and
a detector with isotopologue peptide internal standard resolution.

19. The system of claim 18 where the detector quantitates a plurality of mass spectroscopy peaks using a standard curve generated for each isotopologue set.

20. The system of claim 18 where the detector is capable of 100,000 mass resolution or higher.

* * * * *